United States Patent
Fallon et al.

(10) Patent No.: US 9,415,014 B2
(45) Date of Patent: Aug. 16, 2016

(54) ENZYME DELIVERY SYSTEMS AND METHODS OF PREPARATION AND USE

(75) Inventors: Joan M. Fallon, Bronxville, NY (US); Matthew Heil, Sherman, CT (US)

(73) Assignee: Curemark, LLC, Rye, NY (US)

( * ) Notice: Subject to any disclaimer, the term of this patent is extended or adjusted under 35 U.S.C. 154(b) by 0 days.

(21) Appl. No.: 13/193,346

(22) Filed: Jul. 28, 2011

(65) Prior Publication Data
US 2012/0027848 A1 Feb. 2, 2012

Related U.S. Application Data

(62) Division of application No. 12/386,051, filed on Apr. 13, 2009.

(51) Int. Cl.
| | |
|---|---|
| A61K 9/00 | (2006.01) |
| A61K 9/14 | (2006.01) |
| A61K 9/16 | (2006.01) |
| A61K 9/50 | (2006.01) |
| A61K 38/46 | (2006.01) |
| A61K 38/47 | (2006.01) |
| A61K 38/48 | (2006.01) |
| A61K 38/54 | (2006.01) |

(52) U.S. Cl.
CPC ............... *A61K 9/1682* (2013.01); *A61K 9/16* (2013.01); *A61K 9/167* (2013.01); *A61K 9/1617* (2013.01); *A61K 9/5015* (2013.01); *A61K 9/5063* (2013.01); *A61K 38/465* (2013.01); *A61K 38/47* (2013.01); *A61K 38/48* (2013.01); *A61K 38/54* (2013.01)

(58) Field of Classification Search
None
See application file for complete search history.

(56) References Cited

U.S. PATENT DOCUMENTS

| | | | |
|---|---|---|---|
| 3,002,883 | A | 10/1961 | Butt et al. |
| 3,223,594 | A | 12/1965 | Serge |
| 3,322,626 | A | 5/1967 | D'Argento |
| 3,357,894 | A | 12/1967 | Jose et al. |
| 3,515,642 | A | 6/1970 | Mima et al. |
| 3,574,819 | A | 4/1971 | Gross et al. |
| 3,860,708 | A | 1/1975 | Prout |
| 3,940,478 | A | 2/1976 | Kurtz |
| 4,079,125 | A | 3/1978 | Sipos |
| 4,145,410 | A | 3/1979 | Sears |
| 4,241,046 | A | 12/1980 | Papahadjopoulos et al. |
| 4,280,971 | A | 7/1981 | Wischniewski et al. |
| 4,447,412 | A | 5/1984 | Bilton |
| 4,456,544 | A | 6/1984 | Lupova et al. |
| 4,623,624 | A | 11/1986 | Schultze |
| 4,826,679 | A | 5/1989 | Roy |
| 5,190,775 | A | 3/1993 | Klose |
| 5,250,418 | A | 10/1993 | Moller et al. |
| 5,324,514 | A | 6/1994 | Sipos |
| 5,378,462 | A | 1/1995 | Boedecker et al. |
| 5,436,319 | A | 7/1995 | Kung et al. |
| 5,437,319 | A | 8/1995 | Garuglieri |
| 5,439,935 | A | 8/1995 | Rawlings et al. |
| 5,460,812 | A | 10/1995 | Sipos |
| 5,476,661 | A | 12/1995 | Pillai et al. |
| 5,527,678 | A | 6/1996 | Blaser et al. |
| 5,585,115 | A | 12/1996 | Sherwood et al. |
| 5,607,863 | A | 3/1997 | Chandler |
| 5,648,335 | A | 7/1997 | Lewis et al. |
| 5,674,532 | A | 10/1997 | Atzl et al. |
| 5,686,311 | A | 11/1997 | Shaw |
| 5,750,104 | A | 5/1998 | Sipos |
| 5,776,917 | A | 7/1998 | Blank et al. |
| 5,858,758 | A | 1/1999 | Hillman et al. |
| 5,952,178 | A | 9/1999 | Lapidus et al. |
| 5,958,875 | A | 9/1999 | Longo et al. |
| 5,977,175 | A | 11/1999 | Lin |
| 5,985,891 | A | 11/1999 | Rowe |
| 6,011,001 | A | 1/2000 | Navia et al. |
| 6,013,286 | A | 1/2000 | Klose |
| 6,020,310 | A | 2/2000 | Beck et al. |
| 6,020,314 | A | 2/2000 | McMichael |
| 6,096,338 | A | 8/2000 | Lacy et al. |
| 6,149,585 | A | 11/2000 | Gray |
| 6,153,236 | A | 11/2000 | Wu et al. |
| 6,168,569 | B1 | 1/2001 | McEwen et al. |
| 6,187,309 | B1 | 2/2001 | McMichael et al. |
| 6,197,746 | B1 | 3/2001 | Beck et al. |
| 6,210,950 | B1 | 4/2001 | Johnson et al. |
| 6,251,478 | B1 | 6/2001 | Pacifico et al. |

(Continued)

FOREIGN PATENT DOCUMENTS

| | | |
|---|---|---|
| CA | 2198317 A1 | 2/1997 |
| CA | 2263703 A1 | 8/1999 |

(Continued)

OTHER PUBLICATIONS

U.S. Appl. No. 13/271,783, filed Oct. 12, 2011, Fallon.
Final Offce Action dated Jan. 3, 2012 for U.S. Appl. No. 10/681,018.
Office action dated Jan. 12, 2012 for U.S. Appl. No. 12/047,818.
Office action dated Dec. 15, 2011 for U.S. Appl. No. 12/493,147.
Rajakumar, et al. Proteasomal activity in placentas from women with preeclampsia and intrauterine growth restriction: implications for expression of HIF-alpha proteins. Placenta. Mar. 2008;29(3):290-9. Epub Jan. 28, 2008.

(Continued)

*Primary Examiner* — Daniel E Kolker
*Assistant Examiner* — Aditi Dutt
(74) *Attorney, Agent, or Firm* — Wilson Sonsini Goodrich & Rosati

(57) ABSTRACT

This invention relates to coated digestive enzyme preparations and enzyme delivery systems and pharmaceutical compositions comprising the preparations. This invention further relates to methods of preparation and use of the systems, pharmaceutical compositions and preparations to treat persons having ADD, ADHD, autism, cystic fibrosis and other behavioral and neurological disorders.

65 Claims, 14 Drawing Sheets

(56) References Cited

U.S. PATENT DOCUMENTS

| | | |
|---|---|---|
| 6,261,602 B1 | 7/2001 | Calanchi et al. |
| 6,261,613 B1 | 7/2001 | Narayanaswamy et al. |
| 6,280,726 B1 | 8/2001 | Weinrauch et al. |
| 6,287,585 B1 | 9/2001 | Johansen |
| 6,309,669 B1 | 10/2001 | Setterstrom et al. |
| 6,399,101 B1 | 6/2002 | Frontanes et al. |
| 6,482,839 B1 | 11/2002 | Thornfeldt |
| 6,498,143 B1 | 12/2002 | Beck et al. |
| 6,534,063 B1 | 3/2003 | Fallon |
| 6,534,259 B1 | 3/2003 | Wakefield |
| 6,558,708 B1 | 5/2003 | Lin |
| 6,562,629 B1 | 5/2003 | Lin et al. |
| 6,569,463 B2 | 5/2003 | Patel et al. |
| 6,632,429 B1 | 10/2003 | Fallon |
| 6,660,831 B2 | 12/2003 | Fallon |
| 6,727,073 B1 | 4/2004 | Moore et al. |
| 6,743,447 B2 | 6/2004 | Labergerie et al. |
| 6,764,447 B2 | 7/2004 | Iliff |
| 6,783,757 B2 | 8/2004 | Brudnak |
| 6,790,825 B2 | 9/2004 | Beck et al. |
| 6,797,291 B2 | 9/2004 | Richardson |
| 6,808,708 B2 | 10/2004 | Houston |
| 6,821,514 B2 | 11/2004 | Houston |
| 6,827,688 B2 | 12/2004 | Goto et al. |
| 6,835,397 B2 | 12/2004 | Lee et al. |
| 6,852,487 B1 | 2/2005 | Barany et al. |
| 6,861,053 B1 | 3/2005 | Lin et al. |
| 6,899,876 B2 | 5/2005 | Houston |
| 6,923,988 B2 | 8/2005 | Patel et al. |
| 6,980,958 B1 | 12/2005 | Surwit et al. |
| 7,048,906 B2 | 5/2006 | Lin et al. |
| 7,081,239 B2 | 7/2006 | Lin |
| 7,091,182 B2 | 8/2006 | Beck et al. |
| 7,101,573 B2 | 9/2006 | Szymczak et al. |
| 7,122,357 B2 | 10/2006 | Sander-Struckmeier et al. |
| 7,129,053 B1 | 10/2006 | Reiter et al. |
| 7,138,123 B2 | 11/2006 | Fallon |
| 7,232,670 B2 | 6/2007 | D'Azzo et al. |
| 7,244,412 B2 | 7/2007 | Lin |
| 7,285,633 B2 | 10/2007 | Wu et al. |
| 7,381,698 B2 | 6/2008 | Fein et al. |
| 7,395,216 B2 | 7/2008 | Rosenfeld et al. |
| 7,479,378 B2 | 1/2009 | Potthoff et al. |
| 7,483,747 B2 | 1/2009 | Gliner et al. |
| 7,588,757 B2 | 9/2009 | Ozawa et al. |
| 7,608,245 B2 | 10/2009 | Lin |
| 7,630,913 B2 | 12/2009 | Kay |
| 7,658,918 B1 | 2/2010 | Ortenzi et al. |
| 7,718,169 B2 | 5/2010 | Margolin et al. |
| 7,736,622 B2 | 6/2010 | Lin et al. |
| 7,935,799 B2 | 5/2011 | Lin et al. |
| 7,945,451 B2 | 5/2011 | Cosentino et al. |
| 8,008,036 B2 | 8/2011 | Fallon |
| 8,012,710 B2 | 9/2011 | Fallon |
| 8,012,930 B2 | 9/2011 | Fallon |
| 8,030,002 B2 | 10/2011 | Fallon |
| 8,055,516 B2 | 11/2011 | Iliff |
| 8,066,636 B2 | 11/2011 | Iliff |
| 8,105,584 B2 | 1/2012 | Fallon |
| 8,211,661 B2 | 7/2012 | Fallon |
| 8,221,747 B2 * | 7/2012 | Ortenzi et al. ............ 424/94.6 |
| 8,437,689 B2 | 5/2013 | Mazar |
| 8,613,918 B2 | 12/2013 | Fallon |
| 8,921,054 B2 | 12/2014 | Fallon |
| 8,980,252 B2 | 3/2015 | Fallon |
| 9,017,665 B2 | 4/2015 | Fallon |
| 9,023,344 B2 | 5/2015 | Fallon |
| 9,056,050 B2 | 6/2015 | Fallon et al. |
| 9,061,033 B2 | 6/2015 | Fallon |
| 2001/0023360 A1 | 9/2001 | Nelson et al. |
| 2001/0024660 A1 | 9/2001 | Ullah et al. |
| 2002/0001575 A1 | 1/2002 | Foreman |
| 2002/0037284 A1 | 3/2002 | Fallon |
| 2002/0061302 A1 | 5/2002 | Sander-Struckmeier et al. |
| 2002/0090653 A1 | 7/2002 | Fallon |
| 2002/0094367 A1 | 7/2002 | Fuglsang et al. |
| 2002/0103675 A1 | 8/2002 | Vanelli |
| 2002/0119914 A1 | 8/2002 | Zhu et al. |
| 2002/0141987 A1 | 10/2002 | Bjarnason |
| 2002/0183229 A1 | 12/2002 | Simpson |
| 2003/0097122 A1 | 5/2003 | Ganz et al. |
| 2004/0005304 A1 | 1/2004 | Brudnak |
| 2004/0028689 A1 | 2/2004 | Borody |
| 2004/0029752 A1 | 2/2004 | Sava et al. |
| 2004/0057944 A1 | 3/2004 | Galle et al. |
| 2004/0057962 A1 | 3/2004 | Timmerman |
| 2004/0071683 A1 | 4/2004 | Fallon |
| 2004/0076590 A1 | 4/2004 | Wilkins |
| 2004/0101562 A1 | 5/2004 | Maio |
| 2004/0121002 A1 | 6/2004 | Lee et al. |
| 2004/0209790 A1 | 10/2004 | Sava et al. |
| 2005/0079594 A1 | 4/2005 | Marion |
| 2005/0137134 A1 | 6/2005 | Gill et al. |
| 2005/0170479 A1 | 8/2005 | Weaver et al. |
| 2005/0187130 A1 | 8/2005 | Brooker et al. |
| 2005/0232894 A1 | 10/2005 | Weiner et al. |
| 2006/0105379 A1 | 5/2006 | Wu et al. |
| 2006/0115467 A1 | 6/2006 | Pangborn et al. |
| 2006/0121017 A1 | 6/2006 | Margolin et al. |
| 2006/0182728 A1 | 8/2006 | Fallon |
| 2006/0183180 A1 | 8/2006 | Fallon |
| 2006/0198838 A1 | 9/2006 | Fallon |
| 2006/0258599 A1 | 11/2006 | Childers |
| 2006/0259995 A1 | 11/2006 | Cayouette et al. |
| 2007/0031399 A1 | 2/2007 | Edens et al. |
| 2007/0053895 A1 | 3/2007 | Fallon |
| 2007/0092501 A1 | 4/2007 | Houston |
| 2007/0116695 A1 | 5/2007 | Fallon |
| 2007/0148151 A1 | 6/2007 | Frink et al. |
| 2007/0148152 A1 | 6/2007 | Shlieout et al. |
| 2007/0148153 A1 | 6/2007 | Shlieout et al. |
| 2007/0203426 A1 | 8/2007 | Kover et al. |
| 2008/0019959 A1 | 1/2008 | Becher et al. |
| 2008/0020036 A1 | 1/2008 | Jolly |
| 2008/0057086 A1 | 3/2008 | Etter |
| 2008/0058282 A1 | 3/2008 | Fallon |
| 2008/0112900 A1 | 5/2008 | Du-Thumm et al. |
| 2008/0112944 A1 | 5/2008 | Pangborn et al. |
| 2008/0152637 A1 | 6/2008 | Fallon |
| 2008/0161265 A1 | 7/2008 | Fallon et al. |
| 2008/0166334 A1 | 7/2008 | Fallon |
| 2008/0199448 A1 | 8/2008 | Ross et al. |
| 2008/0254009 A1 | 10/2008 | Finegold |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0317731 A1 | 12/2008 | Gramatikova et al. |
| 2009/0110674 A1 | 4/2009 | Loizou |
| 2009/0117180 A1 | 5/2009 | Ortenzi et al. |
| 2009/0130081 A1 | 5/2009 | Fallon |
| 2009/0226414 A1 | 9/2009 | Tijssen et al. |
| 2009/0232789 A1 | 9/2009 | Fallon |
| 2009/0233344 A1 | 9/2009 | Kurfurst et al. |
| 2009/0263372 A1 | 10/2009 | Fallon |
| 2009/0286270 A1 | 11/2009 | Fallon |
| 2009/0304670 A1 | 12/2009 | Edens et al. |
| 2009/0324572 A1 | 12/2009 | Fallon |
| 2009/0324730 A1 | 12/2009 | Fallon |
| 2010/0092447 A1 | 4/2010 | Fallon |
| 2010/0169409 A1 | 7/2010 | Fallon et al. |
| 2010/0196344 A1 | 8/2010 | Margolin et al. |
| 2010/0209507 A1 | 8/2010 | Lin et al. |
| 2010/0233218 A1 | 9/2010 | Fallon |
| 2010/0239559 A1 | 9/2010 | Freedman et al. |
| 2010/0260857 A1 | 10/2010 | Fallon et al. |
| 2010/0270183 A1 | 10/2010 | Ortenzi et al. |
| 2010/0285116 A1 | 11/2010 | Joshi |
| 2011/0029922 A1 | 2/2011 | Hoffberg et al. |
| 2011/0052706 A1 | 3/2011 | Moest et al. |
| 2011/0081320 A1 | 4/2011 | Westall et al. |
| 2011/0112005 A1 | 5/2011 | Brooker et al. |
| 2011/0182818 A1 | 7/2011 | Fallon |
| 2011/0200574 A1 | 8/2011 | Jolly et al. |
| 2012/0070504 A1 | 3/2012 | Fallon |

(56) References Cited

U.S. PATENT DOCUMENTS

| | | |
|---|---|---|
| 2012/0128764 A1 | 5/2012 | Venkatesh et al. |
| 2012/0201875 A1 | 8/2012 | Ortenzi et al. |
| 2012/0258149 A1 | 10/2012 | Fallon et al. |
| 2014/0187512 A1 | 7/2014 | Fallon et al. |
| 2014/0348881 A1 | 11/2014 | Fallon |
| 2015/0023944 A1 | 1/2015 | Fallon |
| 2015/0140550 A1 | 5/2015 | Fallon |
| 2015/0147308 A1 | 5/2015 | Fallon et al. |
| 2015/0150955 A1 | 6/2015 | Fallon et al. |

FOREIGN PATENT DOCUMENTS

| | | |
|---|---|---|
| CN | 1031562 A | 3/1989 |
| CN | 1329923 A | 1/2002 |
| DE | 4332985 | 3/1995 |
| DE | 202010004926 U1 | 7/2010 |
| EP | 0425214 A2 | 5/1991 |
| EP | 0436110 A1 | 7/1991 |
| EP | 0451484 A1 | 10/1991 |
| EP | 0564739 A2 | 10/1993 |
| EP | 0564739 A3 | 4/1995 |
| EP | 1162995 B1 | 6/2003 |
| EP | 1335706 B1 | 4/2005 |
| EP | 1019072 B1 | 5/2005 |
| EP | 1604677 A1 | 12/2005 |
| EP | 1931317 B1 | 6/2008 |
| EP | 2258837 A1 | 12/2010 |
| GB | 669782 A | 4/1952 |
| GB | 2347742 A | 9/2000 |
| JP | 62230714 A | 10/1987 |
| JP | H 04-364119 A | 12/1992 |
| TW | 310277 B | 7/1997 |
| WO | WO 84/02846 A1 | 8/1984 |
| WO | WO 90/02562 A1 | 3/1990 |
| WO | WO 94/19005 A1 | 9/1994 |
| WO | WO 95/22344 A1 | 8/1995 |
| WO | WO 97/32480 A1 | 9/1997 |
| WO | WO 98/22499 A2 | 5/1998 |
| WO | WO 98/22499 A3 | 7/1998 |
| WO | WO-9832336 A2 | 7/1998 |
| WO | WO-9832336 A3 | 7/1998 |
| WO | WO 98/52593 A1 | 11/1998 |
| WO | WO 99/64059 A2 | 12/1999 |
| WO | WO 00/09142 A1 | 2/2000 |
| WO | WO 99/64059 A3 | 3/2000 |
| WO | WO 00/21504 A1 | 4/2000 |
| WO | WO 01/27612 A2 | 4/2001 |
| WO | WO 01/43764 A2 | 6/2001 |
| WO | WO 01/45835 A1 | 6/2001 |
| WO | WO 01/27612 A3 | 10/2001 |
| WO | WO 01/43764 A3 | 11/2001 |
| WO | WO 02/14537 A2 | 2/2002 |
| WO | WO-0219828 A1 | 3/2002 |
| WO | WO 02/14537 A3 | 5/2002 |
| WO | WO 02/051352 A2 | 7/2002 |
| WO | WO 03/051345 A2 | 6/2003 |
| WO | WO 03/059088 A1 | 7/2003 |
| WO | WO 2004/060074 A1 | 7/2004 |
| WO | WO 2005/115445 A1 | 12/2005 |
| WO | WO 2006/031554 A2 | 3/2006 |
| WO | WO 2006/044529 A1 | 4/2006 |
| WO | WO 2006/031554 A3 | 9/2006 |
| WO | WO 2007/002572 A2 | 1/2007 |
| WO | WO 2007/147714 A1 | 12/2007 |
| WO | WO 2008/021987 A2 | 2/2008 |
| WO | WO 2008/102264 A2 | 8/2008 |
| WO | WO 2009/114757 A2 | 9/2009 |
| WO | WO 2010/002972 A1 | 1/2010 |
| WO | WO 2010/025126 A1 | 3/2010 |
| WO | WO 2010/080830 A1 | 7/2010 |
| WO | WO 2010/080835 A1 | 7/2010 |
| WO | WO 2010/120781 A1 | 10/2010 |
| WO | WO 2011/000924 A1 | 1/2011 |

OTHER PUBLICATIONS

Tran, et al. Treatment of complex regional pain syndrome: a review of the evidence. Can J Anaesth. Feb. 2010;57(2):149-66.
U.S. Appl. No. 13/313,629, filed Dec. 7, 2011, Fallon.
U.S. Appl. No. 13/313,708, filed Dec. 7, 2011, Fallon.
Final Office Action dated Jan. 26, 2012 for U.S. Appl. No. 12/487,864.
Isaksson, et al. Pain reduction by an oral pancreatic enzyme preparation in chronic pancreatitis. Digestive Dis. Sci. 1983; 28(2):97-102.
Lashkari, et al. Williams-Beuren syndrome: An update and review for the primary physician. Clinical Pediatrics. 1999; 38(4):189-208.
Meyer-Lindenberg, et al. Neural mechanisms in Williams syndrome: a unique window to genetic influences on cognition and behaviour. Nat. Rev. Neurosci. 2006; 7(5):380-93.
Notice of Allowance dated Feb. 17, 2012 for U.S. Appl. No. 10/681,018.
Office Action dated Feb. 1, 2012 for U.S. Appl. No. 12/493,122.
U.S. Appl. No. 13/407,408, filed Feb. 28, 2012, Fallon et al.
Office Action dated Mar. 5, 2012 for U.S. Appl. No. 12/535,676.
U.S. Appl. No. 13/448,061, filed Apr. 16, 2012, Fallon.
Elkashef, et al. Biological markers of cocaine addiction: implications for medications development. Addict Biol. Jun. 2003;8(2):123-39.
Fallon. Could one of the most widely prescribed antibiotics amoxicillin/clavulanate "augmentin" be a risk factor for autism? Med Hypotheses. 2005;64(2):312-5.
Horvath, et al. Autism and gastrointestinal symptoms. Curr Gastroenterol Rep. Jun. 2002;4(3):251-8.
Jenkins, et al. Management of gastroenteritis. Archives of Disease in Childhood. 1990; 65:939-941.
Martin, et al. A rapid and sensitive spectrophotometric method for the assay of chymotrypsin. Biol Chem. Feb. 1959;234(2):294-8.
Notice of Allowance dated Mar. 20, 2012 for U.S. Appl. No. 12/487,864.
Office Action dated Mar. 19, 2012 for U.S. Appl. No. 13/204,881.
Office Action dated Mar. 23, 2012 for U.S. Appl. No. 13/271,783.
Office Action dated Apr. 5, 2012 for U.S. Appl. No. 11/555,697.
Office Action dated Apr. 9, 2012 for U.S. Appl. No. 13/208,963.
Peters, et al. Treatment of alcoholic polyneuropathy with vitamin B complex: a randomised controlled trial. Alcohol Alcohol. Nov.-Dec. 2006;41(6):636-42. Epub Aug. 21, 2006.
Schumann. Medical, nutritional and technological properties of lactulose. An update. Eur J Nutr. Nov. 2002;41 Suppl 1:I17-25.
Sillanaukee, et al. Improved diagnostic classification of alcohol abusers by combining carbohydrate-deficient transferrin and gamma-glutamyltransferase. Clin Chem. Apr. 2001;47(4):681-5.
U.S. Appl. No. 13/481,087, filed May 25, 2012, Fallon.
U.S. Appl. No. 13/502,989, filed Apr. 19, 2012, Heil et al.
U.S. Appl. No. 13/503,844, filed Apr. 24, 2012, Fallon et al.
Dajcs, et al. Lysostaphin is effective in treating methicillin-resistant *Staphylococcus aureus* endophthalmitis in the rabbit. Curr Eye Res. Jun. 2001;22(6):451-7.
Kokai-Kun, et al. Lysostaphin as a treatment for systemic *Staphylococcus aureus* infection in a mouse model. J Antimicrob Chemother. Nov. 2007;60(5):1051-9. Epub Sep. 10, 2007.
Office action dated Jun. 13, 2012 for U.S. Appl. No. 12/493,122.
Dupiereux, et al. Creutzfeldt Jakob, Parkinson, lewy body dementia and Alzheimer diseases: from diagnosis to therapy. Cent Nerv Syst Agents Med Chem. Mar. 2009;9(1):2-11.
Notice of allowance dated Jul. 3, 2012 for U.S. Appl. No. 13/271,783.
Office action dated Jun. 27, 2012 for U.S. Appl. No. 12/493,147.
Office action dated Jul. 11, 2012 for U.S. Appl. No. 12/573,353.
Office action dated Jul. 18, 2012 for U.S. Appl. No. 12/047,818.
Wisniewski, et al. Therapeutic approaches for prion and Alzheimer's diseases. FEBS J. Aug. 2007;274(15):3784-98. Epub Jul. 6, 2007.
ABCnews. Changing Face of Autism: Numbers Rise as More Behaviors Included. ABCnews. Nov. 1, 2007.
Adams. "Summary of Defeat Autism Now! (DNN!) Oct. 2001 Conference," retrieved from the internet Dec. 18, 2008. http://puterakembara.org/rm/DAN2001.htm.

(56) References Cited

OTHER PUBLICATIONS

Advisory Action dated Jun. 3, 2008 for U.S. Appl. No. 10/681,018.
Aman, et al. Outcome measures for clinical drug trials in autism. CNS Spectr. Jan. 2004;9(1):36-47.
Amendment and Response dated Apr. 7, 2010 in Reply to Restriction Requirement dated Oct. 7, 2009 for U.S. Appl. No. 12/283,090.
Amendment and Response dated Jun. 30, 2010 to Restriction Requirement dated Jan. 13, 2010 for U.S. Appl. No. 12/487,868.
Amendment dated Oct. 20, 2008 in Reply to Notice Non-responsive Amendment dated Sep. 22, 2008 for U.S. Appl. No. 11/232,180.
Amendment dated Oct. 24, 2008 in Reply to Notice of Non-Responsive Amendment dated Sep. 25, 2008 for U.S. Appl. No. 11/555,697.
Amendment dated Oct. 28, 2009 in Reply to Final Office Action dated Apr. 28, 2009 for U.S. Appl. No. 10/681,018.
Amendment dated Nov. 13, 2009 in Reply to Final Office Action dated Jul. 27, 2004 for U.S. Appl. No. 09/990,909.
Amendment dated Nov. 17, 2007 in Reply to Restriction Requirement dated Oct. 17, 2007 for U.S. Appl. No. 11/555,697.
Amendment dated Dec. 12, 2007 in Reply to Office Action dated Aug. 8, 2007 for U.S. Appl. No. 11/213,382.
Amendment dated Dec. 7, 2007 in Reply to Office Action dated Aug. 7, 2007 for U.S. Appl. No. 10/681,018.
Amendment dated Feb. 2, 2004 in Reply to Office Action dated Jul. 29, 2003 for U.S. Appl. No. 09/990,909.
Amendment dated Feb. 29, 2008 in Reply to Notice of Non-Responsive Amendment dated Feb. 11, 2008 for U.S. Appl. No. 11/555,697.
Amendment dated Feb. 7, 2003 in Reply to Office Action dated Jul. 30, 2002 for U.S. Appl. No. 09/990,909.
Amendment dated Feb. 7, 2009 in Reply to Office Action dated Aug. 18, 2008 for U.S. Appl. No. 10/681,018.
Amendment dated Mar. 1, 2004 in Reply to Office Action dated Aug. 26, 2003 for U.S. Appl. No. 10/041,073.
Amendment dated Mar. 24, 2010 in Reply to Final Office Action dated Sep. 24, 2009 for U.S. Appl. No. 12/046,252.
Amendment dated Mar. 3, 2008 to Restriction Requirement dated Jan. 10, 2008 for U.S. Appl. No. 11/232,180.
Amendment dated Mar. 4, 2008 in Reply to Office Action dated Nov. 14, 2007 for U.S. Appl. No. 11/213,255.
Amendment dated May 18, 2007 in Reply to Office Action dated Dec. 22, 2006 for U.S. Appl. No. 10/681,018.
Amendment dated May 19, 2008 in Reply to Final Office Action dated Mar. 17, 2008 for U.S. Appl. No. 10/681,018.
Amendment dated May 27, 2009 in Reply to Final Office Action dated Feb. 27, 2009 for U.S. Appl. No. 11/555,697.
Amendment dated Jun. 15, 2009 in Reply to Final Office Action dated Mar. 13, 2009 for U.S. Appl. No. 11/232,180.
Amendment dated Jun. 8, 2007 in Reply to Restriction Requirement dated May 9, 2007 for U.S. Appl. No. 11/213,382.
Amendment dated Jun. 8, 2010 in Reply to Office Action dated Jan. 8, 2010 for U.S. Appl. No. 10/681,018.
Amendment dated Jul. 2, 2008 in Reply to Notice of Non-Compliant Amendment dated Jun. 2, 2008 for U.S. Appl. No. 12/046,252.
Amendment dated Aug. 19, 2009 in Reply to Notice Non-Compliant Amendment dated Jun. 19, 2009 for U.S. Appl. No. 11/232,180.
Amendment dated Aug. 21, 2008 in Reply to Office Action dated Apr. 21, 2008 for U.S. Appl. No. 11/232,180.
Amendment dated Aug. 28, 2008 in Reply to Office Action dated Mar. 28, 2008 for U.S. Appl. No. 11/555,697.
Amendment dated Sep. 24, 2007 in Reply to Restriction Requirement dated Jun. 22, 2007 for U.S. Appl. No. 11/213,255.
Amendment dated Sep. 25, 2008 in Reply to Final Office Action dated Jun. 25, 2008 for U.S. Appl. No. 11/213,255.
Amendment in Response dated May 23, 2003 to Restriction Requirement dated Apr. 23, 2003 for U.S. Appl. No. 09/990,909.
Ang, et al. Biological role and regulation of the universally conserved heat shock proteins. J Biol Chem. Dec. 25, 1991;266(36):24233-6.
APDA. Basic Information About Parkinson's Disease. Jul. 14, 2008.
Arribas, et al. A comparative study of the chymotrypsin-like activity of the rat liver multicatalytic proteinase and the ClpP from *Escherichia coli*. J Biol Chem. Oct. 5, 1993;268(28):21165-71.
Arrigo, et al. Expression of heat shock proteins during development in *Drosophila*. Results Probl Cell Differ. 1991;17:106-19.
Ash. Patient Information Guide—Understanding Hypertension. American Society of Hypertension. 2004. 1-7.
Ashwood, et al. Immune activation of peripheral blood and mucosal CD3+ lymphocyte cytokine profiles in children with autism and gastrointestinal symptoms. J Neuroimmunol. Dec. 19, 2005; 1-9.
Ashwood, et al. Intestinal lymphocyte populations in children with regressive autism: evidence for extensive mucosal immunopathology. J Clin Immunol. Nov. 2003;23(6):504-17.
Ashwood, et al. Spontaneous mucosal lymphocyte cytokine profiles in children with autism and gastrointestinal symptoms: mucosal immune activation and reduced counter regulatory interleukin-10. J Clin Immunol. Nov. 2004;24(6):664-73.
Austic. Development and adaptation of protein digestion. J Nutr. May 1985;115(5):686-97.
Autism Diagnosis. Autism Statistics. Www.autism-diagnosis.com/autism_statistics/autism_statistics.html. 2007.
Autism Society of America. Incidence Numbers from Other Countries. Jul. 14, 2008.
Awazuhara, et al. Antigenicity of the proteins in soy lecithin and soy oil in soybean allergy. Clin Exp Allergy. Dec. 1998;28(12):1559-64.
Axcan Pharma Inc. Cdn Prescribing Information on Viokase Pancrelipase, USP tablets, powder. 2000: 1-3.
Axelrod. Secretin Treatment for Gastrointestinal Dysmobility in Patients with Familial Dysautonomia. New York University School of Medicine, Grant Recipient awards, Mar.-May 2000. www.med.nyu.edu/ogars/awards/awards2000/page2.html.
Azilect et al. "Correlation between protein intake and daily levodopa dosage," Obtained from the internet May 2, 2007, http://www.azilect.eu/media/cnsnews/showitem.aspx?i=dlc603e4-3c61-4aal-a376-6e519a5a0f80.
Bailey, et al. Co-occurring conditions associated with FMR1 gene variations: findings from a national parent survey. Am J Med Genet A. Aug. 15, 2008;146A(16):2060-9.
Bakkaloglu, et al. Atopic features in early childhood autism. Eur J Paediatr Neurol. Nov. 2008;12(6):476-9.
Barlow. A comparison of the blood pressure, kidney volume and the pancreatic secretory response following the vein administration of various secretin preparations. Am J Phys. 1927;81:182-188.
Barnhart, et al. Symptomatic granular cell tumor involving the pituitary gland in a dog: a case report and review of the literature. Vet Pathol. May 2001;38(3):332-6.
Beilmann, et al. Neoexpression of the c-met/hepatocyte growth factor-scatter factor receptor gene in activated monocytes. Blood. Dec. 1, 1997;90(11):4450-8.
Bellanti, et al. Abnormalities of Th1 function in non-IgE food allergy, celiac disease, and ileal lymphonodular hyperplasia: a new relationship? Ann Allergy Asthma Immunol. Jun. 2003;90(6 Suppl 3):84-9.
Belmonte et al. Fragile X syndrome and autism at the intersection of genetic and neural networks. Nat Neurosci. Oct. 2006; 9(10):1221-5 (abstract only).
Berg, et al. Section 10.5 Many Enzymes Are Actived by Specific Proteolytic Cleavage. 2002.
Berg, et al. Section 9.1 Proteases: Facilitating a Difficult Reaction. 2002.
Berg, et al. Table of Contents. Biochemistry, 5th edition. 2002.
Birnbaum, et al. Heat shock or stress proteins and their role as autoantigens in multiple sclerosis. Ann N Y Acad Sci. Dec. 19, 1997;835:157-67. Abstract only.
Blackmer. Parkinson disease: treatment and medication. Mar. 10, 2009., retrieved from the internet on Sep. 15, 2009, http://emedicine.medscape.com/article/312519-treatment.
Blog. Acid Phosphatase Research (blog). Acid-phosphatase.blogspot.com. 2008.
Bode et al. Usefulness of a simple photometric determination of chymotrypsin activity in stools—results of a multicentre study. Clin Biochem. 1986; 19:333-37.
Boorom. Is this recently characterized gastrointestinal pathogen responsible for rising rates of inflammatory bowel disease (IBD) and IBD associated autism in Europe and the United States in the 1990s? Med Hypotheses. 2007;69(3):652-9.

(56) References Cited

OTHER PUBLICATIONS

Borowitz, et al. Use of pancreatic enzyme supplements for patients with cystic fibrosis in the context of fibrosing colonopathy. Consensus Committee. J Pediatr. Nov. 1995;127(5):681-4.
Boyd, et al. Positively charged amino acid residues can act as topogenic determinants in membrane proteins. Proc Natl Acad Sci U S A. Dec. 1989;86(23):9446-50.
Bradstreet, et al. Detection of Measles Virus Genomic RNA in Cerebrospinal Fluid of Children with Regressive Autism: a Report of Three Cases. J. Am Phys Surg. 2004; 9(2):38-45.
Brown. Background to Parkinson's Disease. biomed.brown.edu. Jul. 14, 2008.
Brudnak et al. Enzyme-based therapy for autism spectrum disorders—is it worth another look? Med Hypoth. 2002; 58:422-428.
Bruhat, et al. Amino acid limitation induces expression of CHOP, a CCAAT/enhancer binding protein-related gene, at both transcriptional and post-transcriptional levels. J Biol Chem. Jul. 11, 1997;272(28):17588-93.
Calderon-Garciduenas, et al. Immunotoxicity and environment: immunodysregulation and systemic inflammation in children. Toxicol Pathol. 2009;37(2): 161-9.
Campbell et al. A genetic variant that disrupts MET transcription is associated with autism. Proc Natl Acad Sci USA. 2006; 103(45):16834-16839.
Campbell, et al. Distinct genetic risk based on association of MET in families with co-occurring autism and gastrointestinal conditions. Pediatrics. Mar. 2009;123(3):1018-24.
Carlton. Autism and malnutrition: the milk connection. Retrieved from the internet on Feb. 18, 2008, http://www.mercola.com/2004/autism_malnutrition.htm.
Caronna, et al. Autism spectrum disorders: clinical and research frontiers. Arch Dis Child. Jun. 2008;93(6):518-23.
Carroccio, et al. Secondary impairment of pancreatic function as a cause of severe malabsorption in intestinal giardiasis: a case report. Am J Trop Med Hyg. Jun. 1997;56(6):599-602.
Carroccio, et al. Secretin-cerulein test and fecal chymotrypsin concentration in children with intestinal giardiasis. Int J Pancreatol. Oct. 1993;14(2):175-80.
Cassidy, et al. A new concept for the mechanism of action of chymotrypsin: the role of the low-barrier hydrogen bond. Biochemistry. Apr. 15, 1997;36(15):4576-84.
CDC. Attention-Deficit/Hyperactivity Disorder (ADHD). Www.cdc.org. 2005.
CDC. Autism Information Center/FAQs. Dept of Health and Human Services/CDC. Jan. 30, 2008.
CDC. High Blood Pressure. Division for Heart Disease Stroke Prevention. Jul. 15, 2008.
Chen, et al. Identification of two lysosomal membrane glycoproteins. J Cell Biol. Jul. 1985;101(1):85-95.
Chen, et al. Lysine 43 is trimethylated in subunit C from bovine mitochondrial ATP synthase and in storage bodies associated with batten disease. J Biol Chem. May 21, 2004;279(21):21883-7.
Cichoke, et al. The complete book of enzyme therapy. Penguin. 1998: 39, 42, 47, 50, and 53.
Claud, et a. Hypothesis: inappropriate colonization of the premature intestine can cause neonatal necrotizing enterocolitis. FASEB J. Jun. 2001;15(8):1398-403.
Concerta. ADHD Myths and Facts. ADHD Myths and Facts about medication, girls, and symptoms and causes. Concerta.net. Jul. 15, 2008.
Corring, et al. Development of digestive enzymes in the piglet from birth to 8 weeks. I. Pancreas and pancreatic enzymes. Nutr Metab. 1978;22(4):231-43.
Couet, et al. Identification of peptide and protein ligands for the caveolin-scaffolding domain. Implications for the interaction of caveolin with caveolae-associated proteins. J Biol Chem. Mar. 7, 1997;272(10):6525-33.
Coyle. Treating the Negative Symptoms of Schizophrenia: An Expert Interview with Joseph Coyle, MD. www.narsad.org/?q=node/438/latest-research. 2006.
Craig, et al. Heat shock proteins: molecular chaperones of protein biogenesis. Microbiol Rev. Jun. 1993;57(2):402-14.
Croonenberghs, et al. Peripheral markers of serotonergic and noradrenergic function in post-pubertal, caucasian males with autistic disorder. Neuropsychopharmacology. Mar. 2000;22(3):275-83.
Cruse et al. Illustrated dictionary of immunology. CRC Press, New York. 1995.
Cuervo, et al. Cathepsin A regulates chaperone-mediated autophagy through cleavage of the lysosomal receptor. EMBO J. Jan. 2, 2003;22(1):47-59.
Darman. An introduction to alternative medicine for psychiactric conditions. Oct. 22, 2007, retrieved on Sep. 18, 2009, http://web.archive.org/web/20071022104238/http://altp[therapies4bipolar.info/ortho/html.
Dawe, et al. The chakragati mouse: a mouse model for rapid in vivo screening of antipsychotic drug candidates. Biotechnol J. Nov. 2007;2(11):1344-52.
Dawn. Autism: the Latest Prevalence Rates in USA—Now 1 in 175. Disabled Women's Network Ontario. Dawn.thot.net/autism2.html. 2006.
Dawson lab. Research Projects in Synthetic Protein Chemistry. 2005; 1-2.
Delong. News on Parkinson's. The Dana Foundation. Jul. 14, 2008.
Diaz-Hernandez, et al. Neuronal induction of the immunoproteasome in Huntington's disease. J Neurosci. Dec. 17, 2003;23(37):11653-61.
Digestive Enzyme. retrieved from the internet Sep. 10, 2009, http://en.wikipedia.org/wiki/Digestive_enzyme.
Ding, et al. Proteasome inhibition in oxidative stress neurotoxicity: implications for heat shock proteins. J Neurochem. May 2001;77(4):1010-7.
Dobbs et al. Link between *Helicobacter pylori* infection and idiopathic parkinsonism. Medical Hypothsis. 200; 55(2):93-98.
Dockter et al. Determination of chymotrypsin in the feces by a new photometric method. Padiatr Padol. 1985; 20(3):257-265.
Edelson, et al. 3-Cyclohexene-1-glycine, an Isoleucine Antagonist. J. Am. Chem. Soc. 1958; 80(11):2698-2700.
Elphick, et al. Impaired luminal processing of human defensin-5 in Crohn's disease: persistence in a complex with chymotrypsinogen and trypsin. Am J Pathol. Mar. 2008;172(3):702-13.
Ethridge, et al. Acute pancreatitis results in induction of heat shock proteins 70 and 27 and heat shock factor-1. Pancreas. Oct. 2000;21(3):248-56.
Fafournoux, et al. Amino acid regulation of gene expression. Biochem J. Oct. 1, 2000;351(Pt 1):1-12.
Fallingborg, et al. Measurement of gastrointestinal pH and regional transit times in normal children. J Pediatr Gastroenterol Nutr. Aug. 1990;11(2):211-4.
Family Caregiver Alliance. Fact Sheet: Parkinson's Disease. Caregiver.org. Jul. 14, 2008.
Fernell, et al. No evidence for a clear link between active intestinal inflammation and autism based on analyses of faecal calprotectin and rectal nitric oxide. Acta Paediatr. Jul. 2007;96(7):1076-9.
Filipek et al. The screening and diagnosis of autistic spectrum disorders. J. of Autism and Dev Disorders. 1999; 29(6).
Final Office Action dated Nov. 9, 2010 for U.S. Appl. No. 09/990,909.
Final Office Action dated Feb. 14, 2011 for U.S. Appl. No. 12/049,613.
Final Office Action dated Feb. 27, 2009 for U.S. Appl. No. 11/555,697.
Final Office Action dated Mar. 13, 2009 for U.S. Appl. No. 11/232,180.
Final Office Action dated Mar. 17, 2008 for U.S. Appl. No. 10/681,018.
Final Office Action dated Apr. 28, 2009 for U.S. Appl. No. 10/681,018.
Final Office Action dated May 11, 2010 for U.S. Appl. No. 11/555,697.
Final Office Action dated Jun. 25, 2008 for U.S. Appl. No. 11/213,255.
Final Office Action dated Jul. 2, 2010 for U.S. Appl. No. 12/046,252.

(56) References Cited

OTHER PUBLICATIONS

Final Office Action dated Jul. 27, 2004 for U.S. Appl. No. 09/990,909.
Finegold et al. Gastrointestinal microflora studies in late-onset autism. Clinical Infectious Diseases. 2002; 35(1):S6-S15.
Fitzsimmons, et al. High-dose pancreatic-enzyme supplements and fibrosing colonopathy in children with cystic fibrosis. N Engl J Med. May 1, 1997;336(18):1283-9.
Frossard, et al. Both thermal and non-thermal stress protect against caerulein induced pancreatitis and prevent trypsinogen activation in the pancreas. Gut. Jan. 2002;50(1):78-83.
Frossard. Trypsin activation peptide (TAP) in acute pancreatitis: from pathophysiology to clinical usefulness. JOP. Mar. 2001;2(2):69-77.
Furlano, et al. Colonic CD8 and gamma delta T-cell infiltration with epithelial damage in children with autism. J Pediatr. Mar. 2001;138(3):366-72.
Garcia et al. Detection of *Giardia lamblia, entamoeba histolytica/ entamoeba dispar*, and *Cryptosporidium parvum* antigens in human fecal specimens using the triage parasite panel enzyme immunoassay. Am Soc for Microbiology. 2000; 38(9):3337-3340.
Gardner. Absorption of intact peptides: studies on transport of protein digests and dipeptides across rat small intestine in vitro. Q J Exp Physiol. Oct. 1982;67(4):629-37.
Garner Jr, et al. Porcine Pancreatic Lipase—A Glycoprotein. J Biol Chem. Jan. 25, 1972;247(2):561-5.
Gass, et al. Enhancement of dietary protein digestion by conjugated bile acids. Gastroenterology. Jul. 2007;133(1):16-23.
Generation Rescue. Autism and Vaccines Around the World: Vaccine Schedules, Autism Rates, and Under 5 Mortality. Apr. 1, 2009.
Giglio, et al. Failure to thrive: the earliest feature of cystic fibrosis in infants diagnosed by neonatal screening. Acta Paediatr. Nov. 1997;86(11):1162-5.
Goff, et al. Production of abnormal proteins in *E. coli* stimulates transcription of ion and other heat shock genes. Cell. Jun. 1985;41(2):587-95.
Gonzalez, et al. Endoscopical, histological and immunological characteristics of the digestive mucosa in autistic children with gastrointestinal symptoms. 2005; 1-7.
Green, et al. Amino-terminal polymorphisms of the human beta 2-adrenergic receptor impart distinct agonist-promoted regulatory properties. Biochemistry. Aug. 16, 1994;33(32):9414-9.
Gupta, et al. Th1- and Th2-like cytokines in CD4+ and CD8+ T cells in autism. J Neuroimmunol. May 1, 1998;85(1):106-9.
Hadjivassiliou, et al. Does cryptic gluten sensitivity play a part in neurological illness? Lancet. Feb. 10, 1996;347(8998):369-71.
Happe et al. The neuropsychology of autism. Brain. 1996; 119:1377-1400.
Happe et al. Time to give up on a simple explanation for autism. Nat Neurosci. Oct. 2006; 9(10):1218-20.
Health.com. Who is affected by Parkinson's disease. www.health.com. Jul. 14, 2008.
Heijerman, et al. Omeprazole enhances the efficacy of pancreatin (pancrease) in cystic fibrosis. Ann Intern Med. Feb. 1, 1991;114(3):200-1.
Hendren et al. Mechanistic biomarkers for autism treatment. Medical Hypotheses. 2009; 73:950-954.
Hitti. Allergy, celiac disease, and ileal lymphonodular. WebMD. 2005. 1-2.
Horvath et al. Improved social and language skills after secretin administration in patients with autistic spectrum disorders. Journal of the Association for Academic Minority Physicians. Jan. 1998; 9(1):9-15.
Horvath, et al. Autistic disorder and gastrointestinal disease. Curr Opin Pediatr. Oct. 2002;14(5):583-7.
Horvath, et al. Gastrointestinal abnormalities in children with autistic disorder. J Pediatr. Nov. 1999;135(5):559-63.
Hoshiko et al. The effect of the gastrointestinal hormones on colonic muscosal blood flow. Acta Medica Nagasakiensia. 1994; 39(4):125-130.
Houston. Autism—One Conference. May 2006. 1-83.
Hsiao, et al. The microbes of the intestine: an introduction to their metabolic and signaling capabilities. Endocrinol Metab Clin North Am. Dec. 2008;37(4):857-71.
Huang, et al. Apoptotic cell death in mouse models of GM2 gangliosidosis and observations on human Tay-Sachs and Sandhoff diseases. Hum Mol Genet. Oct. 1997;6(11):1879-85.
Huang, et al. Mapping of the human APOB gene to chromosome 2p and demonstration of a two-allele restriction fragment length polymorphism. Proc Natl Acad Sci U S A. Feb. 1986;83(3):644-8.
International search report and written opinion dated Jan. 18, 2011 for PCT/US2010/057341.
International search report and written opinion dated Feb. 15, 2011 for PCT/US2010/053484.
International search report and written opinion dated Mar. 2, 2010 for PCT/US2010/020253.
International search report and written opinion dated Jun. 9, 2010 for PCT/US2010/030895.
International search report and written opinion dated Sep. 25, 2009 for PCT/US2009/049374.
International search report and written opnion dated Mar. 5, 2010 for PCT/US2010/020259.
International search report dated Mar. 11, 2002 for PCT/US2001/25343.
International search report dated Jun. 29, 2001 for PCT/US2000/34000.
James, et al. Thimerosal neurotoxicity is associated with glutathione depletion: protection with glutathione precursors. Neurotoxicology. 2004; 26(1):1-8.
Jeffrey. Global burden of hypertension may reach 1.5 billion by 2025. Medscape Medical News. Jul. 14, 2008.
Juhl. Fibromyalgia and the serotonin pathway. Altern Med Rev. 1998; 3(5):367-375.
Jyonouchi, et al. Dysregulated innate immune responses in young children with autism spectrum disorders: their relationship to gastrointestinal symptoms and dietary intervention. Neuropsychobiology. 2005;51(2):77-85.
Jyonouchi, et al. Evaluation of an association between gastrointestinal symptoms and cytokine production against common dietary proteins in children with autism spectrum disorders. J Pediatr. May 2005;146(5):605-10.
Jyonouchi, et al. Proinflammatory and regulatory cytokine production associated with innate and adaptive immune responses in children with autism spectrum disorders and developmental regression. J Neuroimmunol. Nov. 1, 2001;120(1-2):170-9.
Kachrimanis, et al. Tensile strength and disintegration of tableted silicified microcrystalline cellulose: influences of interparticle bonding. J Pharm Sci. Jul. 2003;92(7): 1489-501.
Kaemmerer, et al. Effects of lipid peroxidation-related protein modifications on RPE lysosomal functions and POS phagocytosis. Invest Ophthalmol Vis Sci. Mar. 2007;48(3): 1342-7.
Kaminski, et al. Polymorphism of bovine beta-casein and its potential effect on human health. J Appl Genet. 2007;48(3):189-98.
Kaspar et al. New photometric assay for chymotrypsin in stool. Clinical Chemistry. 1984; 30(11):1753-1757.
Kearney, et al. Global burden of hypertension: analysis of worldwide data. Lancet. Jan. 15-21, 2005;365(9455):217-23. Abstract only.
Knivsberg, et al. A randomised, controlled study of dietary intervention in autistic syndromes. Nutr Neurosci. Sep. 2002;5(4):251-61.
Koller, et al. Falls and Parkinson's Disease (Abstract). Clin Neuropharmacol. 1989; 12(2):98-105.
Koplin, et al. Soy consumption is not a risk factor for peanut sensitization. J Allergy Clin Immunol. Jun. 2008;121(6):1455-9.
Koster et al. Evidence based medicine and extradigestive manifestations of *Helocobacter pylori*. Acta Gastro-Enterologica Belgica. 200; 63(4):388-392.
Kronenberg, et al. Folate deficiency induces neurodegeneration and brain dysfunction in mice lacking uracil DNA glycosylase. J Neurosci. Jul. 9, 2008;28(28):7219-30.
Kujoth, et al. Mitochondrial DNA mutations, oxidative stress, and apoptosis in mammalian aging. Science. Jul. 15, 2005;309(5733):481-4.
Larimore. How Common is ADHD? Facts About ADHD. Jul. 15, 2008.

(56) References Cited

OTHER PUBLICATIONS

Layer et al. Pancreatin enzyme replacement therapy. Current Gastroenterology Reports. 2001; 3:101-108.
Levy, et al. Relationship of dietary intake to gastrointestinal symptoms in children with autistic spectrum disorders. Biol Psychiatry. Feb. 15, 2007;61(4):492-7.
Leyfer, et al. Comorbid psychiatric disorders in children with autism: interview development and rates of disorders. J Autism Dev Disord. Oct. 2006;36(7):849-61.
Lieberman. Pharmaceutical Dosage Forms. vol. 2: Disperse Systems. New York Marcel Dekker, Inc. 1996; 243-258.
Lipase 30, Technical Data sheet, 1 page, Scientific Protein Laboratories LLC Jun. 13, 2005.
Lloyd. Lysosome membrane permeability: implications for drug delivery. Adv Drug Deliv Rev. Mar. 30, 2000;41(2):189-200.
Loh, et al. Highly tolerated amino acid substitutions increase the fidelity of *Escherichia coli* DNA polymerase I. J Biol Chem. Apr. 20, 2007;282(16):12201-9.
Lord, et al. Diagnostic Instruments in Autistic Spectrum Disorders. info.med.yale.edu. 2005; 11:730-771.
Luedtke, et al. Cathepsin A is expressed in a cell- and region-specific manner in the testis and epididymis and is not regulated by testicular or pituitary factors. J Histochem Cytochem. Aug. 2000;48(8):1131-46.
MacFabe, et al. Neurobiological effects of intraventricular propionic acid in rats: possible role of short chain fatty acids on the pathogenesis and characteristics of autism spectrum disorders. Behav Brain Res. 2006;176(1):149-69.
MacReady. Parkinson's Diseasne Treatment: what you should know. Retrieved from the internet on Sep. 15, 2009, http://www.everydayhealth.com/parkinsons-disease-treatment-overview.aspx.
Mannino, et al. Surveillance for asthma—United States, 1960-1995. MMWR CDC Surveill Summ. Apr. 24, 1998;47(1):1-27.
Marczewska et al. Protein intake in parkinsonian using the EPIC food frequency questionnaire. Mov Diord. Aug. 2006; 21(8):1229-1231.
Marlicz et al. Determination of chymotrypsin in the stool in the diagnosis of chronic pancreatitis. Wiadomosci lekarskie. 1988; 41(11):704-707. (in Polish with English abstract/summary).
Marsh. Neuropsychiatric aspects of parkinson's disease. Psychosomatics. 2000; 41(1):15-23.
Maurin, et al. Cellular adaptation to amino acid availability: mechanisms involved in the regulation of gene expression. 2006; 319-326.
Mayo Clinic Staff. Autism. Retrieved from internet Mar. 10, 2008, http://www.mayoclinic.com/health/autism/DS00348DSECTION=2.
Mayo Clinic Staff. Bipolar disorder. Jan. 4, 2008, http://www.mayoclinic.com/health/bipolardisorder/DS00356/DSECTION=symptoms.
Mayo Clinic Staff. Obsessive-compulsive disorder. Dec. 21, 2006. http://www.preferredalternatives.org/lat/WellnessLibrary/anxiety&PanicDisorders/Obsessive-CompulsiveDisorder/Obsessive-CompulsiveDisorder-Mayoclinic.pdf.
Mayo Clinic Staff. Oppositional defiant disorder. Dec. 19, 2007, http://www.mayoclinic.com/health/oppositional-defiant-disorder/DS00630/DSECTION=symptoms.
McAlonan, et al. Brain anatomy and sensorimotor gating in Asperger's syndrome. ain. Jul. 2002;125(Pt 7):1594-606.
McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.
McCracken, et al. Risperidone in children with autism and serious behavioral problems. N Engl J Med. Aug. 1, 2002;347(5):314-21.
Medsafe. Data sheet for alpha-lactose, Jul. 21, 1999, http://www.medsafe.govt.nz/Profs/Datasheet/a/Alphalactulosesyrup.htm.
Medsafe. Burden of Hypertension in the United States Greater Than Ever. www.medscape.com. Jul. 14, 2008.
Melmed, et al. Metabolic markers and gastrointestinal symptoms in children with autism and related disorders. J Pediatr Gast Nutr. 2000; 31:S31-S32.

Merck. Autism, Merck manual online medical library home addition, retrieved from the internet Mar. 10, 2008, http://www.mercl.com/mmhge/sec23/ch286/ch286b.html.
MeSH browser. "Child Development Disorders, Pervasive," and "Attention Deficit and Disruptive Behavior Disorders," National Library of medicine. 2001, http://www.nlm.nih.gov/mesh/2002/Mbrowser.html.
Michell et al. Biomarkers and parkinson's disease. Brain. 2004; 127(8):1693-1705.
Minamino, et al. Vascular cell senescence: contribution to atherosclerosis. Circ Res. Jan. 5, 2007;100(1):15-26.
Ming, et al. Autism spectrum disorders: concurrent clinical disorders. J Child Neurol. Jan. 2008;23(1):6-13.
Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.
Mononen, et al. Aspartylglycosaminuria in the Finnish population: identification of two point mutations in the heavy chain of glycoasparaginase. Proc Natl Acad Sci U S A. Apr. 1, 1991;88(7):2941-5.
Munasinghe et al. Digestive enzyme supplementation for autism spectrum disorders: a double-blind randomized controlled trial. J Autism Dev Disord. Sep. 2010;40(9):1131-8. Abstract only.
Nachaegari et al. Coprocessed excipients for solid dosage forms. Pharmaceutical Technology. 2004; p. 52, 54, 56, 58, 60, 64.
Nagamoto. Jacobson: Psychiatric Secrets, 2nd ed. 2001.
Neuer, et al. The role of heat shock proteins in reproduction. Hum Reprod Update. Mar.-Apr. 2000;6(2):149-59.
Nevo et al. Acute immune polyneuropathies: correlations of serum antibodies to *Campylobacter jejuni* and *Helicobacter pylori* with anti-gm antibodies and clinical patterns of disease. J of Inf diseases. 1997; 175(S2):S154-6.
Newhorizons. ADD/ADHD: New Perspectives on Attentional Priority Disorders. New Horizons for Learning. Jul. 15, 2008.
NIH. National Institutes of Health. National Diabetes Statistics 2007. diabetes.niddk.nih.gov. Jun. 1, 2008.
NINDS Dysautonimia Information Page. retrieved from the internet Sep. 10, 2009, http://www.ninds.nih.gov/disorders/dysautonomia/dysautonomia.htm.
NINDS Guillain-Barre Syndrome Information Page. retrieved from the internet Sep. 15, 2009, http://www.ninds.nih.gov/disorders/gbs/gbs.htm.
Notice Non-Compliant Amendment dated Jun. 19, 2009 for U.S. Appl. No. 11/232,180.
Notice Non-responsive Amendment dated Sep. 22, 2008 for U.S. Appl. No. 11/232,180.
Notice of Allowance dated Apr. 15, 2011 for U.S. Appl. No. 12/487,868.
Notice of Allowance dated Apr. 29, 2011 for U.S. Appl. No. 12/046,402.
Notice of Allowance dated May 23, 2011 for U.S. Appl. No. 09/990,909.
Notice of Allowance dated Jun. 27, 2011 for U.S. Appl. No. 12/238,415.
Notice of Allowance dated Jun. 28, 2011 for U.S. Appl. No. 12/487,868.
Notice of Allowance dated Jun. 30, 2011 for U.S. Appl. No. 09/990,909.
Notice of Allowance dated Jul. 8, 2011 for U.S. Appl. No. 12/046,402.
Notice of Non-Complaint Amendment dated Jun. 2, 2008 for U.S. Appl. No. 12/046,252.
Notice of Non-Compliant Amendment dated Apr. 27, 2010 for U.S. Appl. No. 12/283,090.
Notice of Non-Compliant Amendment dated May 7, 2007 for U.S. Appl. No. 11/213,255.
Notice of Non-Responsive Amendment dated Feb. 11, 2008 for U.S. Appl. No. 11/555,697.
Notice of Non-Responsive Amendment dated Sep. 25, 2008 for U.S. Appl. No. 11/555,697.
O'Connell. Hypertension Guide. cmbi.bjmu.edu. Jul. 14, 2008.
Office Action dated Mar. 29, 2011 for U.S. Appl. No. 12/054,343.

(56) References Cited

OTHER PUBLICATIONS

Office Action dated Mar. 30, 2011 for U.S. Appl. No. 12/786,739.
Office Action dated Apr. 27, 2011 for U.S. Appl. No. 10/681,018.
Office Action dated Apr. 28, 2011 for U.S. Appl. No. 12/283,090.
Office Action dated May 24, 2011 for U.S. Appl. No. 12/487,864.
Office action dated Jun. 29, 2011 for U.S. Appl. No. 11/555,697.
Office Action dated Jan. 21, 2011 for U.S. Appl. No. 12/386,051.
Office Action dated Jan. 29, 2002 for U.S. Appl. No. 09/707,395.
Office Action dated Jan. 8, 2010 for U.S. Appl. No. 10/681,018.
Office Action dated Oct. 1, 2001 for U.S. Appl. No. 09/466,559.
Office Action dated Oct. 5, 2010 for U.S. Appl. No. 12/046,402.
Office Action dated Nov. 14, 2007 for U.S. Appl. No. 11/213,255.
Office Action dated Nov. 15, 2010 for U.S. Appl. No. 12/238,415.
Office Action dated Nov. 25, 2009 for U.S. Appl. No. 11/232,180.
Office Action dated Nov. 26, 2001 for U.S. Appl. No. 09/466,559.
Office Action dated Dec. 19, 2005 for U.S. Appl. No. 10/730,567.
Office Action dated Dec. 22, 2006 for U.S. Appl. No. 10/681,018.
Office Action dated Mar. 18, 2008 for U.S. Appl. No. 11/468,379.
Office Action dated Mar. 25, 2008 for U.S. Appl. No. 11/213,382.
Office Action dated Mar. 28, 2008 for U.S. Appl. No. 11/555,697.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jun. 30, 2004 for U.S. Appl. No. 10/730,567.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.
Office Action dated Jul. 30, 2002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.
Office Action dated Aug. 25, 2010 for U.S. Appl. No. 12/487,868.
Office Action dated Aug. 26, 2003 for U.S. Appl. No. 10/041,073.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Sep. 22, 2004 for U.S. Appl. No. 10/730,567.
Office Action dated Sep. 24, 2009 for U.S. Appl. No. 12/046,252.
Owley, et al. Multisite, double-blind, placebo-controlled trial of porcine secretin in autism. J Am Acad Child Adolesc Psychiatry. Nov. 2001;40(11):1293-9.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Parisi et al. Evaluation of new rapid commercial enzyme immunoassay for detection of crytosporidium oocysts in untreated stool specimens. J Clin Microbiol. 1995; 33(7):1963-1965.
Park, et al. Increased apoptosis in cystinotic fibroblasts and renal proximal tubule epithelial cells results from cysteinylation of protein kinase Cdelta. J Am Soc Nephrol. Nov. 2006;17(11):3167-75.
Parkinsons Disease Foundation. Parkinson's Disease Q&A. 2007. 1-44.
Parkinsons Disease Foundation. Ten Frequently-Asked Questions about Parkinson's Disease. 2006.
Parracho, et al. Differences between the gut microflora of children with autistic spectrum disorders and that of healthy children. J Med Microbiol. Oct. 2005;54(Pt 10):987-91.
PDTalks. Motivational & Inspirational Speaking From a Parkinson's Patient Perspective. pdtalks.com/Parkinson_s_Disease.html. Jul. 14, 2008.
Perman et al. Role of ph in production of hydrogen from carbohydrates by colonic bacterial flora. J Clin Invest. 1981; 24(4):684-685.
Persico, et al. Searching for ways out of the autism maze: genetic, epigenetic and environmental clues. Trends Neurosci. Jul. 2006;29(7):349-58.
Peters et al. Prevalence of enteric parasites in homosexual patients attending an outpatient clinic. J of Clin Micro. 1986; 24(4):684-685.
Polanczyk, et al. The worldwide prevalence of ADHD: a systematic review and metaregression analysis. Am J Psychiatry. Jun. 2007;164(6):942-8.
Ponsky, et al. Alterations in gastrointestinal physiology after Roux-en-Y gastric bypass. J Am Coll Surg. Jul. 2005;201(1):125-31.
Preliminary Amendment dated May 18, 2009 for U.S. Appl. No. 12/046,252.
Puri, et al. Isolated segmental duodenal ganglionosis. Indian Journal of Radiology and Imaging. 2000; 153-154.
Raimondo, et al. Rapid endoscopic secretin simulation test and discrimination of chronic pancreatisis and pancreatic cancer from disease controls. Clin Gastroenterol Hepatol. Sep. 2003;1(5):397-403.
Rakonczay, et al. A new severe acute necrotizing pancreatitis model induced by L-ornithine in rats. Crit Care Med. Jul. 2008;36(7):2117-27.
Ray, et al. Growth factor regulation of enterocyte nutrient transport during intestinal adaptation. Am J Surg. Apr. 2002;183(4):361-71.
Remtulla et al. Stool chymotrypsin activity measured by a spectrophotometric procedure to identify pancreat disease in infants. Clinical Biochemistry. Dec. 1986; 19:341-342.
Response dated Oct. 3, 2006 to Restriction Requirement dated Sep. 12, 2006 for U.S. Appl. No. 10/681,018.
Response dated Apr. 29, 2010 to Notice of Non-Compliant Amendment dated Apr. 27, 2010 for U.S. Appl. No. 12/283,090.
Response dated Jun. 17, 2008 to Advisory Action dated Jun. 3, 2008 for U.S. Appl. No. 10/681,018.
Response dated Jun. 24, 2002 to Restriction Requirement dated May 22, 2002 for U.S. Appl. No. 09/990,909.
Response dated Jun. 7, 2007 to Notice of Non-Compliant Amendment dated May 7, 2007 for U.S. Appl. No. 11/213,255.
Restriction Requirement dated Jan. 10, 2008 for U.S. Appl. No. 11/232,180.
Restriction Requirement dated Jan. 13, 2010 for U.S. Appl. No. 12/487,868.
Restriction Requirement dated Oct. 17, 2007 for U.S. Appl. No. 11/555,697.
Restriction Requirement dated Oct. 7, 2009 for U.S. Appl. No. 12/283,090.
Restriction Requirement dated Dec. 10, 2009 for U.S. Appl. No. 11/533,818.
Restriction Requirement dated Apr. 23, 2003 for U.S. Appl. No. 09/990,909.
Restriction Requirement dated May 22, 2002 for U.S. Appl. No. 09/990,909.
Restriction Requirement dated May 9, 2007 for U.S. Appl. No. 11/213,382.
Restriction Requirement dated Jun. 22, 2007 for U.S. Appl. No. 11/213,255.
Restriction Requirement dated Sep. 12, 2006 for U.S. Appl. No. 10/681,018.
Revolution health. Enzyme therapy. revolutionhealth.com/drugs-treatments/enzyme-therapy. Sep. 2, 2008.
Rider, et al. Perspective of biochemical research in the neuronal ceroid-lipofuscinosis. Am J Med Genet. Feb. 15, 1992;42(4):519-24.
Rogers. No more heartburn: Stop the pain in 30 days—naturally. 2000; 172.
Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.
Rubenstein, et al. Model of autism: increased ratio of excitation/inhibition in key neural systems. Genes Brain Behav. Oct. 2003;2(5):255-67.
Sabra, et al. Linkage of ileal-lymphoid-nodular hyperplasia (ILNH), food allergy and CNS developmental: evidence for a non-IgE association. Ann Aller Asth Immunol. 1999; 82(1):81.
Sahelian. Enzymes. raysahelian.com/enzymes.html. Sep. 2, 2008.
Sandler et al. Short term benefit from oral vancomycin treatment of regressive-onset autism. J of Child Neuro. 2000; 15(7):42-435.

(56) References Cited

OTHER PUBLICATIONS

Sandler, et al. Lack of benefit of a single dose of synthetic human secretin in the treatment of autism and pervasive developmental disorder. N Engl J Med. Dec. 9, 1999;341(24): 1801-6.
Schafer, et al. Stress kinases and heat shock proteins in the pancreas: possible roles in normal function and disease. J Gastroenterol. 2000;35(1):1-9.
Schiller. Review article: the therapy of constipation. Aliment Pharmacol Ther. 2001; 15:749-763.
Schneider, et al. Oral human immunoglobulin for children with autism and gastrointestinal dysfunction: a prospective, open-label study. J Autism Dev Disord. Nov. 2006;36(8):1053-64.
Schreck et al. Food preferences and factors influecing food selectivity for children with autism spectrum disorders. Res Develop Disabil. 2006; 27:353-363.
Schreck, et al. Food preferences and factors influencing food selectivity for children with autism spectrum disorders. Res Dev Disabil. 2005;27(4):353-63.
Seneca et al. Enhancement of brain l-dopa concetration with a-chymotrypsm. J American Geriatrics Society. 1973; 256-258.
Settembre, et al. A block of autophagy in lysosomal storage disorders. Hum Mol Genet. Jan. 1, 2008;17(1):119-29.
Shadel. Expression and maintenance of mitochondrial DNA: new insights into human disease pathology. Am J Pathol. Jun. 2008;172(6):1445-56.
Shaul. Report to the Chairman and Ranking Minority Member, Subcommittee on Human Rights and Wellness, Committee on Government Reform, House of Representatives. GEO. Jan. 2005. 1-40.
Sherwood et al. A new class of high-functionality excipients: silicified microcrystalline cellulose. Pharm Tech. 1998; 22(10):78-88.
Sherwood, et al. Activation of trypsinogen in large endocytic vacuoles of pancreatic acinar cells. Proc Natl Acad Sci U S A. Mar. 27, 2007;104(13):5674-9.
Shimabukuro, et al. Medical expenditures for children with an autism spectrum disorder in a privately insured population. J Autism Dev Disord. 2007;38(3):546-52.
Shpacovitch, et al. Protease-activated receptors: novel PARtners in innate immunity. Trends Immunol. Dec. 2007;28(12):541-50.
Shpacovitch, et al. Role of protease-activated receptors in inflammatory responses, innate and adaptive immunity. J Leukoc Biol. Jun. 2008;83(6):1309-22.
Simonoff, et al. Psychiatric disorders in children with autism spectrum disorders: prevalence, comorbidity, and associated factors in a population-derived sample. J Am Acad Child Adolesc Psychiatry. Aug. 2008;47(8):921-9.
Singh, et al. Plasma increase of interleukin-12 and interferon-gamma. Pathological significance in autism. J Neuroimmunol. May 1996;66(1-2):143-5.
Skeels et al. Crytosporidium infection in Oregon public health clinic patients 1985-88: the value of statewide laboratory surveillance. AJPH. 1990; 80(3):305-308.
Statemaster. Number of Children with Autism (most recent w/graph) by state. Statemaster.com Jul. 14, 2008.
Statemaster. Number of Children with Autism (most recent) by state. Statemaster.com Jul. 14, 2008.
Statemaster. Number of Children with Autism (per capita)(most recent) by state. Statemaster.com Jul. 14, 2008.
Stein, et a. Nitrogen Metabolism in normal and hyperkinetic boys. Am J Clin Nutr. 1984; 39:520-524.
Stein, et al. Nitrogen metabolism in normal and hyperkinetic boys. Am J Clin Nutr. Apr. 1984;39(4):520-4.
Steinherz, et al. Patterns of amino acid efflux from isolated normal and cystinotic human leucocyte lysosomes. J Biol Chem. Jun. 10, 1982;257(11):6041-9.
Stoll, et al. Enteral nutrient intake level determines intestinal protein synthesis and accretion rates in neonatal pigs. Am J Physiol Gastrointest Liver Physiol. Aug. 2000;279(2):G288-94.
Stott, et al. MMR and Autism in Perspective: the Denmark Story. J. Am Phys Surg. 2004; 9(3):89-91.

Strader, et al. Publication Structural basis of β-adrenergic receptor function. FASEB J. May 1989;3(7):1825-32.
Sturmey. Secretin is an ineffective treatment for pervasive developmental disabilities: a review of 15 double-blind randomized controlled trials. Res Dev Disabil. Jan.-Feb. 2005;26(1):87-97.
Supplemental Amendment and Response dated Jun. 8, 2010 to Restriction Requirement dated Oct. 7, 2009 for U.S. Appl. No. 12/283,090.
Tager-Flusberg, et al. Language disorders: autism and other pervasive developmental disorders. Pediatr Clin North Am. Jun. 2007;54(3):469-81, vi.
Terrie, et al. Understanding Pancreatic Enzyme Products. Dec. 15, 2008.
The Alzheimer's Association. Basics of Alzheimer's Disease. 2005, http://www.alz.org/national/documents/brochure_Basicsofalz_low/pdf.
Thomas, et al. Defective protein folding as a basis of human disease. Trends Biochem Sci. Nov. 1995;20(11):456-9.
Tiedermann, et al. Identification of a potent natural triterpenoid inhibitor of proteosome chymotrypsin-like activity and NF-kappaB with antimyeloma activity in vitro and in vivo. Blood. Apr. 23, 2009;113(17):4027-37.
Torrente, et al. Focal-enhanced gastritis in regressive autism with features distinct from Crohn's and *Helicobacter pylori* gastritis. Am J Gastroenterol. Apr. 2004;99(4):598-605.
Torrente, et al. Small intestinal enteropathy with epithelial IgG and complement deposition in children with regressive autism. Mol Psychiatry. 2002;7(4):375-82, 334.
Trauner, et al. Specific cognitive deficits in young children with cystinosis: evidence for an early effect of the cystinosin gene on neural function. J Pediatr. Aug. 2007;151(2):192-6.
Tsan, et al. Heat shock proteins and immune system. J Leukoc Biol. Jun. 2009;85(6):905-10.
Tsang et al. Extragastroduodenal conditions associated with *Heliobacter pylori* infection. Hong Kong Medical Journal. 1999; 5(2):169-174.
Uhlmann, et al. Potential viral pathogenic mechanism for new variant inflammatory bowel disease. Mol Pathol. Apr. 2002;55(2):84-90.
Unis, et al. A randomized, double-blind, placebo-controlled trial of porcine versus synthetic secretin for reducing symptoms of autism. J Am Acad Child Adolesc Psychiatry. Nov. 2002;41(11):1315-21.
UPI. Number of autistic Calif. students triples. United Press International. Jul. 12, 2008.
USP (32)—NF(27) 2009, Pancreatin, V.3, pp. 3194-3195.
Valicenti-McDermott, et al. Frequency of gastrointestinal symptoms in children with autistic spectrum disorders and association with family history of autoimmune disease. J Dev Behav Pediatr. Apr. 2006;27(2 Suppl):S128-36.
Vargas, et al. Neuroglial activation and neuroinflammation in the brain of patients with autism. Ann Neurol. Jan. 2005;57(1):67-81.
Vellard. The enzyme as drug: application of enzymes as pharmaceuticals. Curr Opin Biotechnol. Aug. 2003;14(4):444-50.
Vilanova, et al. Preparative isolation of the two forms of pig pancreatic pro-(carboxypeptidase A) and their monomeric carboxypeptidases A. Biochem J. Aug. 1, 1985;229(3):605-9.
Vojdani, et al. Antibodies against CNS antigens in autism: Possible cross-reaction with dietary proteins and infectious agent antigens. Neuropsychiatric Disorders and Infection. 2004; 19:171-186.
Vojdani, et al. Heat shock protein and gliadin peptide promote development of peptidase antibodies in children with autism and patients with autoimmune disease. Clin Diagn Lab Immunol. May 2004;11(3):515-24.
Vojdani, et al Immune response to dietary proteins, gliadin and cerebellar peptides in children with autism. Nutr Neurosci. Jun. 2004;7(3):151-61.
Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (Part 1) Dec. 1999; 38(12 Suppl):32S-54S.
Volkmar, et al. Practice Parameters for the Assessment and Treatment of Children, Adolescents, and Adults with Autism and other Perva-

(56) References Cited

OTHER PUBLICATIONS sive Developmental Disorders. American Academy of Child and Adolescent Psychiatry. J Am Acad Child Adolesc Psychiatry. (Part 2) Dec. 1999;38(12):1611-6.
Wakefield, et al. Enterocolitis in children with developmental disorders. Am J Gastroenterol. Sep. 2000;95(9):2285-95.
Wakefield, et al. Ileal-lymphoid-nodular hyperplasia, non-specific colitis, and pervasive developmental disorder in children. Lancet. Feb. 28, 1998;351(9103):637-41.
Wakefield, et al. Review article: the concept of entero-colonic encephalopathy, autism and opioid receptor ligands. Aliment Pharmacol Ther. Apr. 2002;16(4):663-74.
Wakefield, et al. The significance of ileo-colonic lymphoid nodular hyperplasia in children with autistic spectrum disorder. Eur J Gastroenterol Hepatol. Aug. 2005;17(8):827-36.
Wakefield. Autistic enterocolitis: is it a histopathological entity? Histopathology. 2006; 1-5.
Wakefield. Enterocolitis, Autism, and Measles Virus. Consensus in Child Neurology: Biological Bases and Clinical Perspectives in Autism. 2002; 74-81.
Wakefield. The gut-brain axis in childhood developmental disorders. J Pediatr Gastroenterol Nutr. May-Jun. 2002;34 Suppl 1:S14-7.
Walsh, et al. Heat shock and the role of the HSPs during neural plate induction in early mammalian CNS and brain development. Cell Mol Life Sci. Feb. 1997;53(2):198-211.
Wang, et al. Activation of Ras/Erk pathway by a novel MET-interacting protein RanBPM. J Biol Chem. Sep. 27, 2002;277(39):36216-22.
Weintraub, et al. Morphometric studies of pancreatic acinar granule formation in NCTR-Balb/c mice. J Cell Sci. May 1992;102 ( Pt 1):141-7.
Welch, et al. Brain effects of chronic IBD in areas abnormal in autism and treatment by single neuropeptides secretin and oxytocin. J Mol Neurosci. 2004;25(3):259-74.
Wender et al. Prevalence of attention deficit disorder, residual type, and other psychiatric disorders in patients with irritable colon syndrome. Am J Psychiatry. 1983; 140(12):1579-82 Abstract only.
Whitehouse. Fact Sheet: Combating Autism Act of 2006. www.whitehouse.gov. Dec. 19, 2006.
Williams, et al. Eating habits of children with autism. Pediatr Nurs. May-Jun. 2000;26(3):259-64.
Witmer. ADD and ADHD Statistics—CDC Report Looks at Attention-Deficit/Hyperactivity Disorder. About.com—Parenting of Adolescents. Jul. 15, 2008.
Wohlman et al. Enhancement of drug activity by chymotrypsin, penicillin penetration into granulomatous sesions and inflammatory fluids. Cellular and Molecular Life Sciences. 1969; 25(9):953-954.
Woodward et al. Ischaemic enterocolitis complicating aidiopathic dysatuonomia. Gut. 1998; 43:285-287.
Yahoo!.com. Who is affected by Parkinson's disease. Yahoo! Health. Jul. 14, 2008.
Yazbak. Autism in the United States: a perspective. Journal of American Physicians and Surgeons. 2003;8:103-107.
Youngberg, et al. Comparison of gastrointestinal pH in cystic fibrosis and healthy subjects. Dig Dis Sci. May 1987;32(5):472-80.
Yuan, et al.. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. EMBO J. Sep. 15, 1997;16(18):5483-90.
Zhang et al. Lactulose-mannitol intestinal permeability test in children with diarrhea caused by rotavirus abd *Cryptosporidium*. J of Pediatric Gastro & Nutrition. 2000; 31(1):16-21.
Derwent. Abstract for RU 2286785 Nov. 10, 2006. Downloaded from the Derwent file Jul. 13, 2011.
Notice of Allowance dated Aug. 8, 2011 for U.S. Appl. No. 12/426,794.
Notice of Allowance dated Sep. 20, 2011 for U.S. Appl. No. 12/283,090.
Smith, et al. Fecal chymotrypsin and trypsin determinations. Canadian Medical Association Journal. 1971; 104(8):691-4 and 697.
U.S. Appl. No. 13/144,286, filed Jul. 12, 2011, Fallon et al.
U.S. Appl. No. 13/144,290, filed Jul. 12, 2011, Fallon et al.
U.S. Appl. No. 13/204,881, filed Aug. 8, 2011, Fallon et al.
U.S. Appl. No. 13/208,963, filed Aug. 12, 2011, Fallon.
Liyanage, et al. Bioavailability of iron from micro-encapsulated iron sprinkle supplement. Food and Nutrition bulletin. 2002; 23 (3): 133-137.
Office action dated Oct. 19, 2011 for U.S. Appl. No. 12/386,051.
Final Office Action dated Nov. 8, 2011 for U.S. Appl. No. 12/054,343.
Final Office Action dated Nov. 8, 2011 for U.S. Appl. No. 12/786,739.
TheFreeDictionary. Term Sprinkles. www.thefreedictionary.com. Accessed Nov. 2, 2011. 1 page.
U.S. Appl. No. 13/562,999, filed Jul. 31, 2012, Fallon.
U.S. Appl. No. 13/705,763, filed Dec. 5, 2012, Fallon et al.
Bowers. Secretions of the pancreas. Jul. 5, 2006. Accessed online at www.vivo.colostate.edu/hbooks/pathphys/digestion/pancreas/exocrine.html, Exocrine.
Office action dated Aug. 13, 2012 for U.S. Appl. No. 13/208,963.
Office action dated Sep. 13, 2012 for U.S. Appl. No. 13/481,087.
Office action dated Oct. 10, 2012 for U.S. Appl. No. 13/204,881.
Office action dated Oct. 25, 2012 for U.S. Appl. No. 13/144,286.
Office action dated Oct. 25, 2012 for U.S. Appl. No. 13/144,290.
Office action dated Dec. 6, 2012 for U.S. Appl. No. 13/002,136.
Walsh, et al. Reduced violent behavior following chemical therapy. Physiology and behavior. 2004; 82:835-839.
Carroccio, et al. Pancreatic enzyme therapy in childhood celiac disease. A double-blind prospective randomized study. Dig Dis Sci. Dec. 1995;40(12):2555-60.
Creon. Full prescribing information. Last edited Mar. 2013. Abbvie Inc 2012. www.rxabbvie.com/pdf/creon_PI.pdf.
Eaves, et al. The criterion-related validity of the Childhood Autism Rating Scale and the Autism Behavior Checklist. J Abnorm Child Psychol. Oct. 1993;21(5):481-91. abstract only.
Evans, et al. Pancreatic insufficiency in adult celiac disease: do patients require long-term enzyme supplementation? Dig Dis Sci. Oct. 2010;55(10):2999-3004. doi: 10.1007/s10620-010-1261-y. Epub May 11, 2010.
International search report and written opinion dated Aug. 27, 2013 for PCT/US2013/043444.
King, et al. Effects of bacterial microflora of the lower digestive tract of free-range waterfowl on influenza virus activation. Appl Environ Microbiol. Jun. 2011;77(12):4119-25. doi: 10.1128/AEM.02578-10. Epub Apr. 29, 2011.
Leeds, et al. Is exocrine pancreatic insufficiency in adult coeliac disease a cause of persisting symptoms? Aliment Pharmacol Ther. Feb. 1, 2007;25(3):265-71.
Notice of allowance dated Aug. 19, 2013 for U.S. Appl. No. 13/208,963.
Notice of allowance dated Aug. 30, 2013 for U.S. Appl. No. 12/047,818.
Office action dated Aug. 14, 2013 for U.S. Appl. No. 13/448,061.
Office action dated Aug. 28, 2013 for U.S. Appl. No. 13/313,629.
Office action dated Sep. 9, 2013 for U.S. Appl. No. 13/502,989.
Pancrease. Patient information leaflet. Pancrease HL Capsules. Last updated Apr. 30, 2013. Janssen-cilag Ltd. www.medicines.org.uk/EMC/medicine/7326.
U.S. Appl. No. 14/037,652, filed Sep. 26, 2013, Fallon.
U.S. Appl. No. 14/037,696, filed Sep. 26, 2013, Fallon.
U.S. Appl. No. 14/007,793, filed Sep. 26, 2013, Fallon.
Notice of allowance dated Oct. 29, 2013 for U.S. Appl. No. 13/204,881.
Office action dated Oct. 24, 2013 for U.S. Appl. No. 13/313,708.
Office action dated Aug. 2, 2013 for U.S. Appl. No. 12/535,676.
Xu. Pancreatin therapy in chronic pancreatitis. Clin J Dig, May 2005; 25(5):313-315. (in Chinese with English translation).
U.S. Appl. No. 13/733,873, filed Jan. 3, 2012, Fallon et al.
U.S. Appl. No. 13/737,225, filed Jan. 9, 2012, Fallon.
U.S. Appl. No. 13/757,412, filed Feb. 1, 2012, Fallon et al.
U.S. Appl. No. 13/836,135, filed Mar. 15, 2013, Fallon et al.

(56) References Cited

OTHER PUBLICATIONS

U.S. Appl. No. 13/926,822, filed Jun. 25, 2013, Fallon.
Borlongan. Recent preclinical evidence advancing cell therapy for Alzheimer's disease. Exp Neurol. Sep. 2012;237(1):142-6. doi: 10.1016/j.expneurol.2012.06.024. Epub Jun. 27, 2012.
Bray, et al. Effect of dietary protein content on weight gain, energy expenditure, and body composition during overeating. A randomized controlled trial. JAMA. Jan. 4, 2012; 307(1):47-55.
Chen, et al. Medicinal Functions of Bromelain and Its Application Prospect in Animal Husbandry, China Animal Husbandry & Veterinary Medicine, vol. 32, No. 1, p. 14-16. (in Chinese with English translation).
Ferrone, et al. Pancreatic enzyme pharmacotherapy. Pharmacotherapy. 2007; 27:910-920.
Information of Papain from Worthington Enzymes webpage http://www.worthington-biochem.com/pap/default.html Downloaded Jan. 17, 2013.
International search report and written opinion dated Feb. 21, 2013 for PCT/US2013/020183.
International search report and written opinion dated Nov. 12, 2012 for PCT/US2012/034489.
Millipore EMD catalog (online). Papain, unit definition, EMD Millipore Corp, 2013. Downloaded May 13, 2013.
Mitsui, et al. Role of aminopepridases in the blood pressure regulation. Biological and Pharmaceutical Bulletin of Japan, Pharmaceutical Sociey of Japan. 2004; 27(6):768-771.
Notice of Allowance dated May 29, 2013 for U.S. Appl. No. 13/481,087.
Office action dated Jan. 22, 2013 for U.S. Appl. No. 13/562,999.
Office action dated Jan. 25, 2013 for U.S. Appl. No. 13/208,963.
Office action dated Feb. 14, 2013 for U.S. Appl. No. 13/407,408.
Office action dated Feb. 21, 2013 for U.S. Appl. No. 12/047,818.
Office action dated Mar. 5, 2013 for U.S. Appl. No. 12/493,122.
Office action dated May 9, 2013 for U.S. Appl. No. 13/204,881.
Office action dated May 15, 2013 for U.S. Appl. No. 13/502,989.
Office action dated Jun. 25, 2013 for U.S. Appl. No. 13/144,286.
Office action dated Jun. 25, 2013 for U.S. Appl. No. 13/144,290.
Office action dated Jul. 15, 2013 for U.S. Appl. No. 13/002,136.
Office action dated Jul. 31, 2013 for U.S. Appl. No. 13/757,412.
Olivar-Parra, et al. Training referential communicative skills to individuals with autism spectrum disorder: a pilot study. Psychological Reports. 2011; 109:921-939.
Patel, et al. Formulation and evaluation of mucoadhesive glipizide microspheres. AAPS PharmSciTech. 2005; 6(1):E49-E55.
Petrolatum: Pharmaceutical Excipients. London: Pharmaceutical Press. 2006. 1-6.
Roxas, et al. Colds and influenza: a review of diagnosis and conventional, botanical, and nutritional considerations. Alternative Medicine Review. 2007; 12(1):25-48.
Serna, et al. Pathogenesis and treatment of Shiga toxin-producing *Escherichia coli* infections. Curr Opin Gastroenterol. Jan. 2008;24(1):38-47.
Sienaert, et al. Evidence-based treatment strategies for treatment-resistant bipolar depression: a systematic review. Bipolar Disord. Feb. 2013;15(1):61-9. doi: 10.1111/bdi.12026. Epub Nov. 27, 2012.
Sternby, et al. Carboxyl Ester Lipase (Bile Salt-Stimulated Lipase), Colipase, Lipase, and Phospholipase A2 Levels in Pancreatic Enzyme Supplements, 1997, Scandinavian Journal of Gastroenterology 32(3): 261-267.
Tamaro. Vitamin K deficiency as a cause of autistic symptoms. Http://web.archive.org/web/20090612022246/http://www.gutresearch.com/VitaminK.pdf. Published Jun. 12, 2009 as per Wayback Engine.
USDA. FDA Drug Safety Communication: *Clostridium difficile*-associated diarrhea can be associated with stomach acid drugs known as proton pump inhibitors (PPIs). Safety announcement. Feb. 8, 2012. Accessed Apr. 1, 2013. http://www.fda.gov/drugs/drugsafety/ucm290510.htm.
International preliminary report on patentability dated Jul. 17, 2014 for PCT/US2013/020183.
Office action dated Jul. 7, 2014 for U.S. Appl. No. 12/535,676.

Caldwell, et al. Crystalline Pancreatic Amylase. II. Improved Method for its Preparation from Hog Pancreas Glands and Additional Studies of its Properties. J. Am. Chem. Soc. 1952; 74(16):4033-4035.
Childhood Autism Rating Scale (CARS), Wikipedia, downloaded May 5, 2014.
Cichoke. Influenza. In: The Complete Book of Enzyme Therapy. D. Stewart, ed. Copyright 1999. Anthony J. Cichoke. Penguin Putnam, Inc., New York, New York. pp. "Contents", 50, 273-275 and 455.
Fido, et al. Olanzapine in the treatment of behavioral problems associated with autism: an open-label trial in Kuwait. Med Princ Pract. 2008;17(5):415-8. doi: 10.1159/000141508. Epub Aug. 6, 2008.
Krishnaswami, et al. A systematic review of secretin for children with autism spectrum disorders. Pediatrics. May 2011;127(5):e1322-5. doi: 10.1542/peds.2011-0428. Epub Apr. 4, 2011.
Notice of allowance dated Jun. 12, 2014 for U.S. Appl. No. 13/448,061.
Office action dated Apr. 10, 2014 for U.S. Appl. No. 13/502,989.
Office action dated Apr. 16, 2014 for U.S. Appl. No. 13/705,763.
Office action dated May 12, 2014 for U.S. Appl. No. 13/733,873.
Office action dated May 13, 2014 for U.S. Appl. No. 13/313,629.
Office action dated May 15, 2014 for U.S. Appl. No. 13/448,061.
Office action dated May 16, 2014 for U.S. Appl. No. 13/313,708.
Office action dated Jun. 17, 2014 for U.S. Appl. No. 12/386,051.
Office action dated Jun. 17, 2014 for U.S. Appl. No. 13/737,225.
Office action dated Jun. 19, 2014 for U.S. Appl. No. 12/386,051.
Office action dated Jun. 27, 2014 for U.S. Appl. No. 14/007,793.
Pancreatin 8X USP Powder. Product Specification. Jul. 2000. In: Product Manual. American Laboratories Incorporated. Omaha, NE. p. 1.
Williams, et al. Intravenous secretin for autism spectrum disorders (ASD). Cochrane Database Syst Rev. Apr. 18, 2012;4:CD003495. doi: 10.1002/14651858.CD003495.pub3.
U.S. Appl. No. 14/493,734, filed Sep. 23, 2014, Fallon.
U.S. Appl. No. 14/528,715, filed Oct. 30, 2014, Fallon.
eMedExpert, Antibiotics: Cephalosporins, Available online at: www.emedexpert.com/compare/ cephalosporins.shtml, available as early as Jun. 2, 2007 per Internet Archive Wayback Machine.
GM Chemie 2010 "Products: Hypromellose Phthalate" accessed from www.gmchemie.com on Sep. 22, 2014.
Merriam-Webster 2014 "Definition: Precipitate" accessed from www.mirriam-webster.com on Sep. 22, 2014.
Munasinghe et al. Digestive enzyme supplementation for autism spectrum disorders: a double-blind randomized controlled trial. J Autism Dev Disord. Sep. 2010; 40(9):1131-8.
Notice of allowance dated Dec. 23, 2014 for U.S. Appl. No. 14/007,793.
Office action dated Sep. 30, 2014 for U.S. Appl. No. 13/144,290.
Office action dated Sep. 30, 2014 for U.S. Appl. No. 13/660,642.
Office action dated Oct. 2, 2014 for U.S. Appl. No. 12/054,343.
Office action dated Oct. 6, 2014 for U.S. Appl. No. 12/493,122.
Office action dated Oct. 9, 2014 for U.S. Appl. No. 12/786,739.
Office action dated Nov. 7, 2014 for U.S. Appl. No. 12/786,739.
Office action dated Nov. 21, 2014 for U.S. Appl. No. 13/926,822.
Office action dated Dec. 18, 2014 for U.S. Appl. No. 14/037,696.
Office action dated Dec. 19, 2014 for U.S. Appl. No. 13/733,873.
U.S. Appl. No. 14/612,580, filed Feb. 3, 2015, Fallon et al.
U.S. Appl. No. 14/612,604, filed Feb. 3, 2015, Fallon et al.
Notice of allowance dated Feb. 2, 2015 for U.S. Appl. No. 13/926,822.
Office action dated Jan. 16, 2015 for U.S. Appl. No. 12/535,676.
Notice of allowance dated Feb. 20, 2015 for U.S. Appl. No. 12/386,051.
Notice of allowance dated Feb. 27, 2015 for U.S. Appl. No. 14/037,696.
Office action dated Mar. 6, 2015 for U.S. Appl. No. 13/757,412.
U.S. Appl. No. 14/693,711, filed Apr. 22, 2015, Fallon.
Fliri, et al. Drug effects viewed from a signal transduction network perspective. J Med Chem. Dec. 24, 2009; 52(24):8038-46. doi: 10.1021/jm901001p.
Nih, "Celiac Disease", National Digestive Diseases Information Clearinghouse: Bethesda, MD, 2008; 12 pages.
Notice of allowance dated Apr. 3, 2015 for U.S. Appl. No. 13/737,225.

(56) References Cited

OTHER PUBLICATIONS

Notice of allowance dated Apr. 10, 2015 for U.S. Appl. No. 13/144,290.
Notice of allowance dated Apr. 14, 2015 for U.S. Appl. No. 13/144,286.
Office action dated Apr. 6, 2015 for U.S. Appl. No. 14/493,734.
Office action dated Apr. 21, 2015 for U.S. Appl. No. 13/660,642.
Office action dated Apr. 21, 2015 for U.S. Appl. No. 14/087,930.
Office action dated Apr. 22, 2015 for U.S. Appl. No. 13/836,135.
Office action dated Apr. 24, 2015 for U.S. Appl. No. 12/786,739.
Office action dated Apr. 27, 2015 for U.S. Appl. No. 12/054,343.
Office action dated May 6, 2015 for U.S. Appl. No. 12/493,122.
Office action dated May 7, 2015 for U.S. Appl. No. 13/705,763.
U.S. Appl. No. 14/713,178, filed May 15, 2015, Fallon.
U.S. Appl. No. 14/713,221, filed May 15, 2015, Fallon et al.
U.S. Appl. No. 14/713,242, filed May 15, 2015, Fallon et al.
Office action dated May 27, 2015 for U.S. Appl. No. 13/502,989.
Office action dated Jun. 3, 2015 for U.S. Appl. No. 13/002,136.
Richards, et al. Diagnosis, management, and treatment of Alzheimer disease: a guide for the internist. Arch Intern Med. Apr. 26, 1999; 159(8):789-98.
Swayne, et al. Pathobiology of H5N2 Mexican avian influenza virus infections of chickens. Vet Pathol. Nov. 1997; 34(6):557-67.
U.S. Appl. No. 14/296,091, filed Jun. 4, 2014, Fallon.
Cichoke. Celiac disease. The complete book of enzyme therapy. Penguin. New York, NY. 1999; 174-177.
Curemark press release. Curemark Receives Investigational New Drug Clearance for CM-AT For Autism. Mar. 26, 2009. http://www.medicalnewstoday.com/releases/143723.php.
Digestive Enzyme Preparation: Pancreatin listed in Japanese Pharmacopoeia, Aug. 2008, <URL:http://database.japic.or.jp/pdf/newPINS/00009938.pdf> (in Japanese with English translation).
Lebenthal, et al. Enzyme therapy for pancreatic insufficiency: present status and future needs. Pancreas. Jan. 1994; 9(1):1-12.
MacDonald. Thyrotoxicosis treated with pancreatic extract and iodine. Lancet. 1943; 244(6251):788.
Notice of allowance dated Jan. 2, 2014 for U.S. Appl. No. 13/204,881.
Notice of allowance dated Sep. 15, 2014 for U.S. Appl. No. 14/037,652.
Office action dated Jan. 15, 2014 for U.S. Appl. No. 13/836,135.
Office action dated Jan. 16, 2014 for U.S. Appl. No. 12/046,252.
Office action dated Jan. 24, 2014 for U.S. Appl. No. 12/054,343.
Office action dated Jan. 24, 2014 for U.S. Appl. No. 12/786,739.
Office action dated Mar. 11, 2014 for U.S. Appl. No. 11/533,818.
Office action dated Aug. 7, 2014 for U.S. Appl. No. 13/836,135.
Office action dated Aug. 29, 2014 for U.S. Appl. No. 13/144,286.
Office action dated Sep. 18, 2014 for U.S. Appl. No. 13/502,989.
Office action dated Sep. 19, 2014 for U.S. Appl. No. 11/533,818.
Office action dated Sep. 19, 2014 for U.S. Appl. No. 13/737,225.
Office action dated Dec. 10, 2013 for U.S. Appl. No. 13/407,408.
Office action dated Dec. 12, 2013 for U.S. Appl. No. 13/144,286.
Office action dated Dec. 13, 2013 for U.S. Appl. No. 12/493,122.
Office action dated Dec. 13, 2013 for U.S. Appl. No. 13/144,290.
Office action dated Dec. 16, 2013 for U.S. Appl. No. 12/535,676.
Okahata, et al. Lipid-coated enzymes as efficient catalysts in organic media. Trends in Biotechnology. 1997; 15(2):50-54.
Sundstrom, et al. A deadly prion disease: fatal familial insomnia. J Neurosci Nurs. Dec. 2003; 35(6):300-5. Abstract only.
Borowitz et al., Study of a novel pancreatic enzyme replacement therapy in pancreatic insufficient subjects with cystic fibrosis J.Pediatr., 149:658-662 (2006).
Chazalette, A double-bind placebo-controlled trial of a pancreatic enzyme formulation (Panzytrat 25000) in the treatment of impaired lipid digestion in patients with cystic fibrosis RUG Invest., 5(5):274-280 (1993) Abstract Only.
U.S. Appl. No. 14/612,580 Office Action dated Dec. 24, 2015.
Notice of Allowance dated Mar. 1, 2016 for U.S. Appl. No. 14/087,930.
Notice of Allowance dated Dec. 23, 2015 for U.S. Appl. No. 12/493,122.
Office Action dated Jan. 15, 2016 for U.S. Appl. No. 13/502,989.
Office Action dated Jan. 26, 2016 for U.S. Appl. No. 12/054,343.
Office Action dated Jan. 29, 2016 for U.S. Appl. No. 12/786,739.
Office Action dated Feb. 1, 2016 for U.S. Appl. No. 13/503,844.
Office Action dated Feb. 17, 2016 for U.S. Appl. No. 14/713,178.
Office Action dated Feb. 26, 2016 for U.S. Appl. No. 12/535,676.
Office Action dated Mar. 2, 2016 for U.S. Appl. No. 14/693,711.
Office Action dated Dec. 15, 2015 for U.S. Appl. No. 14/087,930.
Office Action dated Dec. 18, 2015 for U.S. Appl. No. 14/640,385.
Office Action dated Dec. 24, 2015 for U.S. Appl. No. 13/757,412.

* cited by examiner

N = 26

CHYMOTRYPSIN LEVEL MEASUREMENTS IN FIVE
GROUPS OF CHILDREN AGED 6-18

N=320

Legend

PURPLE– NORMALS (CHILDREN WITHOUT ANY KNOWN CONDITION)

NAVY– CHILDREN WITH KNOWN CONDITIONS (GENETIC AND OTHERS)

AQUA - AUTISTIC CHILDREN

YELLOW - ADD CHILDREN

PINK - ADHD CHILDREN

ENZYME DELIVERY SYSTEMS AND METHODS OF PREPARATION AND USE

RELATED APPLICATIONS

This application is a divisional patent application of U.S. Utility application Ser. No. 12/386,051, filed Apr. 13, 2009, and is also related to international application no. PCT/US10/30895, filed Apr. 13, 2010, which claims the benefit of U.S. Utility application Ser. No. 12/386,051, each of which is herein incorporated by reference in its entirety.

FIELD OF THE INVENTION

The present invention relates generally to coated digestive/pancreatic enzyme preparations, and pharmaceutical compositions and enzyme delivery systems comprising the preparations, as well as methods for their preparation, use, and controlled delivery in treating individuals with neurological or behavioral diseases or conditions susceptible to treatment with enzymes.

BACKGROUND

Digestive enzymes are produced by the salivary glands, glands in the stomach, the pancreas, and glands in the small intestines. For example, digestive enzymes produced by the pancreas and secreted into the stomach and small intestine aid in digestion. Digestive enzymes produced by the pancreas are secreted into the duodenum, or upper segment of the small intestine, where the pH is around 5 to 6, and the enzymes assist in the digestion of food components, including carbohydrates, lipids, proteins and nucleic acids. However, when digestive enzymes are administered orally, the enzymes are exposed to highly acidic conditions in the stomach, with a pH of around pH 1-2, as well as gastric proteases which denature and degrade the enzymes.

Digestive enzymes have been administered to mammals to treat enzyme deficiencies caused by conditions affecting the pancreas, such as pancreatitis and pancreatic enzyme deficiency. Pancreatic enzymes administered to humans are commonly of porcine origin. Manufacturers of enzyme preparations have also used enteric coatings for lipase compositions in individuals with cystic fibrosis who require administration of lipases. The preparations for lipase delivery have used enteric coatings containing, for example, hypromellose phthalate, dimethicone 1000, and dibutyl phthalate.

Certain methods for coating sensitive bioactive substances have been described. U.S. Pat. No. 6,261,613 to Narayanaswamy et al. discloses particles that can contain yeast, coated in a shell of a fat in a beta prime form (i.e., triglyceride crystals having a blocky symmetry). The coating material can further contain emulsifiers such as those found in hydrogenated vegetable oil. However, the coating only allows release of the yeast in a limited temperature range of about 40° C. to about 55° C. U.S. Pat. No. 6,251,478 B1 to Pacifico et al. discloses certain sensitive substances including certain bioactive compounds encapsulated in a lipid material.

No description in the Background section should be taken as an admission that such disclosure constitutes prior art to the instant invention.

SUMMARY OF THE INVENTION

The present invention relates to coated digestive enzyme preparations, and pharmaceutical compositions and enzyme delivery systems comprising coated digestive enzyme preparations, which are useful in the treatment of individuals with autism, ADD, ADHD, Parkinson's disease, cystic fibrosis, other neurological and behavioral diseases or conditions. The coated and encapsulated digestive enzyme preparations of this invention permit controlled delivery of enzymes having increased stability and enhanced administration properties, to patients with neurological and behavioral diseases and conditions susceptible to treatment with digestive enzymes.

In some aspects, the present invention relates to a coated and/or encapsulated pancreatic/digestive enzyme preparation which comprises a core comprising digestive and/or 20 pancreatic enzymes and a coating which comprises an emulsifiable lipid. The core contains an amount of pancreatic/digestive enzyme effective for treatment of the patient's condition, which can be, for example, a neurological disorder such as autism, ADD, ADHD, CF and Parkinson's disease, or other diseases for which an effective amount of pancreatic/digestive enzymes can be administered. Among other properties, the coating protects the pancreatic/digestive enzyme from destabilizing factors such as solvents, heat, light, moisture and other environmental factors. The coating also provides controlled release of the pancreatic/digestive when the composite is exposed to a solvent. In addition, in one aspect of this invention, the coated digestive enzyme preparations of this invention have improved pour properties, and improved taste and smell of the digestive enzyme particles.

The invention also relates to a specific blend of enzymes and lipids for enzyme administration in individuals with Parkinson's disease, ADD, ADHD, autism and cystic fibrosis and other behavioral or neurological conditions and diseases. The coated digestive enzyme preparations can be used to obtain release at selected transit times or in selected locations of the gastrointestinal tract of humans. In one aspect, this invention relates to controlled release enzyme preparations.

In another aspect the invention relates to a coated digestive enzyme preparation comprising (a) a core containing a digestive enzyme particle, where the enzyme present in an amount of from about 5% to 90% by weight of the particles; and (b) a coating comprising an emulsifiable lipid, wherein the coating continuously coats the core and the emulsifiable lipid emulsifies upon exposure to a solvent.

In another aspect, this invention relates to a pharmaceutical composition comprising a therapeutically effective amount of an encapsulated enzyme preparation, which comprises (a) a core which comprises an amount of pancreatic or digestive enzymes effective for treating a subject suffering from autism, ADD, ADHD, Parkinson's' disease, cystic fibrosis, or other neurological condition or behavioral disorder susceptible to treatment by the enzymes; and (b) a coating comprising an emulsifiable lipid.

In yet another aspect, this invention relates to an enzyme delivery system comprising encapsulated enzyme preparation having particles which comprise: (a) a core 20 comprising pancreatic or digestive enzymes present in an amount of from about 5% to 95% by weight of the particles; and (b) a generally uniform coating to provide for controlled release of the enzymes, said coating comprising an emulsifiable lipid. In one aspect, the encapsulated enzyme preparation particles of the enzyme delivery system are non-aerosolizable.

In certain aspects, the methods of preparing enzymes according to this invention produce coated enzyme preparations characterized, for example, by controlled rates of release, reduction in aerosolization and safer administration, ability to be administered by a sprinkle/sachet delivery method, improved flow characteristics, enhanced shelf life and storage capacity, and other properties described herein. In other aspects, the coated enzyme preparation has improved pour properties which facilitate manufacturing and packaging processes, for example packaging in pouches and sachets.

In some aspects, the present invention is based on the surprising and unexpected discovery that certain coated digestive enzyme preparations which comprise a coating of emulsifiable lipid and a digestive enzyme core have favorable release and activity profiles and permit site time specific and/or location specific targeted release along the GI tract for the treatment of autism, ADD, ADHD, Parkinson's Disease and other neurological or behavioral conditions susceptible to treatment with digestive enzymes. In some aspects, the encapsulated pancreatic/digestive enzyme preparations are prepared to obtain specific delivery times or specific regions within the human gastrointestinal (GI) tract. In other aspects, the emulsifiable lipid composition is hydrogenated soy oil, but may be any suitable lipid or lipid blend.

The invention further relates in some aspects to more stable enzyme preparations protected against the environment to reduce, for example, degradation and/or denaturation of the enzymes. This permits delivery of more accurate doses of the enzyme preparation to treated individuals. The coating can also, in some aspects, provide emulsification when the enzyme preparations are contacted with appropriate solvents, while also surprisingly providing for controlled release of the enzyme in the gastrointestinal (GI) system. The emulsification properties of the coating in a solvent allows for controlled release of the enzyme, preferably at selected locations in the GI tract, where enzyme utilization provides the most effective treatment.

The present invention also relates to methods of making the enzyme preparations by lipid coating and/or encapsulation of digestive enzymes. The methods comprise providing an emulsifiable lipid, and coating screened pancreatic/digestive enzyme particles with the lipid. The digestive enzymes comprise 5-95% of the coated enzyme preparations by weight.

In another aspect, as described herein, the inventors have surprisingly discovery that the methods of this invention can be used to produce coated digestive enzyme preparations comprising digestive and/or pancreatic enzymes coated with an emulsifiable lipid alone, or with a lipid blend to achieve a controlled rate of enzyme release, with increased release of the pancreatic/digestive enzyme upon exposure of the encapsulated preparation to a suitable solvent. The inventors have discovered that encapsulated pancreatic/digestive enzyme preparations having a coating consisting essentially of one or more monoglycerides exhibit increased release of the pancreatic/digestive enzyme upon exposure of the encapsulated composite to a solvent, such as water, while protecting against release in 0.1 N HCl.

The invention further relates to methods for administering the enzyme preparations. In some aspects, the methods include administering the pancreatic/digestive enzymes as coated preparations. In some aspects, the invention relates to a method of treatment comprising administering to a subject with autism, ADD, ADHD, Parkinson's disease, cystic fibrosis, or other behavioral or neurological condition in need of treatment with digestive enzymes, at least two doses of a composition comprising a therapeutically effective amount of an encapsulated digestive enzyme preparation comprising a core comprising a digestive enzyme; and a coating comprising an emulsifiable lipid. Determination of whether a subject is in need of treatment with an effective amount of digestive enzymes may be based on a determination that the subject has an enzyme deficiency.

In addition, the invention relates to the delivery to humans of pancreatic/digestive enzyme composites, preparations, enzyme delivery compositions or systems comprising no or fewer excipients, carriers, additives and/or extenders, and/or requiring the use of no or fewer solvents' in the enzyme preparations. In some embodiments, the coating consists essentially of hydrogenated soy oil. This can reduce exposure to potentially toxic substances and will also reduce the possibility of allergy formation. The invention further relates to the delivery of pancreative and/or digestive enzymes with improved safety of administration.

In addition, the invention relates to methods of improved manufacturing resulting from the enhanced flow properties imparted to enzyme preparations by the lipid encapsulation. The lipid encapsulation of pancreatic/digestive enzymes forms a lipid barrier to moisture which permits improved flow of the encapsulated enzyme preparations in the packaging machinery.

The summary of the invention is not intended to be a complete or exhaustive recounting of every aspect of the invention described herein. Other aspects of the invention will be apparent from further description set forth herein.

DETAILED DESCRIPTION OF PREFERRED EMBODIMENTS

Figure 1:
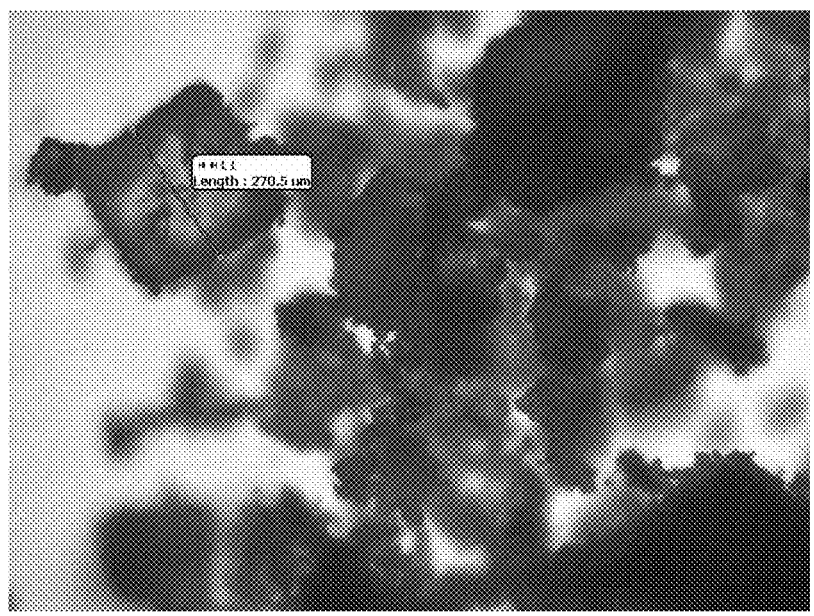
FIG. 1 shows an electron micrograph of an unprocessed, raw digestive enzyme particles.

As described throughout, this invention relates in some embodiments to coated digestive enzyme preparations, and pharmaceutical compositions and enzyme delivery systems comprising coated digestive enzyme preparations, which are useful in the treatment of individuals with autism, ADD, ADHD, Parkinson's disease, cystic fibrosis, other neurological and behavioral diseases or conditions.

Autism (sometimes called "classical autism") is the most common condition in a group of developmental disorders known as the autism spectrum disorders (ASDs). Autism is characterized by impaired social interaction, problems with verbal and nonverbal communication, and unusual, repetitive, or severely limited activities and interests. Other ASDs include Asperger syndrome, Rett syndrome, childhood disintegrative disorder, and pervasive developmental disorder not otherwise specified (usually referred to as PDD-NOS). It has been estimated that three to six children out of every 1,000 will have autism.

Attention deficit-hyperactivity disorder (ADHD) is a neurobehavioral disorder that affects 3-5 percent of all children in the US. It interferes with a person's ability to stay on a task and to exercise age-appropriate inhibition (cognitive alone or both cognitive and behavioral). Some of the warning signs of ADHD include failure to listen to instructions, inability to organize oneself and school work, fidgeting with hands and feet, talking too much, leaving projects, chores and homework unfinished, and having trouble paying attention to and responding to details. There are several types of ADHD: a predominantly inattentive subtype, a predominantly hyperactive-impulsive subtype, and a combined subtype. ADHD is usually diagnosed in childhood, although the condition can continue into the adult years.

Parkinson's disease (PD) belongs to a group of conditions called motor system disorders, which are associated with the loss of dopamine-producing brain cells. The four primary symptoms of PD are tremor, or trembling in hands, arms, legs, jaw, and face; rigidity, or stiffness of the limbs and trunk; bradykinesia, or slowness of movement; and postural instability, or impaired balance and coordination. As these symptoms become more pronounced, patients may have difficulty walking, talking, or completing other simple tasks. PD usually affects people over the age of 50. Early symptoms of PD are subtle and occur gradually. In some people the disease progresses more quickly than in others. As the disease progresses, the shaking, or tremor, which affects the majority of PD patients may begin to interfere with daily activities. Other symptoms may include depression and other emotional changes; difficulty in swallowing, chewing, and speaking; urinary problems or constipation; skin problems; and sleep disruptions.

Cystic fibrosis (CF) is one of the most common life-shortening, genetic diseases. In the United States, 1 in 4,000 children are born with CF. It is most common among western European populations; one in twenty-two people of Mediterranean descent are carriers of one gene for CF, making it the most common genetic disease in these populations. CF is caused by a mutation in the gene, cystic fibrosis transmembrane conductance regulator (CFTR). The product of this gene is a chloride ion channel important in creating sweat, digestive juices, and mucus. Although most people without CF have two working copies (alleles) of the CFTR gene, only one is needed to prevent cystic fibrosis. Cystic fibrosis affects the exocrine (mucus) glands of the lungs, liver, pancreas, and intestines, causing progressive disability due to multisystem failure. CF can be characterized by, for example, 1) thick mucus production which results in frequent lung infections; 2) diminished secretion of pancreatic enzymes causing poor growth, greasy stools, and deficiency in fat-soluble vitamins; and 3) infertility in the males due to the condition congenital bilateral absence of the vas deferens. Often, symptoms of CF appear in infancy and childhood. Meconium ileus is a typical finding in newborn babies with CF.

Enzyme preparations with non-lipid enteric coatings have been used to deliver lipases in individuals requiring administration of lipases to individuals with cystic fibrosis in need of enzyme treatment. In addition, Fallon has described certain methods and enzyme compositions for use in treating children and other individuals, with autism, ADD, ADHD, Parkinson's disease and other neurological diseases or conditions, for example, U.S. Pat. Nos. 7,138,123, 6,660,831, 6,632,429; 6,534,063, hereby incorporated by reference as if set forth in full herein.

The nature of the human digestive tract creates challenges for the delivery of digestive enzymes to patients with neurological and behavioral conditions susceptible to treatment with digestive enzymes. Multiple temperature and pH changes over the course of the digestive tract make specific delivery a necessity and a challenge. For instance, pH as low as 1 is encountered in the stomach, but rapidly increases to a more basic pH of 5-6 in the proximal small intestine. For example, generally the pH in the stomach is approximately 1.2, the pH in the duodenum is about 5.0 to 6.0; the pH in the jejunum is about 6.8, and the pH is about 7.2 in the proximal ileum and about 7.5 in the distal ileum. The low pH in the stomach which changes rapidly to a more basic pH of 5-6 in the proximal small intestines, call for a specific delivery 25 method depending upon where the enzyme is to be delivered.

For example, children with cystic fibrosis whose condition requires administration of lipases, require delivery of the lipases to the latter portion of the small intestine. In contrast, the inventors have determined that children with autism who need treatment with proteases require delivery of those enzymes to the proximal small intestine.

Delivery of digestive enzymes can also be challenging due to the rapid degradation and denaturing of enzymes at ambient room temperature, as well as the enhanced degradation and denaturing that can occur with high temperature, pressure, humidity and/or exposure to light. Moisture and heat together can quickly destabilize enzymes, reducing their effectiveness, and shortening shelf life, leading to inaccurate dosing. Denaturization or destabilization of the enzymes can reduce their effectiveness by reducing the dose of active enzymes to less than the amount needed for effective treatment. Alternatively, attempting to compensate for the denaturization or destablization by increasing the dose to ensure an effective level of active enzyme, could risk an overdose or overfilling a capsule or other dosage form. To protect and stabilize the pancreatic/digestive enzyme from unfavorable conditions, such a penetration, decomposition, the pancreatic/digestive enzyme (core) may be coated or encapsulated in a continuous coating containing an emulsifiable lipid. In another aspect, this invention provides new coated enzyme preparations with improved shelf life.

Manufacturers of enzyme preparations have used enteric coatings to deliver lipases in individuals requiring administration of lipases, such as individuals with cystic fibrosis. Because the porcine enzymes are delivered in a mixture of proteases, lipases and amylases, and because these compositions for human consumption were prepared for lipase delivery, the use of these enteric coatings, which include such substances as hypromellose phthalate, dimethicone 1000, and dibutyl phthalate, preclude delivery of proteases at the proper location in the digestive tract. All other enzyme preparations presently on the market contain at least one of these enteric coating substances and/or other additives in the preparation. Some additives that enable manufacturing, such as additives to improve flow properties, may further risk patient reactivity or sensitivity to the enzyme preparation.

In one embodiment the present invention includes a coated digestive enzyme preparation and/or composite, which, in some embodiments is an encapsulated pancreatic/digestive enzyme preparation. In other aspects, the invention includes enzyme delivery systems and pharmaceutical compositions comprising coated pancreatic/digestive enzyme preparations. These coated or encapsulated enzyme preparations contain cores comprising pancreatic or digestive enzyme particles, and a coating comprising an emulsifiable lipid.

The coatings in the digestive/pancreatic enzyme preparations create a barrier to degradation and denaturation, and allow more accurate levels of active enzymes to reach the treated individuals. The lipid coating of this invention provides a significant barrier to moisture, heat, humidity and exposure to light by allowing for a physical barrier as well as one that prevents and or reduces hydrolysis. The coated enzyme preparations undergo less hydrolysis as a result of protection from moisture in the environment by the lipid coating. As a result of the present invention, pancreatic/digestive enzymes are provided which can tolerate storage conditions (e.g., moisture, heat, oxygen, etc.) for long periods of time thus enabling extended shelf life. The coating of the encapsulated enzyme preparation protects the enzyme from the environment and provides emulsification in a solvent without detracting from the abrasion resistance of the coating. The invention thus further relates to more stable enzyme preparations.

The coated enzyme preparations therefore reduce overfilling of the enzyme dosage, and enhance delivery of more accurate doses of the enzyme to individuals with autism, ADD, ADHD Parkinsons's disease, cystic fibrosis and other neurological or behavioral conditions or diseases susceptible to treatment with pancreatic or digestive enzymes.

In addition, because children and other individuals with autism and other conditions often have multiple sensitivities to foods, additives, colorants and other carriers, excipients or substances used in drug formulations, it is a challenge to make an enzyme delivery system that avoids the use of allergens, and other carriers, excipients, extenders, colorants, etc. that could potentially add to adverse symptoms or the morbidity of patients. Furthermore, in very young children an enzyme delivery system which allows ease and tolerability, is paramount. A sachet delivery system for these enzyme preparations has also heretofore not been achieved.

It is another aspect of the present invention to make an enzyme preparation without the use of extenders colorants, dyes, flow enhancers and other additives to reduce the potential for allergens and other sensitivity reactions in children and other treated individuals. It has been discovered that in some embodiments, the digestive enzymes can surprisingly be encapsulated with a single lipid excipient to improve retention of enzyme activity, ease of administration, tolerability, and safety of administration, among other properties. Surprisingly digestive enzyme particles containing lipases can be successfully encapsulated with coating consisting essentially of only hydrogenated soy oil.

In addition, porcine pancreatic/digestive enzymes posses a significant odor and taste, similar to cured/smoked pork. This taste can be strong and offensive to some individuals taking enzyme replacement, and especially to children. The addition of a lipid coating provides significant taste masking to the enzyme preparation, which allows for the tolerance of taste, as the lipid coating is odorless and tasteless. The use of this method of taste masking which does not involve the use of color, dyes, perfumes, recipients, or other substances is preferable for the administration of medications, which have an unpleasant or undesirable taste and odor. In other embodiments, this invention relates to coated digestive enzyme preparations with improved taste and smell.

In some embodiments, the coatings on the digestive enzyme particle cores are preferably continuous coatings. By "continuous," it is meant that the pancreatic/digestive enzyme is uniformity protected. The continuous coating of the fully surrounds or encapsulates the pancreatic/digestive enzymes. The encapsulation provides protection of the pancreatic/digestive enzyme from conditions such as moisture, temperature, and conditions encountered during storage.

In addition, the encapsulation also provides controlled release of the pancreatic/digestive enzyme. The emulsification properties of the coating in a solvent allows for controlled release of the enzyme in the gastrointestinal system, preferably the region of the GI tract where the enzymes are to be utilized. The coating of the encapsulated composite protects the enzyme from the environment and provides emulsification in a solvent without detracting from the abrasion resistance of the coating. For example, for conditions requiring treatment with proteases, the release of the protease portion of the enzymes is necessary in the proximal small intestine, thereby necessitating a lipid encapsulation which has a dissolution profile between 30-90 minutes. The dissolution profile may also be about 30, 35, 40, 45, 50, 55, 60, 65, 70, 75, 80, 85 or 90 minutes. Dissolution profiles may be obtained using methods and conditions known to those of skill in the art. For example, dissolution profiles can be determined at various pH's, including pH. 1, 2, 3, 4, 5, 6, 7, 8, 9, 10.

The rate of release of the bioactive substance can also be controlled by the addition of additives as described below. When the preparations are exposed to a solvent, the solvent interacts with the mollifiable lipid in the coating and results in emulsification of the coating and release of the bioactive substance.

"Encapsulate" as used herein means that the coating completely surrounds the pancreatic/digestive enzyme. In a population of encapsulated particles, encapsulated enzyme preparations may include contaminating or small portion of particles with a substantially continuous coating as long as the release profiles of the encapsulated particles are not significantly altered. A coated or encapsulated particle may contain one or more digestive enzyme particles enveloped in one coating to form one coated or encapsulated digestive enzyme particle in the coated or encapsulated digestive enzyme preparation.

The present invention also includes a method for preparing the enzyme preparations, pharmaceutical compositions, and delivery systems for the treatment of neurological or behavioral disorders such as autism, ADD, ADHD Parkinsons's disease, cystic fibrosis and other behavioral or neurological conditions or diseases susceptible to treatment with pancreatic or digestive enzymes. By "susceptible to treatment with pancreatic or digestive enzymes" is meant that one or more symptoms of the disease or condition can be alleviated, treated, or reduced by administration of an effective amount of pancreatic or digestive enzymes.

In some aspects, the invention relates to the production of selected coated enzyme preparations made by coating digestive enzyme particles with lipids not previously used in coated digestive enzyme preparations. The unique mixtures of emulsifiable lipids and enyzmes can deliver certain components of the pancreatic/digestive enzymes to selected locations and/or at selected times during transit of the GI tract. In some aspects, the invention relates to methods of delivering digestive enzymes to humans based upon dissolution profiles.

The emulsifiable lipid is any lipid, lipid mixture, or blend of lipid and emulsifiers which emulsifies when exposed to a solvent, and has a melting point which allows the lipid to be a solid at typical storage temperatures. The emulsifiable lipid can be a vegetable or animal derived-lipid. In some embodiments, the emulsifiable lipid consists essentially of, or comprises one or more monoglycerides, diglycerides or triglycerides, or other components including, for example, emulsifiers found in hydrogenated vegetable oils. In another embodiment the lipid is a non-polar lipid.

As used herein, animal and/or vegetable "derived" lipids can include fats and oils originating from plant or animal sources and/or tissues, and/or synthetically produced based on the structures of fats and oils originating from plant or animal sources. Lipid material may be refined, extracted or purified by known chemical or mechanical processes. Certain fatty acids present in lipids, termed essential fatty acids, must be present in the mammalian diet. The lipid may, in some embodiments, comprise a Type I USP-National Formulary vegetable oil.

The digestive enzyme used in the present invention can be any combination of digestive enzymes of a type produced by the pancreas, including, but not limited to digestive enzymes from a pancreatic source or other sources. The scope of the invention is not limited to pancreatic enzymes of porcine origin, but can be of other animal or plant origin as well as those which are synthetically derived. The digestive enzyme may be derived from mammalian sources such as porcine-derived digestive enzymes. The enzyme may include one or more enzymes, and can also be plant derived, synthetically derived, recombinantly produced in microbial, yeast, or mammalian cells, and can include a mixture of enzymes from one or more sources. Digestive enzyme, can include, for example, one or more enzymes from more or more sources mixed together. This includes, for example, the addition of single digestive enzymes to digestive enzymes derived from pancreatic sources in order to provide appropriate levels of specific enzymes that provide more effective treatment for a selected disease or condition. One source of digestive enzymes can be obtained, for example, from Scientific Protein Laboratories (see Table 6). The digestive enzyme may be, for example a pancreatin/pancrelipase composition. In one embodiment, the digestive enzymes will comprise or consist essentially of 25 USP units/mg protease, 2 USP Unit/mg, and 25 USP Units/mg amylase. The term digestive enzyme may refer to one or more enzymes of a type produced by the pancreas.

The digestive enzyme particles used as cores in the present invention include digestive enzyme particles where about 90% of the particles are between about #40 and #140 USSS mesh in size, or between about 105 to 425 µm, or where at least about 75% of the particles are between about #40 and #80 mesh, or about 180 to 425 µm in size. Particles between #40 and #140 mesh in size pass through #40 mesh but do not pass through #140 mesh. The coated or encapsulated digestive enzyme particles in one embodiment of this invention may comprise less than about 35, 30, 25, 20, 15 or 10% of the particles which can be sieved through #100 mesh (150 µm). In some embodiments, the term "non-aerosolizable" refers to a coated or encapsulated enzyme preparation where less than about 20% or less than about 15% of the particles can be sieved through #100 mesh (150 µm). The encapsulated digestive enzyme preparation can be an encapsulated digestive enzyme composite where the digestive enzyme particles contain two or more enzymes.

The minimum amount of pancreatic enzyme present in the core is at least about 5% active enzymes by weight of the coated enzyme preparation, but in other embodiments may be at least about 30%, or at least about 50% by weight. The maximum amount of pancreatic/digestive enzyme present in the composite is at most about 95% by weight, and in other embodiments at most about 90%, 85%, 80%, 75% or 70% of the coated enzyme preparation. In other embodiments, the amount of pancreatic enzyme present in the composite is about 10%, 15%, 20%, 25%, 35%, 40%, 45%, 55%, 60%, 65%, 70%, 72.5%, 75%, 77.5%, 80%, 82.5%, 87.5%, or 92.5% by weight or anywhere in between. At least about or at most about a of enzyme may include equal to or about that % of enzyme. The term "about" includes equal to, and a range that takes into account experimental error in a given measurement. As used in connection with particle sizes, the term "about" can refer to plus or minus 10, 9, 8, 7, 6, 5, 4, 3, 2 or 1% or anywhere inbetween. As used in connection with % particles that can be sieved, the term "about" can refer to plus or minus 10, 9, 8, 7, 6, 5, 4, 3, 2 or 1% or anywhere inbetween.

The composition which contains the encapsulated digestive enzyme preparation or composite can be delivered as a sprinkle, powder, capsule, tablet, pellet, caplet or other form. Packaging the encapsulated enzyme preparations in an enzyme delivery system that further comprises single dose sachet-housed sprinkle preparations allows for ease of delivery, and accurate dosing of the enzyme, by allowing a specific amount of enzyme to be delivered in each dosing. Allowing for specific unit dosing of an enzyme preparation which maintains the enzyme activity within specific stability parameters in an enhancement over other sprinkle formulations, which are housed, in a multi-unit dosing form that allows for air, moisture and heat to depredate and denature the enzyme preparation. In a preferred embodiment the powder or sachet is housed in a trilaminar foil pouch, or similar barrier to keep out moisture and to protect the enzyme preparation from adverse environmental factors. The invention further relates to an improvement in stability due to a reduction in hydrolysis due to the lipid encapsulation.

Further the lipid encapsulation methodology reduces the aerosolization of the enzyme preparation that may be caustic to the child if inhaled through the lungs or the nose. In another embodiment, the invention includes delivery of digestive enzymes with improved safety of administration, by reducing the amount of aerosolization of the enzyme. The lipid encapsulation reduces aerolization and the potential for caustic burn, aspiration, and/or aspiration pneumonias in children and administrators of the enzyme preparation, thereby reducing the potential for illness in already compromised children such as those with cystic fibrosis, and leading to safer administration.

As used herein, the term "non-aerosolizable" will be used to refer to a coated or encapsulated enzyme preparation where substantially all of the particles are large enough to eliminate or reduce aerosolization upon pouring of the coated enzyme preparation compared to uncoated enzyme particles. For example, the term "non-aerosolizable" may refer to a coated or encapsulated enzyme preparation where at least about 90% of the particles are between about #40 and #140 mesh in size, or between about 106 to 425 μm, or where at least about 75% of the particles are between about #40 and #80 mesh, or about 180 to 425 μm. The term "non aerosolizable" may also refer to a coated or encapsulated enzyme preparation where less than about 35, 30, 25, 20, 15 or 10% of the particles can be sieved through #100 mesh (150 μm). In some embodiments, the term "non-aerosolizable" refers to a coated or encapsulated enzyme preparation where less than about 20% or less than about 15% of the particles can be sieved through #100 mesh (150 μm).

As described and referred to herein, suitable pancreatic/digestive enzymes and suitable coatings may be used in the compositions and methods of this invention. The choice of suitable enzymes and of suitable lipid coatings, including choice of the type or amount of enzymes or coating, are guided by the specific enzyme needs of the individuals, and the selected diseases to be treated. The encapsulated enzyme preparations that are one aspect of this invention have not been previously described.

In some embodiments, the invention relates to specific blends of enzymes and lipids selected for delivery in individuals with Parkinson's disease, ADD, ADHD, autism, cystic fibrosis and other neurological and behavioral disorders susceptible to treatment with digestive/pancreatic enzymes based on the transit times in the human gastrointestinal tract. It can further be based upon the need of the patient to be treated for various components of the digestive enzymes. Further, the invention relates to improvement of the delivery of digestive enzymes to humans based specifically upon required delivery times, and dissolution profiles.

While general methods for coating certain sensitive biologic substances have been described, see, e.g., U.S. Pat. No. 6,251,478, hereby incorporated by reference, the encapsulated bioactive substance of this invention is an enzyme preparation comprising a core containing digestive enzymes comprising or consisting of multiple proteases, lipases and amylases, and a coating which comprises or consists essentially of an emulsifiable lipid.

Additives can be blended with the emulsifiable lipid. Selection of the lipid(s) and additives will control the rate of release of the bioactive substance. In the case of the digestive and or pancreatic enzymes, the lipid coat must be uniquely chosen to release the bioactive substance in the area of the digestive tract selected for release to optimize treatment.

The invention further relates to the administering of the coated and/or encapsulated enzyme preparation in a sachet or pouch preparation for ease of delivery to children and adults. In some embodiments, the invention specifically relates to the administration of a coated enzyme particle preparation, housed in a sachet or pouch. This facilitates administration, including but not limited to, administration in food or drink, direct administration into the oral cavity, or administration directly into the GI system through an NG-tube, G-tube or other GI entrances or deliveries.

In some embodiments, each dose contains about 100 to 1500 mg of coated or encapsulated enzyme preparation, and each dose may contain about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500 mg of coated or encapsulated enzyme preparation. "About" can include 80 to 125% of the recited preparation. Each dose may also be plus or minus 10% of the recited weight. In one embodiment each does will have a protease activity of not less than about 156 USP units/mg plus or minus 10%. The protease activity may also be not less than about 100, 105, 110, 115, 120, 125, 130, 135, 140, 145, 150, 155, 160, 165, 170, 175, 180, 185, 190, 195, or 200 USP units/mg.

In other embodiments, the invention relates to methods of treatment comprising administering to a subject with autism, ADD, ADHD, Parkinson's' disease, cystic fibrosis, or other behavioral or neurological condition susceptible to treatment with digestive enzymes, at least two doses of a composition comprising a therapeutically effective amount of the coated digestive enzyme preparations. In certain embodiments, about 80% of the enzyme is released by about 30 minutes in a dissolution test performed at pH 6.0. In other embodiments, about 80% of the enzyme is released by about 30 minutes after the coated digestive enzyme preparations reach the small intestine.

Another embodiment of the invention relates to the improvement of delivery of enzymes to humans by reducing the use of excipients, extenders and solvents currently used in the preparations for delivery of digestive enzymes to humans. For example, the encapsulated digestive enzyme preparation may contain only one excipient, which increases the safety of administration by decreasing the chance of an allergic response. In one embodiment, the excipient is hydrogenated soy oil.

Because, in some embodiments, the lipid encapsulation method does not require the enzyme preparation to be treated with solvents, extenders and excipients to facilitate flow or improve stability, one aspect of the invention includes a "clean" preparation of GRAS substances (generally regarded as safe) to be administered. The reduction in the use of solvents, extenders excipients and other additives permitted by the methods of this invention reduces the exposure of the individuals taking the enzyme replacement to potential allergens, thereby producing a hypoallergenic enzyme preparation that further enhances its potential uses in the treatment of individuals who might otherwise develop an allergic response to treatment. Administration of the coated enzyme preparations of this invention can thus reduce exposure to potentially toxic substances and will also reduce the possibility of allergy formation. Accordingly, in some embodiments, the encapsulated digestive enzyme preparation is hypoallergenic.

The invention further relates in another aspect to the delivery of digestive enzymes with improved safety of administration. The lipid coat adds weight to the enzyme preparation, which reduces the potential for aerosolization. Previous uncoated enzymes have been shown to become aerosolized, and can therefore be inhaled and contact the nasal cavity or the lungs, causing injury to the mucosa of those taking and those administering the enzyme preparation.

The invention further relates to the improvement of administering a sachet preparation for delivery to children. The invention specifically relates to the administration of a coated digestive enzyme preparation, housed in a sachet which allows for particular types of administration including but not limited to administration in food, drink, or direct administration into the oral cavity or directly into the GI system through a NG-tube, G-tube or other GI entrances. The use of a sachet delivery of enzymes has heretofore been not utilized in the enzyme preparations presently marketed. The sachet, which represents a unit dosage or multiple doses for a day, and represents a single unit dose. The sachet of a trilaminar foil allows the enzyme/lipid powder to remain stable, and allows for ease of administration.

In another embodiment, the invention relates to a method of controlling the rate of release of the pancreatic/digestive enzyme from an encapsulated enzyme preparation upon exposure to a solvent. In some aspects, the method comprises blending an emulsifiable lipid with an amount of one or more additives to obtain a lipid blend; and coating the digestive enzyme particle with the blend to form an encapsulated digestive enzyme preparation containing particles comprising a core which contains the enzyme, and a coating which contains the lipid. In some embodiments, the emulsifiable lipid is a blend where the emulsifiable lipid and additive are not the same, and where the rate of release of the enzyme from the encapsulated composite upon exposure to a solvent is decreased as the amount of additive is increased. In the alternative, the rate of release of the enzyme from the encapsulated composite upon exposure to a solvent is increased as the amount of additive is decreased.

The lipid coating surprisingly does not appear to be reduced or destroyed by HCl (hydrochloric acid) present in the stomach, thereby protecting the enzyme from degradation following administration until the enzyme preparation reaches its target region in the GI tract. Further the lipid coat reduces the exposure of the enzyme to attack by water, thereby reducing hydrolysis, and further protecting the digestive enzymes from degradation. In addition, the inventors have found that an excipient containing only lipid can be used to coat or encapsulate digestive enzyme particles containing lipase.

The use of digestive enzymes for the treatment of specific disease targets is made possible, in one aspect of the invention, by preparing encapsulated digestive enzyme composite having differing release characteristics. Since various neurological and behavioral diseases can impact the gastrointestinal systems in humans in various ways, the use of specific enzyme preparations and the ensuing encapsulation can make the difference as to where and for what duration of time the enzyme preparation is delivered.

The invention therefore relates to improvement of the delivery of digestive enzymes to humans based specifically upon needed delivery times, and dissolution profiles. For example, in certain aspects of the invention, the rate of release and dissolution characteristics are unique to the lipid encapsulations of this invention. The preparation of coated digestive enzymes using enzymes and lipids selected to optimize treatment of behavioral and neurological conditions and diseases susceptible to treatment with digestive enzymes has not been previously described.

As an example, previous enteric coatings for digestive and or pancreatic enzymes have delayed release of enzyme mixture for a period of time too long for delivery of the protease portion to the proximal small intestine. For instance, in administration to patients with cystic fibrosis where delivery of lipases is required for effective treatment, the dissolution profile of the enterically coated digestive enzymes needs to favor a longer delay in the release of the enzymes, as well as the delivery of a high lipase formulation.

Prior to the instant invention, lipid encapsulation had not been used as a delayed and/or protective mechanism for lipase delivery to treat individuals with cystic fibrosis.

The inventors have further recognized that for treatment of patients with autism who require delivery of protease enzymes for effective treatment, the lipid encapsulate can be modified to deliver the protease during an earlier transit time window, in the proximal small intestine, to optimize protein digestion. In another example, the inventors have recognized that for patients with Parkinson's disease who have slow GI transit times due to the dysautonomic nature of their neurological condition, still another release profile is required to deliver enzymes for effective treatment. The lipid and/or additive selection will be made to obtain enzyme release at later times after administration.

It has not been previously appreciated that transit times for digestive enzymes through the digestive system could be controlled by layering lipids, or through encapsulation with specific lipid types. In still another aspect, this invention relates to a selected blend of enzymes and lipids for delivery in individuals with Parkinson's disease, ADD, ADHD autism and cystic fibrosis and other behavioral or neurological diseases or conditions susceptible to treatment with pancreatic/digestive enzymes, based upon the transit times in the gastrointestinal systems of humans.

The invention further relates to an improvement in manufacturing due to the enhanced flow properties imparted by the lipid encapsulation. The improvement in manufacturing can also accomplished through the lipid encapsulation of a pancreatic/digestive enzyme due to the lipid barrier to moisture thus allowing for improved flow in the packaging machinery. The improved flow qualities may facilitate packaging of the coated digestive enzyme preparations into, for example, pouches or sachets.

In one aspect, this invention relates to the use of a lipid encapsulation method to make a coated digestive enzyme preparation for specific delivery times within the human gastrointestinal (GI) tract targeted for use in the treatment of a specific disease or condition. This disease or condition may be caused by or characterized by a digestive deficit that can be treated by the administration of digestive enzymes to the appropriate region of the GI tract. The neurological or behavioral disease or condition is one not traditionally associated with the digestive system, where one or more symptoms can be treated by administering an effective amount of a pancreatic and/or digestive enzyme preparation.

Thus, the present specification is directed at lipid encapsulation of specific enzymes targeted for use in the treatment of specific diseases, and the encapsulation method includes the amount and type of lipids used in the methods of this invention for the preparation of the encapsulated digestive enzyme composite. The present invention also relates to methods of making the enzyme preparations by lipid coating and/or encapsulation of pancreatic and/or digestive enzymes. The methods comprise providing an emulsifiable lipid, and coating pancreatic/digestive enzyme particles with the lipid, where the pancreatic/digestive enzymes comprise 5-90% of the coated enzyme preparations by weight. In some aspects the uncoated pancreatic/digestive enzyme particles have a size range of about 105-425 µm.

In one embodiment, the invention relates to a method of preparing an encapsulated digestive enzyme preparation, the method comprising a) screening uncoated digestive enzyme particles to obtain particles of a suitable size for encapsulation; and b) coating the screened digestive enzyme particles with an emulsifiable lipid to form coated or encapsulated digestive enzymes containing a core which contains the pancreatic/digestive enzyme and a coating which contains the emulsifiable lipid. In some embodiments, the encapsulated digestive enzyme preparation is a controlled release digestive enzyme preparation, which may have enhanced flow properties. The preparations may be useful in the treatment of individuals with autism, ADD, ADHD, Parkinson's' Disease, Cystic fibrosis and other neurological conditions.

Screening of the particles may include quality control steps to improve the activity, appearance or particle size of the digestive enzyme. For example, the particles may be analyzed to determine enzyme activity content, and/or visualized using chromatographic, microscopic or other analytical methods. The particles may also be screened to obtain particles of a suitable size for encapsulation by removing particles that are too fine or too large. For example, the particles may be sieved to obtain particles of a suitable size or more uniform size range for encapsulation. As a further example, the particles may be sieved through USSS #40 mesh and through USSS #140 mesh. Particles that pass through the #40 mesh but are retained by the #140 mesh are of an appropriate size range for coating or encapsulation Particles may also be screened by sieving through USSS #140, #120, #100, #80, #70, #60, #50, #45, or #40 mesh, or any combination thereof.

Enzyme preparations supplied by the API supplier may be provided as irregular shaped, and multi-sized particles, with uneven edges, and much clumping, and containing some crystalline salt particles. (See, for example, FIG. 1). Uneven particle size and shape reduces flow properties, and interferes with packaging. In addition, pouring uncoated enzyme into the mouth of an individual would be difficult, and potentially may cause too much or too little of the enzyme to be delivered. Processing the digestive enzyme particles according to methods in accordance with one aspect of this invention yields a non-dusty, free-flowing particulate preparation suitable for sachet packaging and for pouring onto food or drink. In addition, as discussed throughout, the use of lipid encapsulation to prevent aerosolization, and therefore increase safety, to increase flow properties which enhance manufacturing of a pharmaceutical is an embodiment of the instant invention.

Figure 3:
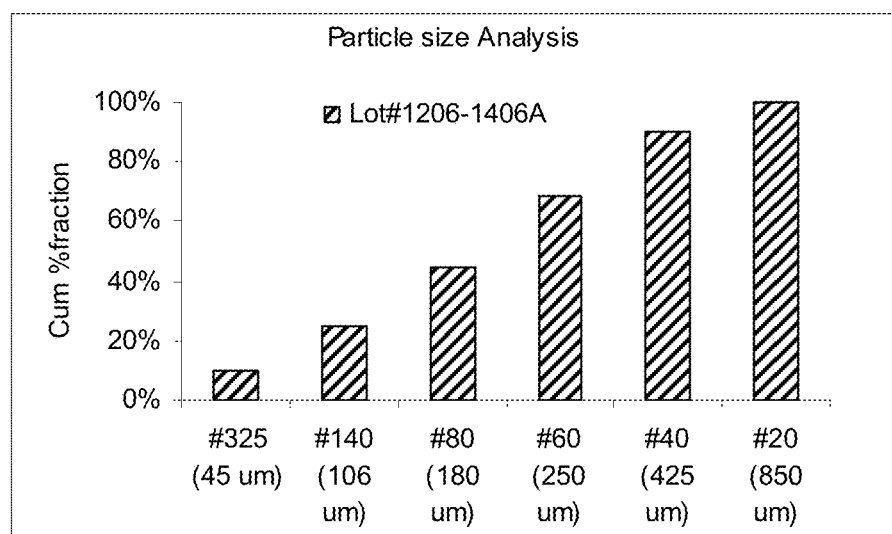
FIG. 3 shows a bar graph particle size analysis for a raw digestive enzyme particles with the % of particles that can pass through a USSS seive, as indicated on the y-axis.

The size distribution of particles in an exemplary raw enzyme preparation is shown in the graph in FIG. 3. Large particles (>40 mesh) and very small particles (<140 mesh) are generally not suitable for proper encapsulation and can be removed by screening. In order to increase the flow properties of the encapsulated pancreatic enzyme preparation, digestive enzyme particles can be sieved to remove fines and overly large particles, for example by including only particles of sizes 40-140 mesh, or about 105 to 425 microns. In some embodiments, the coated digestive enzyme preparation containing 80% digestive enzyme by weight is made by coating sieved pancreatic enzyme particles with a hydrogenated vegetable oil using 20 lbs. of enzyme particles and 5 lbs of hydrogenated vegetable oil.

In some embodiments, the temperature of the lipid or lipid blend is maintained at 110° F. before application to the digestive enzymes, which are not heated.

In some embodiments, the lipid should be present in the preparation at a minimum amount of about 5% by weight of the encapsulated composite, preferably about 30%, and more preferably about 50% by weight of the encapsulated composite. The maximum amount of pancreatic/digestive enzyme present in the encapsulated composite is about 95% by weight of the composite, preferably about 90%, and more preferably about 85% of the encapsulated composite. The emulsifiable lipid can be any lipid or lipid-derived material that emulsifies or creates an emulsion yet has a melting point which allows the emulsifiable lipid to be a solid at typical storage temperatures, for example, 23 degrees Centigrade.

"Emulsifiable lipids" as used herein means those lipids which contain at least one hydrophilic group and at least one hydrophobic group, and have a structure capable of forming a hydrophilic and hydrophobic interface. These chemical and/or physical properties, mentioned above, of an emulsifiable lipid permit emulsification. Examples of interfaces include, for example, micelles and bilayers. The hydrophilic group can be a polar group and can be charged or uncharged.

The emulsifiable lipid can be derived from animal or vegetable origins, such as, for example, palm kernel oil, soybean oil, cottonseed oil, canola oil, and poultry fat, including hydrogenated type I vegetable oils. In some embodiments, the lipid is hydrogenated. The lipid can also be saturated or partially saturated. Examples of emulsifiable lipids include, but are not limited to, monoglycerides, diglycerides, fatty acids, esters of fatty acids, phospholipids, salts thereof, and combinations thereof.

The emulsifiable lipid is preferably a food grade emulsifiable lipid. Some examples of food grade emulsifiable lipids include sorbitan monostearates, sorbitan tristearates, calcium stearoyl lactylates, and calcium stearoyl lactylates. Examples of food grade fatty acid esters which are emulsifiable lipids include acetic acid esters of mono- and diglycerides, citric acid esters of mono- and di-glycerides, lactic acid esters of mono- and di-gylcerides, polyglycerol esters of fatty acids, propylene glycol esters of fatty acids, and diacetyl tartaric acid esters of mono- and diglycerides. Lipids can include, for example, hydrogenated soy oil.

Any emulsifiable lipid may be used in the methods and products of this invention. In certain embodiments the emulsifiable lipid used will produce non-agglomerating, non-aerosolizing enzyme preparation particles.

In other embodiments, the method relates to preparation of an encapsulated, controlled release digestive enzyme preparation with enhanced flow properties useful in the treatment of individuals with autism, ADD, ADHD, Parkinson's' Disease, Cystic fibrosis and other neurological conditions, the method comprising: a) blending an emulsifiable lipid with one or more additives to obtain a blend; and b) coating screened digestive enzyme with the blend to form an encapsulated digestive enzyme containing a core which contains the digestive enzyme and a coating which contains the blend of emulsifiable lipid.

Figure 2:
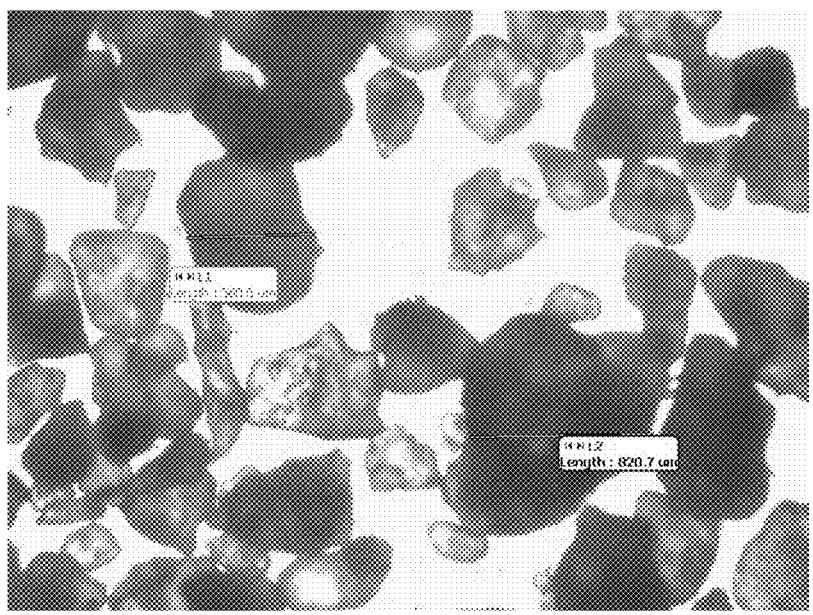
FIG. 2 shows an electron micrograph of a coated enzyme preparation following sieving and lipid coating of the raw digestive enzyme preparation.

The coating of the enzyme with the lipid, as shown in FIG. 2, allows for the enzyme to become more uniform in size and shape, but reduces the jagged edges associated with the raw enzyme, and allows for ease of administration and ease of manufacturing, as the flow properties associated with the covered enzyme will allow for the manufacturing machinery to easily fill the sachet/pouch with the enzyme and reduces overfilling or under filing of the sachet. The unit dose packaging reduces the ability of the child to open the multi dose can/box/or other container. The trilaminar foil pouch or sachet further reduces the ability of a child to open the sachet/pouch, and over utilize the enzyme.

In another embodiment, the invention relates to a method of controlling the rate of release of a digestive enzyme from the encapsulated preparation by using a lipid blend to coat the digestive enzyme. The method includes blending an emulsifiable lipid with one or more additives to obtain a blend, and coating the digestive enzyme with the blend to form an encapsulated digestive enzyme containing a core which contains the digestive enzyme and a coating which contains the blend of emulsifiable lipid. The rate of release of the enzyme from the encapsulated preparation upon exposure with a solvent is decreased as the amount of additive is increased. In the alternative, the rate of release of the enzyme from the encapsulated composite upon exposure with a solvent is increased as the amount of additive is decreased. Thus, the nature of the coating allows for controlled release of the enzyme from the encapsulate.

Non-emulsifiable lipids do not possess the chemical and/or physical properties related to emulsification as described above and include any lipid, lipid derived material, waxes, organic esters, or combinations thereof. Non-emulsifiable lipids generally do not emulsify by themselves. Non-emulsifiable lipids can be used as additives so long as the properties of the coating, and constituent lipids, permit emulsification. Non-emulsifiable lipids, such as, for example, triglycerides, can be blended with an emulsifiable lipid of the present invention. The non-emulsifiable lipid can be derived from animals, vegetables, mineral, or synthetic origins. The non-emulsifiable lipid is preferably hydrogenated, and can be saturated or partially saturated, and includes, but is not limited to triglycerides. In a preferred embodiment, the coating contains a blend of monoglycerides and triglycerides applied to a pancreatic/digestive enzyme.

The inclusion of one or more additives with an emulsifiable lipid of the present invention is used to control emulsification of the coating and release of the enzyme. For example, the additive, triglyceride, can be blended with monoglycerides (e.g., an emulsifiable lipid), to control emulsification of the coating and thus control (e.g., decrease) the rate of release of the enzyme from the composite. As a further example, one or more additives, such as a diglyceride and a triglyceride can be blended with the emulsifiable lipid to control the rate of release of the enzyme. Hydrogenated vegetable oils may contain emulsifying agents, such as soy lecithin or other components.

Properties including mechanical strength, melting point, and hydrophobicity can be considered when choosing a suitable lipid coating for the digestive enzyme. Lipids having lower melting points or more polar, hydrophilic properties were generally less suitable for encapsulation because they resulted in product that would cake under accelerated storage stability conditions. Enzyme preparations made using, for example, hydrogenated soy oil, hydrogenated castor wax, and carnauba wax all demonstrated good pouring and no caking.

The wax can be paraffin wax; a petroleum wax; a mineral wax such as ozokerite, ceresin, or montan wax; a vegetable wax such as, for example, carnuba wax, bayberry wax or flax wax; an animal wax such as, for example, spermaceti; or an insect wax such as beeswax.

Additionally, the wax material can be an ester of a fatty acid having 12 to 31 carbon atoms and a fatty alcohol having 12 to 31 carbon atoms, the ester having from a carbon atom content of from 24 to 62, or a mixture thereof. Examples include myricyl palmitate, cetyl palmitate, myricyl cerotate, cetyl myristate, ceryl palmitate, ceryl certate, myricyl melissate, stearyl palmitate, stearyl myristate, and lauryl laurate.

In a further embodiment, the invention provides a method for controlling rate of release of a pancreatic/digestive enzyme from an encapsulated composite upon exposure to a solvent. The method includes coating the enzyme with an amount of an emulsifiable lipid to form an encapsulated pancreatic enzyme substance composite, wherein the rate of release of the enzyme from the encapsulated composite is decreased as the amount of emulsifiable lipid based on total weight of the encapsulated composite is increased. In the alternative, the rate of release of the pancreatic enzyme from the encapsulated composite is increased as the amount of emulsifiable lipid based on total weight of the encapsulated composite is decreased. The emulsifiable lipid useful in this embodiment can consists essentially of one or more monoglycerides.

The solvent in which a lipid emulsifies can be an aqueous solvent. The aqueous solvent interacts with the hydrophilic groups present in the emulsifiable lipid and disrupts the continuity of the coating, resulting in an emulsion between the aqueous solvent and the lipids in the coating, thus releasing the bioactive substance from the composites.

The methods herein, used to encapsulate pancreatic or digestive enzyme cores for treatment of neurological conditions or disorders, has not been previously described. The methods for lipid encapsulation of medications for human consumption which have the characteristics of a time-released medication, and which utilize the lipid encapsulation for stability have not been previously described. Prior to the experiments described herein, there was no published protocol that allowed for the preparation of an encapsulated enzyme preparation comprising a coating of emulsifiable lipid and a digestive enzyme suitable for the time-specific arid/or site-specific targeted release along the GI tract for the treatment of autism, ADD, ADHD, Parkinson's Disease and other neurological or behavioral conditions susceptible to treatment with digestive enzymes.

Aspects and embodiments of the instant disclosure stem from the surprising and unexpected discovery that certain pharmaceutical dosage preparations comprising a coating of emulsifiable lipid and a digestive enzyme can have novel potentiated activity and unexpected favorable release and dissolution profiles and absorption kinetic parameters along the various portion of the GI tract. These characteristics are useful for formulating a specific bioactive enzyme for site specific targeted release along the GI tract for the treatment of autism, ADD, ADHD, Parkinson's Disease and other neurological conditions.

Determination of whether a subject is in need of treatment with an effective amount of digestive enzymes may be based on a determination that the subject has an enzyme deficiency.

In one aspect of the invention, the method comprises using the enzyme formulations of this invention to treat children and other individuals with autism, ADD, ADHD, Parkinson's disease and other neurological diseases or conditions, who also have an enzyme deficiency. The enzyme deficiency could be determined by any method used in determining or diagnosing an enzyme deficiency. In one aspect the determination or diagnosis may be made by evaluating symptoms, including eating habits, self-imposed dietary restrictions, symptoms of eating disorders and/or gastrointestinal disorders. In other aspects, the determination may be made on the basis of a biochemical test to detect, for example, levels or activities of enzymes secreted, excreted or present in the GI tract, and/or by determining the presence of a mutation in a gene or aberrant expression of a gene encoding one or more digestive enzymes. The enzyme deficiency may also be determined, for example, by detecting a mutation or aberrant expression of a gene encoding a product regulating or otherwise affecting expression or activity of one or more digestive enzymes.

In some aspects, the individual to be treated may also be tested for the presence of a co-morbidity, which is a co-morbidity which does not affect the activity or expression of a digestive enzyme. In certain aspects, individuals who are determined to have autism based on clinical symptoms but not a co-morbidity such as a genetic co-morbidity, are treated with the enzyme delivery systems described herein. However, individuals who are determined to have autism based on clinical symptoms and a co-morbidity, who nevertheless also test abnormally low for FCT level or positive using another indicator of GI pathogens and/or low digestive enzyme activity or expression may also be treated with the enzyme delivery systems of this invention.

The following co-morbidities are set forth as exemplary co-morbidities:
Fragile X
Hallermann-Streiff syndrome Trisomy 21
tranlocation on 9
Beckwith-Wiedemann syndrome
Trisomy 21
Trisomy 18
Rubenstein-Tabi syndrome
Fragile X
Prader-Willi syndrome
Trisomy 21
Rett syndrome Klippel-Feil syndrome
Rett syndrome
Duchenne Muscular Dystrophy
Tourette syndrome
In-utero stroke Trisomy 21
Fragile X
Juvenile RA
In-utero stroke
Trisomy 6
Duchenne Muscular Dystrophy
Juvenile Diabetes
Diabetes Type I
Adrenoleukodystrophy
Wilson's disease
In-utero stroke
Diabetes Type I
Prader-Willi syndrome
22q13
Tourette syndrome
Lissencephaly
Neutrophil Immunodeficiency syndrome
Diabetes Type I
Tourette syndrome
Tetrasomy 18p
Hyper IgE syndrome
Angelman Syndrome
Diabetes Type I
Rett syndrome
Fragile X
Marfan syndrome
Waardenburg syndrome
glutathione synthetase deficiency
Diabetes Type I
Rubinstein-Taybi
Angelman Syndrome
Klinefelter Syndrome
Brain bleed at birth
Turner Syndrome
Hypothyroidism
Diabetes Type I
Brain damage of prematurity In One aspect, the determination of an enzyme deficiency may be made using a test for fecal chymotrypsin levels. Methods such as PCR or other amplification, SNP detection, sequencing, and/or DNA combing may be used to detect the presence of a mutation or presence of short RNA sequences which interfere with expression of one or more genes encoding a digestive enzyme. For example, the mutation may in a gene encoding a digestive enzyme which decreases or eliminates the activity of the enzyme. As another example, the mutation may be mutation in the MET gene, a gene encoding the pleiotropic MET receptor tyrosine kinase See Campbell et al., PNAS 103(46), 16834-39 (2006). These mutations may include, for example, the MET promoter variant rs1858830 C allele, and or mutations in the MET signaling pathway such as a haplotype of the SERPINE1 gene, or the rs 344781 PLAUR promoter variant T allele.

The enzyme formulations of this invention are suited for use in delivering digestive enzymes to individuals with autism, ADD, ADHD, Parkinson's disease and other neurological diseases or conditions in need of enzyme treatment. Fallon has described certain methods and enzyme compositions for use in treating children and other individuals, with autism, ADD, ADHD, Parkinson's disease and other neurological diseases or conditions, for example, U.S. Pat. Nos. 7,138,123, 6,660,831, 6,632,429, 6,534,063, hereby incorporated by reference as if set forth in full herein.

The present invention will now be described more fully with reference to the accompanying figures and examples, which are intended to be read in conjunction with both this summary, the detailed description, and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete, and will fully convey the full scope of the invention to those skilled in the art.

In the experiments described herein, several factors were discovered that allowed for the unexpected enhanced/potentiated efficacy and property. For example, it was discovered that certain encapsulation enzymatic preparations comprising soy oil exhibited certain surprising characteristics that led to improvements in the site-specific activity, release/dissolution profile, and ease of manufacturing, packaging and storage. Without being bound to a particular theory of operation, the skilled artisans will appreciate that other methods of sample preparation and/or formulation that can also yield these advantageous parameters are also contemplated herein.

The following experiments describe exemplary procedures in accordance with the invention. It is to be understood that these experiments and corresponding results are set forth by way of illustration only, and nothing therein shall be construed as a limitation on the overall scope of the invention. By way of example, these studies demonstrate some of the unexpected improvements realized by the exemplary encapsulated enzyme preparations of the present disclosure.

Example 1

Increased Flow Properties and Pourability of an Exemplary Encapsulated Digestive Enzyme Preparation Before the exemplary methods and preparations of the present disclosure is applied, examination of an unprocessed, raw enzyme preparation (Scientific Protein Laboratories (SPL) of Wanakee, Wis.) revealed that it contained significant variability in particle size and 20 irregular morphology, as shown in an electron micrograph of the particles as pictured in FIG. 1. Some crystalline salt particles are also visible. The raw enzyme does not pour as it clumps and is difficult to measure due to the uneven surfaces, and jagged edges. The raw preparation is also not suitable for lipid encapsulation without further processing because the raw product contains particles both too large and too small for proper encapsulation. The sieved enzyme, while more uniform in size, continues to exhibit uneven surfaces and clumps while pouring.

FIG. 2 shows the coated enzyme preparation produced following sieving and lipid coating of the raw material. In this example, the morphology of particles is significantly improved, with rounder surfaces. This leads to a non-dusty product with good flow and organoleptic properties.

The morphology of the enzyme is now greatly improved due to the rounding of the surfaces, which leads to a product which is less dusty, does not aerosolize and has good flow and improved organoleptic properties.

The size distribution of particles in the raw enzyme preparation is shown in the graph in FIG. 3. In general, large particles (>40 mesh) and very small particles (<140 mesh) are not suitable for proper encapsulation. In order to increase the flow properties of the encapsulated pancreatic enzyme preparation, the raw enzyme particles were sieved to include only particles of sizes 40-140 mesh, or about 106 to 425 microns.

Example 2

Stability of an Exemplary Encapsulated Digestive Enzyme Preparation: Temperature Storage In a further exemplary embodiment, multiple types and weight percentages of lipids were used to coat the sieved enzyme cores. Properties including mechanical strength, melting point, and hydrophobicity were taken into consideration in choosing a suitable lipid coating for the pancreatic enzyme. Multiple examples of lipid coatings were examined below and their physical appearances were examined under 25° C. and at 40° C. Accordingly, lipids with a range of physical properties such as mechanical strength, melting point and hydrophobicity were evaluated for coating of the pancreatic enzymes. In this example, it was found that the decreasing the melting point or increasing the hydrophilicity of the coatings were not suitable for encapsulation because they resulted in product that would cake under accelerated storage stability conditions. The sieved and encapsulated enzyme preparations made using hydrogenated soy oil, hydrogenated castor wax, and carnauba wax all demonstrated good pouring and no caking.

Table 1 provides the results of the visible physical changes which occurred at 25° C. and 40° C.:

| Coating System | Physical Appearance at 25° C. storage | Physical Appearance at 40° C. storage |
|---|---|---|
| Hydrogenated Soy oil (Balchem/Alibec) | OK | OK |
| Hydrogenated Castor wax | OK | OK |
| Carnauba Wax | OK | OK |
| Hydrogenated Monoglycerides | OK | Some Caking |
| Soy/Monoglceyride blends | OK | Some caking |

Both the hydrogenated monoglycerides and the soy oil/monoglyceride blends demonstrated caking at the higher temperature. Therefore it is clear that the lower melting or more hydrophilic coatings were not suitable for encapsulation because they resulted in a product that would cake under extended storage conditions as evidenced by our accelerated storage condition test at 40 degrees Centigrade.

Both the hydrogenated monoglycerides and the soy oil/monoglyceride blends demonstrated caking at the higher temperature. Therefore it is clear that decreasing the melting point or increasing the hydrophilicity of the coatings were not suitable for encapsulation because they resulted in a product that would cake under extended storage conditions as evidenced by our accelerated storage condition test at 40 degrees Centigrade.

Example 3

An Exemplary Encapsulated Digestive Enzyme Preparation Suitable for Pancreatic Enzymes: Enzyme Activity Measured as a Function of Stability In a further embodiment, enzyme stability was determine according to the following method: For the accelerated test, standard ICH guidelines were used: the coated preparations were placed in a plastic container, which was stored in a controlled humidity cabinet at 40° C. and 75% relative humidity. Enzymatic activity was measured by grinding the coated enzyme preparations, dispersing in appropriate buffers, and testing for lipase activity.

TABLE 2

PERCENT STABILITY OF ENCAPSULATED ENZYMES WHEN STORED AT 40 C/75% RH, IN CLOSED CONTAINERS

| Sample | Lot# or coat | Activity RT | Activity 1 week Capped | Activity 2 weeks Capped | Activity 1 Month capped |
|---|---|---|---|---|---|
| PEC raw Nov '06 | 1206-1369A | 116% | 126% | | 75% |
| PEC encap 70%, monoglyceride | R1C-0890 | 118% | 112% | | |
| PEC encap 50%, soy/mono | R1C-0891 | 116% | 110% | | 88% |
| PEC raw Jan '07 | 1206-1382B | 113% | | | 61% |
| PEC encap 70% carnuba | R1C-0898 | | | | |
| PEC encap 50% carnuba | R1C-0898 | | | | 68% |
| PEC encap 70%, castor wax | castorwax | 108% | | 78% | 87% |
| PEC encap 80%, soy | soy | 99% | | 89% | 87% |

As illustrated above in the data summarized in Table 2, the soy oil 80% appeared to impart the greatest amount of stability of all the lipids, an effect that surprisingly was greater for enzyme preparations stored in capped containers than in uncapped containers. Tests of stability for 75% relative humidity enzyme preparations stored at 40° C. in open pans did not show significant differences in stability between coated and uncoated preparations.

Example 4

An Exemplary Encapsulated Digestive Enzyme Preparation Suitable for Pancreatic Enzymes: Enzyme Activity and Rate of Release of Multiple Soy Encapped Pancreatic Enzyme In a further embodiment, encapsulates were prepared according to the methods described below. The raw enzyme material was sieved to obtain particles smaller than 40 mesh but larger than 140 mesh, to remove fines, and to obtain a more uniform mixture more suitable for enteric coating.

The following preparations were made:
70% active enzyme by weight, with a standard stable soy coating;
80% active enzyme by weight, with a standard stable soy coating; and
90% active enzyme by weight, with a standard stable soy coating.

Activity in each encapsulated enzyme preparation was measured by grinding the encapsulates, dispersing the ground material in appropriate buffers, and testing for lipase activity.

Figure 4:
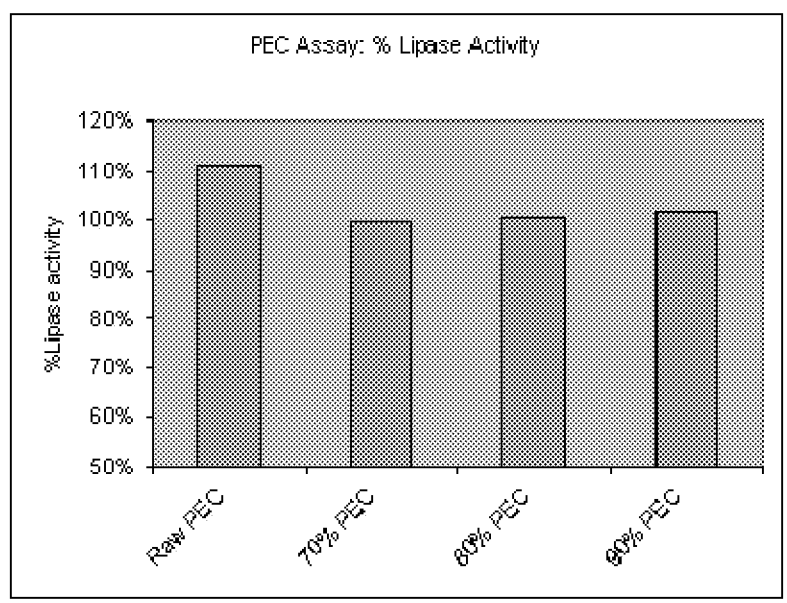
FIG. 4 shows a bar graph of the % lipase activity in the raw digestive enzyme particles, and following encapsulation, for coated enzyme preparations containing 70%, 80% and 90% digestive enzymes by weight.

As shown in FIG. 4, the enzyme activity in the coated preparations does not show any significant loss of activity upon coating (decrease from 110 to 100% activity, normalized to stated enzyme activity of the raw enzyme material).

Figure 5:
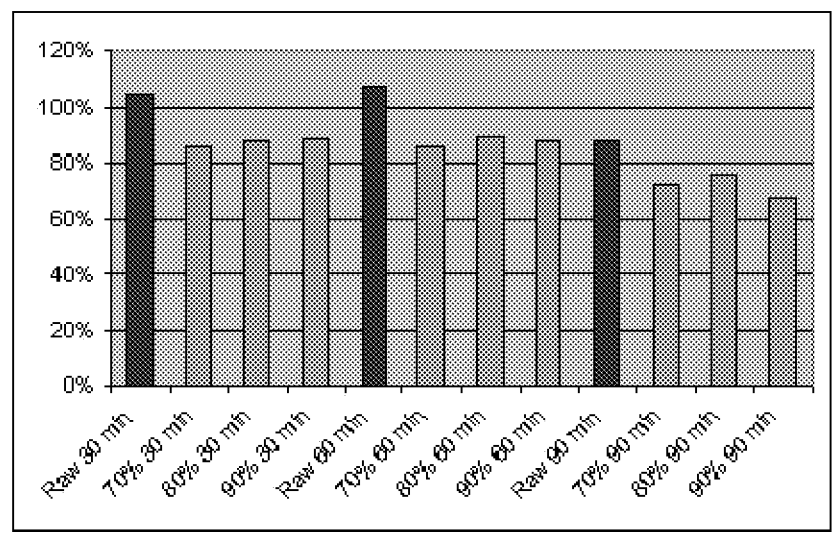
FIG. 5 shows a bar graph of the % enzyme release for the enzyme preparations containing 70%, 80% and 90% digestive enzymes by weight, at the times indicated on the x-axis.

Enzyme release was measured by suspending each encapsulate in a dissolution apparatus at pH 6.0 buffer for 30, 60, and 90 minutes (100 rpm, as per USP guidelines). As shown in FIG. 5, all encapsulates show between 80-90% release at 30 and 60 minutes. At 90 minutes, the measured enzyme activity obtained with these preparations decreases.

Example 5

Figure 6:
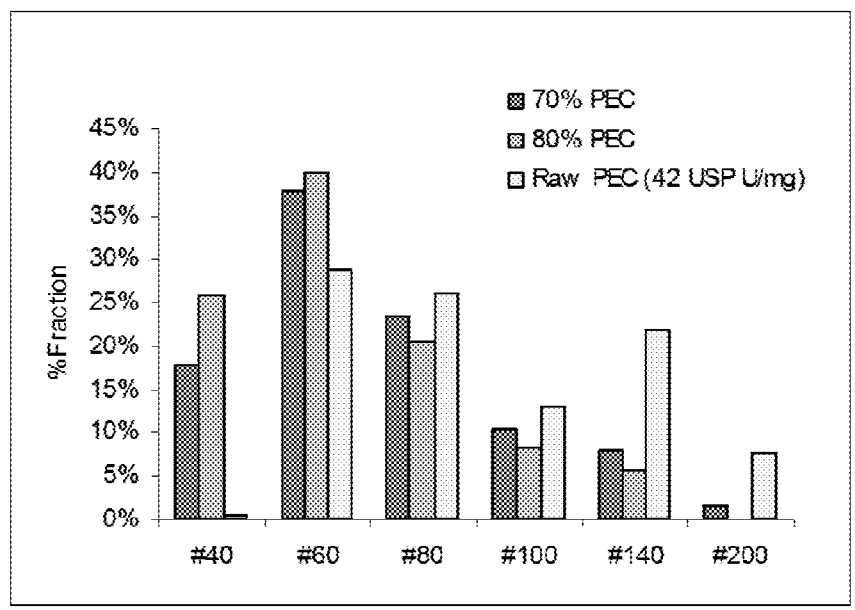
FIG. 6 shows a bar graph of the particle size distributions of the raw digestive enzyme particles compared with the particle size distributions in coated enzyme preparations containing 70% or 80% digestive enzymes by weight.

An Exemplary Encapsulated Digestive Enzyme Preparation Suitable for Pancreatic Enzymes: Particle Size of Multiple Soy Oil Encapped Pancreatic Enzyme In a further embodiment, preparations containing 70% or 80% active pancreatic enzyme by weight, encapsulated with soy oil were compared to raw pancreatic enzyme material with respect to particle size, as shown in FIG. 6.

All levels of lipid demonstrate an impact of particle size. The 80% PEC demonstrates the most uniform as none appear at the 200 mesh level.

Example 6

An Exemplary Encapsulated Digestive Enzyme Preparation Suitable for Pancreatic Enzymes: Smell and Taste Examination of exemplary encapsulated enzyme preparations containing 70%, 80% and 90% enzyme by weight were performed to determine their taste and smell when compared to Sucanat™ and brown sugar, as well as compared to the raw enzyme. The results are shown in Table 4, below. Sucanat™ is an organic whole food sweetener.

TABLE 4

| SUBSTANCE | ODOR | TASTE |
|---|---|---|
| Brown sugar | Yes | Sweet |
| Sucanat ™ | No | Sweet |
| Raw Enzyme | Meaty/smoky | N/A |
| 70% | No | No |
| 80% | No | No |
| 90% | Slight | Salty |

Example 7

Figure 7:
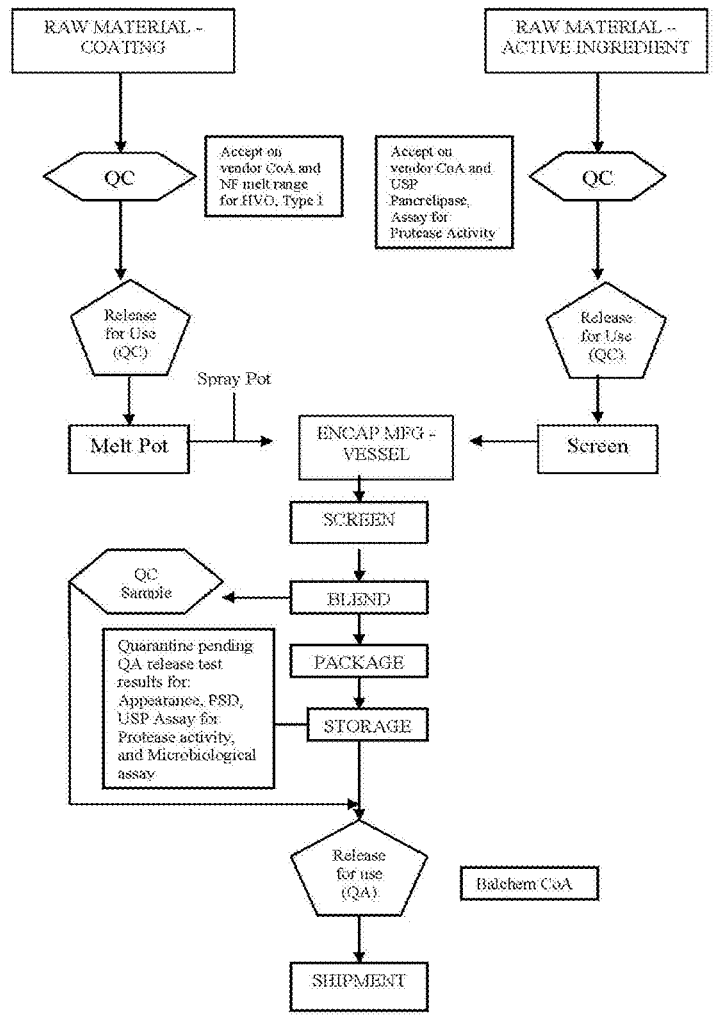
FIG. 7 shows the flow chart for a process that can be used to encapsulate digestive enzyme particles.
Figure 8:
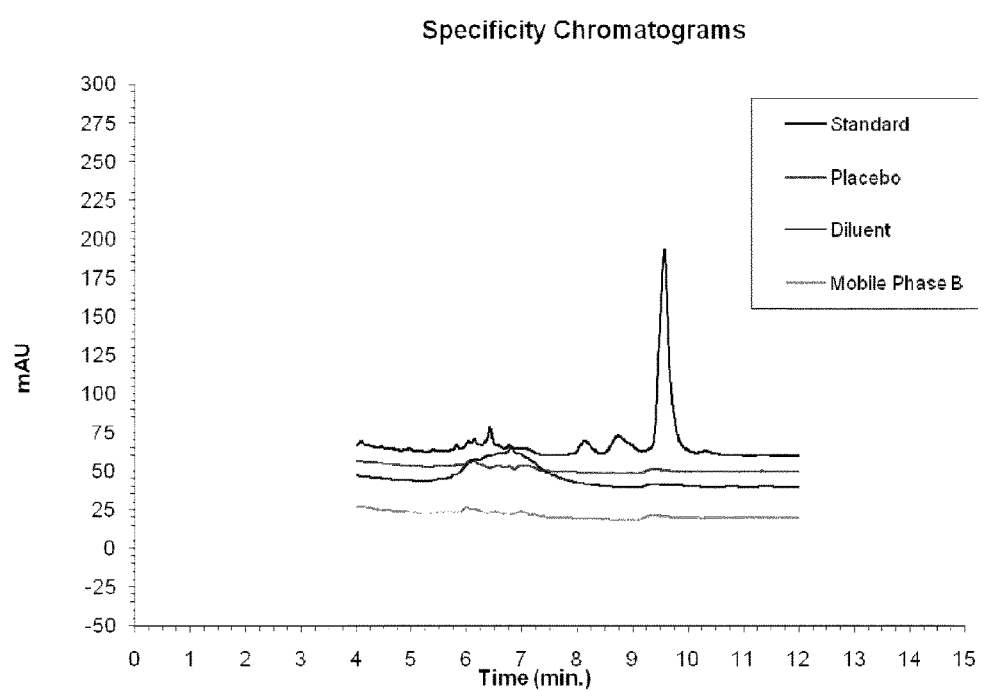
FIG. 8 shows a chromatogram of peak area (mAU) vs. time for working standard (top line), diluent (line that starts third from the top when time is 4 minutes), mobile phase used in the HPLC (bottom line at 4 minutes) and placebo (second to the top line when time is 4 minutes), which demonstrate no interference with the standard trypsin peak.

An Exemplary Encapsulated Digestive Enzyme Preparation Suitable for Pancreatic Enzymes: Manufacturing The flow chart outlining the manufacturing process useful in making the enzyme preparations of this invention is shown in FIG. 7.

Ingredients used in making a batch of an exemplary encapsulated pancreatic enzyme preparation included 20.0 lb. of sieved pancreatic enzyme and 5.0 lb. of hydrogenated vegetable oil, for example, soy oil.

The pancreatic enzyme concentrate was first sieved through a 40 USSS mesh screen, and the material which passed through the mesh was retained. The retained material was then screened through a 140 USSS mesh screen (or the equivalent), and the material which did not pass through the mesh was retained as the sieved pancreatic enzyme material or particles.

In the encapsulation process, the appropriate coating material is charged to the melt pot, and brought to and maintained at 110° F. for the spraying process. Any temperature that will provide appropriate consistency during the spraying process may be used. In some embodiments, the temperature is further selected based on the melting points of the lipids used in the coating, and/or so that after contact of the sieved pancreatic enzyme material or particles with the coating, the activity of the enzyme preparation remains about the same.

The liquefied coating material is weighed and transferred to the spray pot. The sieved pancreatic enzyme was added to the encapsulation manufacture vessel. The pancreatic enzyme particles are encapsulated with coating material to the selected coating level.

The encapsulated material is screened with a 14 USSS mesh screen (or equivalent), and the material that passes through the screen is retained. Following sieving, the material is collected and samples are removed for QC.

If two sub-batches are to be blended, the loaded screened material is added to a suitable blender and blended for 7 to 10 minutes. Samples are obtained for finished product testing. The encapsulated material is bulk packaged and placed in quarantine pending test results. Upon achieving acceptance criteria, the finished product is released by the Quality group. Afterwards, the product may be shipped as directed.

Samples are collected for finished product testing, including analytical testing and microbial assays, which can be tested over time.

Example 8

An Exemplary Encapsulated Digestive Enzyme Preparation Suitable for Pancreatic Enzymes: Packaging In yet another further embodiment, the stability of the enzyme is due in part to the encapsulation and in part to the trilaminar foil packaging. The following demonstrates the packaging process for the single dose sachets/pouches.

First, following manufacture the product is dispensed into clean, drums double lined with food-grade polyethylene bags, and the drums are sealed. If specification criteria are met, the lot is then released from quarantine, and the material is then shipped to a suitable packager for placement into sachets for individual dosing to the patient.

For example a PD-73272 Printed Child Resistant (CR) Pouch consisting of 26#C1S Paper/7.5#LDPE/0.0007" Aluminum Foil/15# with a Surlyn liner is utilized for packaging. Preferably pre-printed film/foil, exterior printing will be with 1 color eye-mark on white background while in-line printing of lot number, expiration date and product code will also be in 1 color, black. Overall sachet dimension are: W 2.50"×H 3.50". The sachet is sized to hold 900 mg of granules of Pancrelipase lipid-encapsulated drug product with a tolerance of ±10% into a unit dose pouch/sachet. The final product will have a protease activity of not less than 156 USP units/mg.

Example 9

An Exemplary Encapsulated Digestive Enzyme Preparation Suitable for Pancreatic Enzymes: Dissolution The effect of the release of Pancreatase from lipid encapsulated particles with soy oil was studied using particles with varying levels of lipid coating (expressed as % lipid coating per total particle weight. The coating level was varied from 10% to 30%. There was no significant effect of lipid coating in this range on the release of pancreatase in an aqueous environment from the particles over a 60-minute period. All formulations release over 80% of the enzyme within the first 30 minutes following the initiation of dissolution. Maximum release for the 90%, 80% and 70% particles was 85%, 88% and 83% respectively by 60 minutes.

Example 10

An Exemplary Enzyme Delivery System for Treatment of Autism

The choice of 70%-90% encapsulated pancreatic enzyme preparation (active enzyme by weight) was selected on the basis of its release profile, as suitable for release of the enzyme in the proximal small intestines where protein digestion by the protease component will take place.

Soy oil was selected as the lipid coating, for its lack of protein components, and corresponding lack of antigenic properties, to minimize or eliminate the possibility of an allergic reaction to the lipid coating in treated patients and children with autism.

The use of the 70-90% preparation increases pourability and flow properties while decreases aerosolization, which permits use of a sachet or pouch delivery system.

The addition of the trilamminar foil housing insures that the sprinkle formulation will be stable, transportable, and will be delivered by a single unit dose mechanism.

The low lipase formulation allow also for the safety by reducing the potential for colonic strictures, and enhances the utilization of the protease portion of the enzyme.

TABLE 5

Composition of LUMINENZ-AT encapsulated digestive enzyme preparation, 900 mg Sachets

| Ingredients | Compendial Status | Functions | Content |
| --- | --- | --- | --- |
| Pancreatic enzyme concentrate (porcine origin) | USP | Active ingredient | NLT 156 USP units/mg |
| Hydrogenated vegetable oil, Type I (soybean oil) | NF | Lipid coating material | q.s. |

The drug substance, pancreatic enzyme concentrate (porcine origin) is purchased from an appropriate supplier. The properties of the pancreatic enzyme concentrate (pancreatin/pancrelipase) suitable for use in the products of this invention are described in the table below.

TABLE 6

| Parameter | USP Specification |
| --- | --- |
| Protease (USP) | NLT 25 USP Units/mg |
| Lipase (USP) | NLT 2 USP Units/mg |
| Amylase (USP) | NLT 25 USP Units/mg |
| Fat (USP) | NMT 6.0%* |
| Loss on Drying (USP) | NMT 5.0% |
| Escherichia coli (USP) | Neg/10 g |
| Salmonella species (USP) | Neg/10 g |

*If less than 75 U/mg Protease, 6 U/mg Lipase or 75 U/mg Amylate, then specification is NMT 3.0%

Specifications for Hydrogenated Vegetable Oil (Soy Oil)

Physical Appearance and Sensory Characteristics:

Material provided in flake or powder form, free from foreign matter and objectionable odor.

TABLE 7

| | Specification | Analytical Procedure |
| --- | --- | --- |
| Chemical Parameter | | |
| Melting Range | 67 to 69 C | USP/NF <741> Class II |
| Acid Value | 0.4 Max. | USP/NF <401> |
| Iodine Value | 5.0 Max. | USP/NF <401>Method II |
| Loss on drying | 0.1% Max. | USP/NF <731> |
| Saponification Value | 175-200 | USP/NF <401> |
| Heavy Metals | 0.001% Max. | USP/NF <231> |
| Organic Volatile Impurities | Complies | USP/NF <467>Method IV |
| Residual Solvents | Complies | USP/NF <467> |
| Unsaponifiable Matter | 0.8% Max. | USP/NF <401> |
| Microbial Parameters | | |
| Total Aerobic Microbial Count | 2000 cfu/g max. | USP/NF <61> |
| Staphylococcus aureus | Absent in 10 g | USP/NF <61> |
| Pseudomonas seruginosa | Absent in 10 g | USP/NF <61> |
| Salmonella Species | Absent in 10 g | USP/NF <61> |
| Escherichia coli | Absent in 10 g | USP/NF <61> |
| Mold and yeast | 200 cfu/g max. | USP/NF <61>. |

Figure 9:
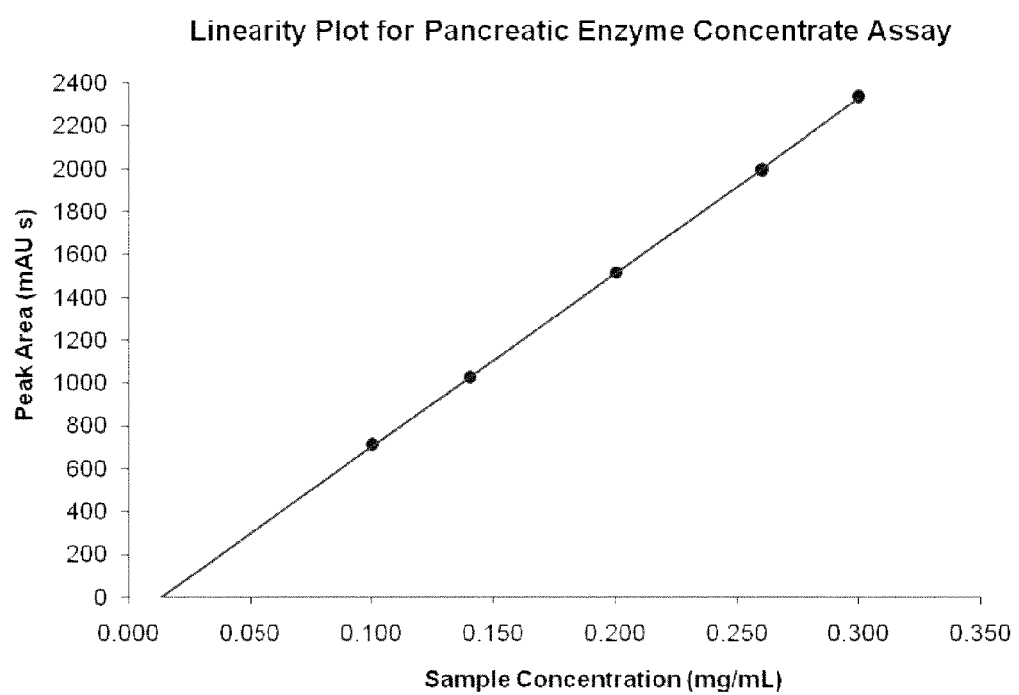
FIG. 9 shows a graph of peak area (mAU) vs. sample concentration (mg/mL) for known trypsin concentrations obtained using HPLC to measure trypsin in the coated digestive enzyme preparation.

Chromatograms of working standard, diluent, mobile phase B, and placebo demonstrate no interference with the standard peak (see Chromatogram, FIG. 9). The analytical placebo and active tablet compositions are given in Table 8.

TABLE 8

Composition of Analytical Placebo and Active Powder

| Formulation Ingredients | Analytical Placebo mg/sachet | Active mg/sachet |
| --- | --- | --- |
| Pancreatic enzyme concentrate | — | 720.0 |
| Lipid encapsulate | 180.0 | 180.0 |
| Total | 180.0 | 900.0 |

The method linearity was evaluated by analyzing several sample levels of the standard concentration in the presence of the placebo matrix. These levels were 50%, 70%, 100%, 130%, and 150%. Three injections of each sample were used to calculate the average response (area/concentration) for that level. Then the relative standard deviation for the generated response ratios was calculated along with the least-squares linear regression statistics for the average peak area vs. concentration (see Tables 9 and 10). A plot of the average peak area vs. concentration with the linear regression line is given in FIG. 10.

TABLE 9

Linearity Data

| Standards | | Peak Area (mAU s) | | | Average Peak Area | Average |
| --- | --- | --- | --- | --- | --- | --- |
| mg/mL | % | Injection 1 | Injection 2 | Injection 3 | (mAU s) | Response |
| 0.100 | 50 | 709.4 | 712.9 | 710.5 | 710.9 | 7109.3 |
| 0.140 | 70 | 1041.2 | 1040.0 | 1002.9 | 1028.0 | 7343.1 |
| 0.200 | 100 | 1529.0 | 1499.0 | 1523.1 | 1517.0 | 7585.2 |
| 0.260 | 130 | 1969.4 | 2010.3 | 1996.2 | 1992.0 | 7661.4 |
| 0.300 | 150 | 2336.2 | 2322.6 | 2350.6 | 2336.5 | 7788.2 |

TABLE 10

| Parameter | Criterion | Result |
| --- | --- | --- |
| Correlation Coefficient | >0.997 | 0.999 |
| y Intercept | ±2.0% | −112.9 |
| RSD of Response Ratios | <2.0% | 3.6 |
| Visual | Linear | yes |
| Standard error of y intercept | — | 18.8 |
| Slope | — | 8139.1 |

Linearity Results

Example 11

Biochemical Biomarkers, and Behavioral Core and Non-Core Symptoms of Autism

The correlation between digestive enzyme deficiencies in autistic children was determined in children diagnosed with autism based on clinical (behavioral) symptoms. This correlation was also studied in children diagnosed with autism and a genetic co-morbidity. Following the initial discovery that autistic children exhibited self-imposed protein dietary restrictions, studies were conducted which indicated that abnormally low levels of fecal chymotrypsin (FCT) is useful as a biomarker for autism.

In addition, the number of autistic patients responding to pancreatic enzyme replacement was also determined, based on biomarker measurements and clinical symptoms. Changes in the gastrointestinal system as well as a change in the core symptoms of autism were examined. The table below provides an overview of the studies conducted at multiple physician based sites.

TABLE 11

| Study Number | Total # of Subjects | Autism | Non-autism |
| --- | --- | --- | --- |
| 1 | 9 | 9 | |
| 2 | 26 | 26 | |
| 3 | 46 | 25 | 21 |
| 4 | 54 | 54 | |
| 5 | 463 | 266 | 197 |
| 6 | 320 | 64 | 256 |
| 7 | 33 | 33 | |
| 8 | 42 | 25 | 17 |
| 9 | 68 | 68 | |
| 10 | 225 | 225 | |
| 11 | 175 | 175 | |

Initial observations were based on observation of self-imposed dietary restriction by almost all children with autism. Multiple studies were then conducted to evaluate the ability of autistic children to digest protein. A study of the physiology of protein digestion led to an examination of the gastrointestinal system's cascade of digestive enzymes, especially those involved in protein degradation, such as chymotrypsin. As a measure of dysfunction, it was determined that fecal chymotrypsin (FCT) levels in children suffering from autism were abnormally low.

Study 1

Figure 10:
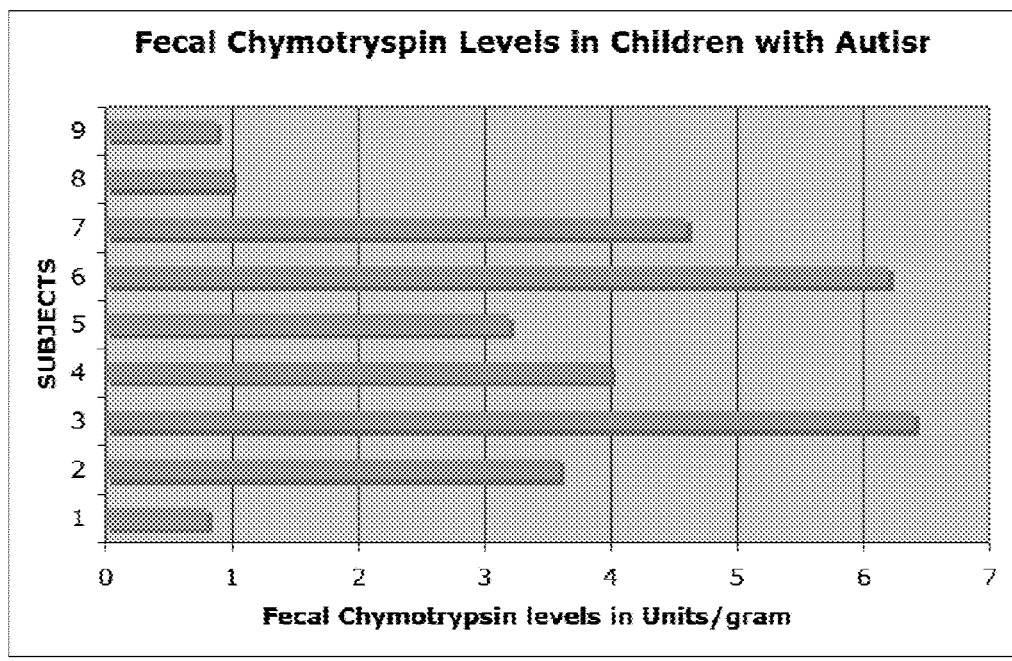
FIG. 10 shows fecal chymotrypsin (FCT) levels measured in nine children with symptoms of autism.
Figure 11:
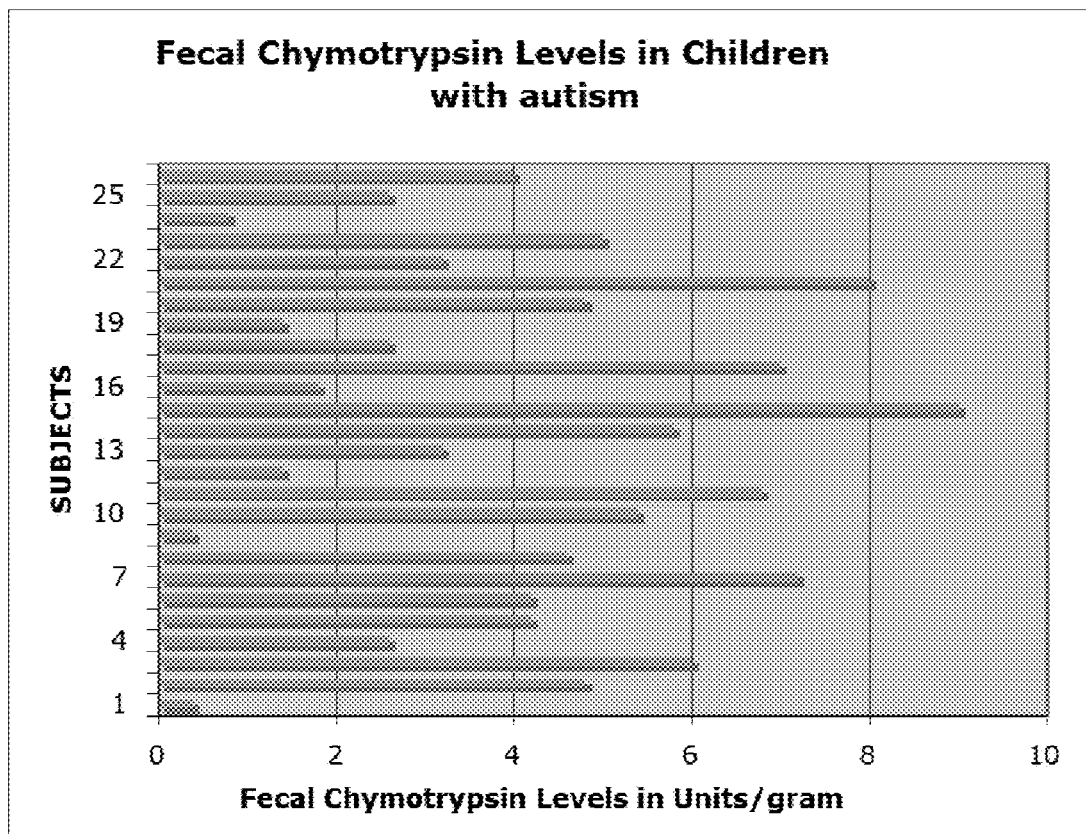
FIG. 11 shows FCT levels measured in 26 children with symptoms of autism.

This initial study was an exploratory one to determine if a small cohort of children with autism indeed would have abnormally low levels (<9.0) of fecal chymotrypsin. (FCT). The results of study 001 is shown in FIG. 10

All 9 children with autism evidenced an abnormally low FCT level of below 7 Units/gram. (Normal≥9.0). This observation in a small set of children led to further examination of the potential for a physiological link to autism heretofore undiscovered.

Study 2

Study 2 was undertaken to determine if a larger cohort of children (26 children) with autism also experienced abnormally low FCT levels. Levels of fecal elastase-1, another pancreatic digestive enzyme present at low amounts in pancreatic insufficiency, was also determined. Again, the levels of FCT were abnormally low in 25 of the 26 children, falling at 8 U/g or below. One child had an FCT level of 9 U/g. On the other hand, all of the children had normal levels of fecal elastase-1.

Study 3

Figure 12:
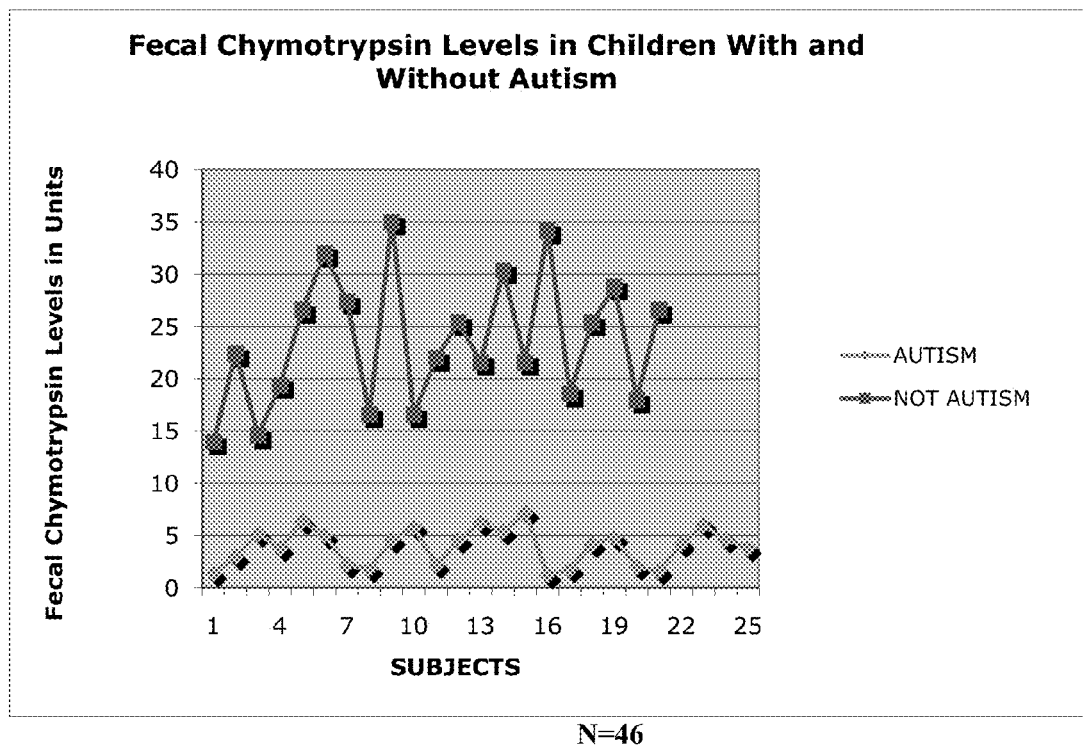
FIG. 12 shows FCT levels measured in 46 children. 25 of the children had symptoms of autism, while 21 children did not have symptoms of autism.

In Study 3, FCT levels were determined in 46 children aged 2 years to 14 years of age, 25 with autism and 21 without autism, The data demonstrated that the children with autism had abnormally low FCT levels and those children who did not have autism had normal FCT levels, of 12 U/g or higher. The results are summarized in FIG. 12. The top line in FIG. 12 shows the FCT levels in subjects who did not have autism, while the bottom line shows the FCT levels in subjects who did have autism.

Study 4

In Study 4, 54 children diagnosed with autism and a co-morbid genetic disorder were examined for FCT levels. The data showed that the children with autism and a co-morbid genetic disorder tested normal for FCT level.

As autism is determined by behavioral assessment, it was hypothesized that autism due to, or present with a known genetic disorder may have a differing physiology from others with autism alone, or not due to a known genetic disorder. Some genetic disorders have typical symptoms, while others may be more variable and overlap with autistic symptomology. This study examined children with autism who were also diagnosed with another known condition, to determine if FCT levels were abnormally low in these children.

Table 12 below represents 54 children diagnosed with autism who also had a genetic co-morbidity

TABLE 12

Children Diagnosed with Autism who also Have a Genetic Co-Morbidity

| | FCT Level U/g | Co-Morbidity |
| --- | --- | --- |
| 1 | 12 | Fragile X |
| 2 | 22 | Hallermann-Streiff syndrome |
| 3 | 25.2 | Trisomy 21 |
| 4 | 15.8 | tranlocation on 9 |
| 5 | 18 | Beckwith-Wiedemann syndrome |
| 6 | 26.6 | Trisomy 21 |
| 7 | 39.2 | Trisomy 18 |
| 8 | 16.6 | Rubenstein-Tabi syndrome |
| 9 | 25.4 | Fragile X |
| 10 | 20.6 | Prader-Willi syndrome |
| 11 | 14.6 | Trisomy 21 |
| 12 | 25.6 | Rett syndrome |
| 13 | 21.4 | Klippel-Feil syndrome |
| 14 | 20.6 | Rett syndrome |
| 15 | 24.8 | Duchenne Muscular Dystrophy |
| 16 | 12.2 | Tourette syndrome |
| 17 | 14.8 | In-utero stroke |
| 18 | 30 | Trisomy 21 |
| 19 | 18.8 | Fragile X |
| 20 | 17.6 | Juvenile RA |
| 21 | 18.8 | In-utero stroke |
| 22 | 34 | Trisomy6 |
| 23 | 22.2 | Duchenne Muscular Dystrophy |
| 24 | 18.8 | Juvenile Diabetes |

TABLE 12-continued

Children Diagnosed with Autism who also Have a Genetic Co-Morbidity

| | FCT Level U/g | Co-Morbidity |
|---|---|---|
| 25 | 28.4 | Diabetes Type I |
| 26 | 13.8 | Adrenoleukodystrophy |
| 27 | 44 | Wilson's disease |
| 28 | 19.6 | In-utero stroke |
| 29 | 7.4 | Diabetes Type I |
| 30 | 23.4 | Prader-Willi syndrome |
| 31 | 14.4 | 22q13 |
| 32 | 15.4 | Tourette syndrome |
| 33 | 17.6 | Lissencephaly |
| 34 | 22.4 | Neutrophil Immunodeficiency syndrome |
| 35 | 18.4 | Diabetes Type I |
| 36 | 32.2 | Tourette syndrome |
| 37 | 14.6 | Tetrasomy 18p |
| 38 | 31 | Hyper IgE syndrome |
| 39 | 26.6 | Angelman Syndrome |
| 40 | 17.4 | Diabetes Type I |
| 41 | 12.6 | Rett syndrome |
| 42 | 34 | Fragile X |
| 43 | 17.4 | Marfan syndrome |
| 44 | 21.2 | Waardenburg syndrome |
| 45 | 21.8 | glutathione synthetase deficiency |
| 46 | 6.0 | Diabetes Type I |
| 47 | 26.6 | Rubinstein-Taybi |
| 48 | 34 | Angelman Syndrome |
| 49 | 25.2 | Klinefelter Syndrome |
| 50 | 21.4 | Brain bleed at birth |
| 51 | 16.8 | Turner Syndrome |
| 52 | 23.4 | Hypothyroidism |
| 53 | 15.8 | Diabetes Type I |
| 54 | 7.8 | Brain damage of prematurity |

Only two of the 54 children diagnosed with both autism and a genetic co-morbidity had abnormally low levels of FCT. Those children had Type I diabetes. 52 of the 54 children registered FCT levels in the normal range.

This further supports that low FCT levels are present in children diagnosed with autism in the absence of another known genetic morbidity.

Study 5

In Study 5, FCT levels were determined for 463 children aged 2 years to 8 years of age, 266 diagnosed with autism and 197 diagnosed without autism, in a multi-office physician-conducted study. The data showed that the children with autism had abnormally low fecal chyotrypsin levels and those children who did not have autism had normal levels of fecal chymotrypsin.

The data is summarized in table 13 below.

TABLE 13

Mean Fecal Chymotrypsin Levels in Children with and without Autism

| N = 463 | Children with Autism | Children not with Autism |
|---|---|---|
| Total numbers of children | 266 | 197 |
| Mean FCT (U/g) | 4.4 | 23.2 |
| Total Children with Abnormal Levels of FCT | 203 | 3 |
| % (p < 0.001) | 76.34% | 1.50% |
| Total Children with Normal Levels of FCT (p < 0.01) | 63 | 194 |
| % | 23.68% | 98.50% |

This data further established that children diagnosed with autism who do not also have a known genetic co-morbidity have abnormally low levels of FCT. FCT levels may therefore be useful in diagnosing children with autism, if the child does not also have a known genetic co-morbidity (unless the co-morbidity is Type I diabetes).

Chymotrypsin is a pancreatic enzyme. Chymotrysin is a serine protease and is unique in that it cleaves only essential amino acids during the digestive process. Specifically, chymotrypsin cleaves the peptide bond on the carboxyl side of aromatic amino acids. A lack of protein digestion as evidenced by abnormal FCT levels leaves the child with a dearth of amino acids available for new protein synthesis. Without sufficient levels of essential amino acids, new proteins required for various bodily functions cannot be synthesized. For example, a shortage or lack of proteins involved in neurological processes may then give rise to symptoms of autism.

Study 6

Figure 13:
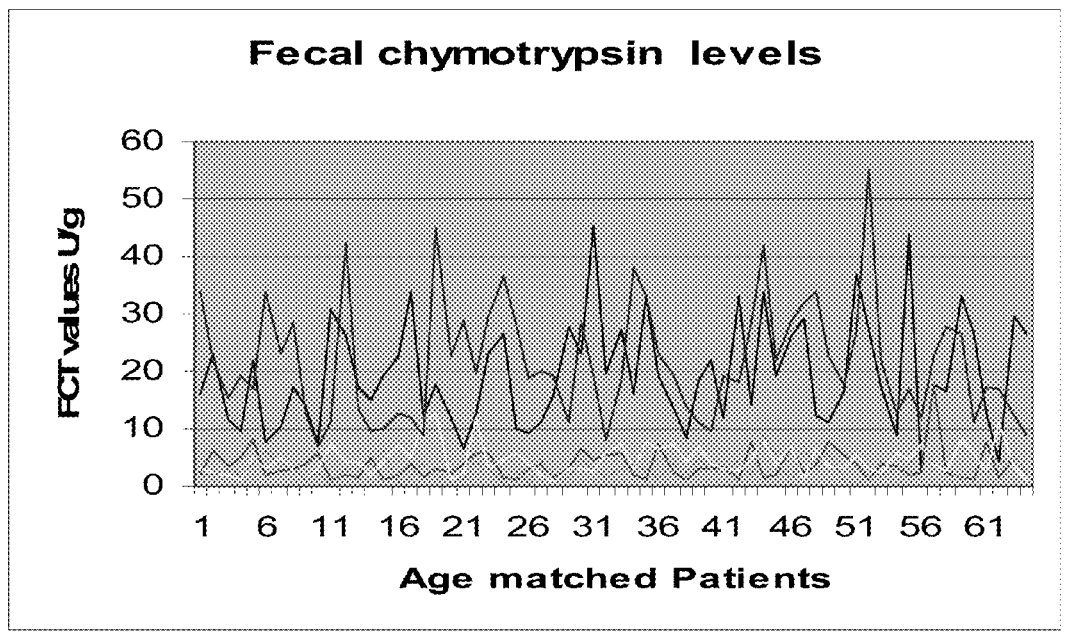
FIG. 13 shows fecal chymotrypsin levels measured in 320 age-matched children. The navy line (in grayscale, the upper, black line) shows FCT levels for children with known conditions (genetic and other conditions). The purple line (in grayscale, the upper, dark gray line), shows FCT levels for normal children without any known condition. The aqua line, (in gray scale, the lower, medium gray line), shows FCT levels for children with autism. The pink line (in gray scale, the lower, dark gray line), shows FCT measurements for children with ADHD. The yellow line (in grayscale, the lower, light gray line), shows FCT measurements for children with ADD.

In Study 6, FCT levels were determined for 320 children aged 2 years to 18 years of age, 64 with autism, 64 with ADD. 64 with ADHD, 64 with known genetic conditions, and 64 normals (no known conditions). The data showed that the children with autism, ADD and ADHD exhibited abnormally low levels of FCT compared to the children with known genetic conditions and normal children. FCT data were gathered during a multi-physician office trial of age-matched children with multiple conditions. FIG. 13 depicts FCT levels in separate groups of children aged 6 years to 18 years who have Autism, ADHD (Attention Deficit Hyperactivity Disorder), ADD (Attention Deficit Disorder), known genetic disorder also diagnosed with autism, or no known condition (normals).

The two upper lines in FIG. 13 correspond to FCT levels in children without any known condition and children with known co-morbid conditions (genetic and others). The three bottom lines correspond to FCT levels in the children with autism, ADD and ADHD.

The Autism, ADD, and ADHD children had significantly lower levels FCT than those without any known condition, or those with a known genetic co-morbidity or traumatic condition ($p<0.01$).

Study 7

In Study 7, 33 children who were diagnosed with autism and abnormally low FCT levels were enrolled in the study. The children were treated with one of two pancreatic/digestive enzyme supplements, or given no treatment. FCT levels were measured for each child at time 0, 30, 60, 90 and 120 days.

Eleven (11) children were given a low therapeutic dose of ULTRASE® MT20 (pancrelipase) Capsules (opened to sprinkle on food) (see below); 11 children were given Viokase® (pancrelipase) powder for sprinkling on food at a minimal dosing level of/teaspoon; 11 children just had their fecal chymotrypsin levels measured. All children were age-matched and without a co-morbid neurological and/or genetic diagnosis.

Each ULTRASE Capsule was orally administered and contained 371 mg of enteric-coated minitablets of porcine pancreatic concentrate contained:

| Lipase | 20,000 U.S.P. Units |
|---|---|
| Amylase | 65,000 U.S.P. Units |
| Protease | 65,000 U.S.P. Units |

Each 0.7 g (¼ Teaspoonful) of Viokase Powder contained:
Lipase, USP units 16,800
Protease, USP units 70,000
Amylase, USP units 70,000

FCT levels were monitored over 120 days to determine whether FCT levels changed in response to treatment with either of the enzyme formulations, compared to the children who did not receive enzyme treatment. The results of the FCT levels, measured over a 120 day period are shown in Table 14 below.

TABLE 14

Mean Fecal Chymotrypsin Levels at Baseline, 30, 60, 90 and 120 days Post administration of Multiple Pancreatic Enzyme Replacement

|  | Ultrase | Viokase | No treatment |
|---|---|---|---|
| Mean FCT (units) At Baseline | 3.49 | 3.81 | 3.1 |
| Mean FCT (units) 30 Days | 5.05 | 7.02 | 3.15 |
| Mean FCT (units) 60 Days | 4.82 | 8.96 | 3.18 |
| Mean FCT (units) 90 Days | 4.91 | 13.73 | 3.25 |
| Mean FCT (units) 120 Days | 5.38 | 15.1 | 3.13 |
|  |  |  | N = 33 |

Figure 14:
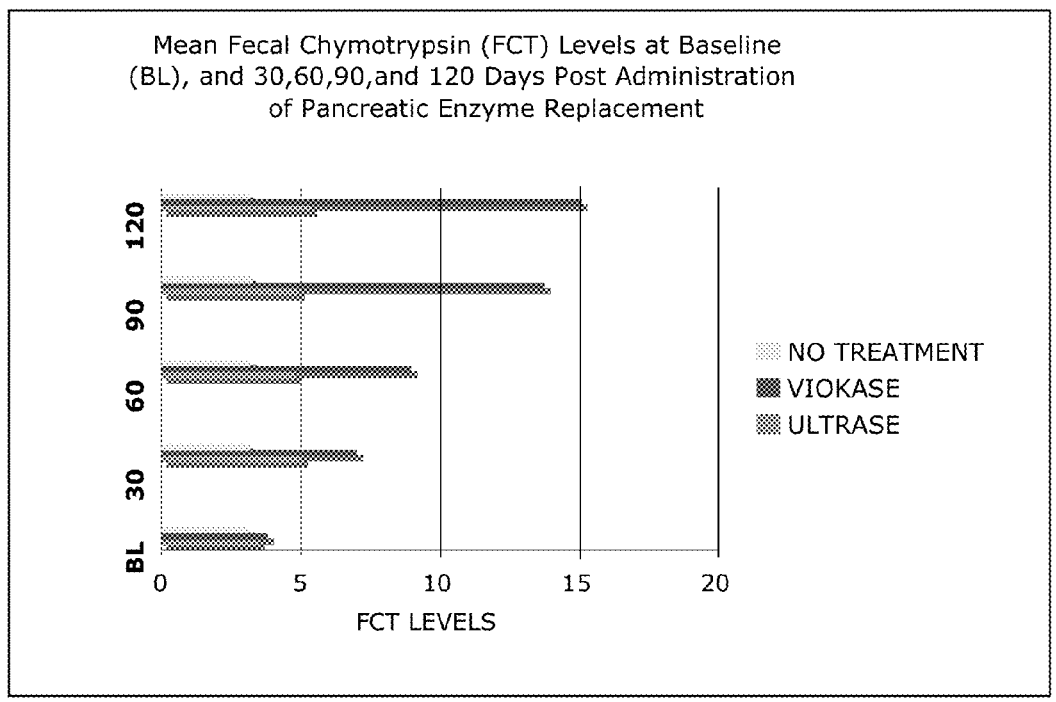
FIG. 14 shows mean fecal chymotrypsin levels at baseline, and 30, 60, 90 and 120 days after administration of Viokas or Ultrase enzyme replacement.

The results are shown in the bar graph in FIG. 14. The top bar (very pale bar) for each time point shows the FCT level for the untreated children. The middle bar shows the FCT level for children treated with Viokase, and the bottom bar at each time point shows the FCT level following Ultrase treatment. The results in the table and graphed in FIG. 14 indicate that a significant change in FCT level was seen only following administration of the Viokase powder enzyme formula, from baseline at time 0 to 120 days. The greatest change was seen in the first 90 days. The changes in the first 90 days were significant compared to the changes seen between 90 and 120 days. While the Ultrase group showed some change from baseline to 120, the change was not significant.

The lipases in Ultrase are very sensitive to pH changes and to degradation in acidic conditions, such as those found in the stomach. The enteric coating on Ultrase allows the enzymes to bypass the stomach. Ultrase has been shown to be useful for delivery of sufficient lipases to treat adults with cystic fibrosis and chronic pancreatitis who suffer from pancreatic enzyme deficiency. However, the enteric coating on Ultrase and other similar products apparently did not allow the protease portion of those compositions to be delivered in the proximal small intestine, where it is needed for protein degradation. As demonstrated in the small pilot study, Ultrase did not allow for release of the protease portion of the enzyme, specifically chymotrypsin, as determined by FCT levels measured following administration of Ultrase. The FCT levels in the Ultrase treated group were similar to those found in the NO TREATMENT group.

The optimum delivery timing and location for the protease portion of the enzyme is from the latter portion of the time the bolus of food is in the stomach, through the time the digesting food spends in the proximal small intestine.

Study 8

In Study 8, 42 age-matched children, 25 with autism, and 17 without autism or other co-morbid condition, were examined using a stool test for the presence of multiple pathogens as well as markers of Gastrointestinal dysfunction, including FCT levels. The children with autism had a larger number of stool pathogens present as well as abnormally low FCT levels.

This small pilot study was undertaken to examine the gastrointestinal flora of children with autism versus those without autism. Multiple markers of gastrointestinal health were examined to determine if there is an abnormal gastrointestinal presentation in these children.

42 children aged matched 25 with autism and 17 without autism or other co-morbid condition were screened using a stool test for the presence of multiple pathogens as well as markers of Gastrointestinal dysfunction. Other GI pathogens or stool markers known to those of skill in the art may also be tested as a marker of GI dysfunction. Table 15 below shows the incidence of presence of a GI pathogen or other stool marker.

TABLE 15

Incidence of the Presence of Pathogens and other Stool Markers Representing Gastrointestinal Dysfunction

|  | AUTISM | % TOTAL | NOT AUTISM | % TOTAL |
|---|---|---|---|---|
| LOW FCT | 25 | 100% | 0 | 0% |
| C. difficile antigen | 15 | 60% | 1 | 6% |
| Fecal Elastase < 200 | 0 | 0% | 0 | 0% |
| H. pylori antigen | 17 | 67% | 0 | 0% |
| E. Histolytica antigen | 8 | 32% | 0 | 0% |
| Giardia antigen | 9 | 36% | 1 | 6% |
| Yeast overgrowth | 4 | 16% | 0 | 0% |
| Cryptosporidium | 9 | 36% | 1 | 6% |
|  | N = 25 |  | N = 17 |  |

The presence of positive stool markers in the children with autism, including low levels of fecal chymotrypsin indicated additional gastrointestinal problems in patients with autism.

Study 9

In Study 9, 68 children aged 3 years to 8 years of age, diagnosed with autism who presented with abnormally low FCT levels were administered a combination of pancreatic/digestive enzymes for 90 days. Results demonstrated significant improvement in 5 out of 5 areas representing both the core and non-core symptoms of autism.

Examination of the multiple areas of symptomology in the children with autism in this study included both gastrointestinal symptoms as well as the core symptoms of autism. It is well documented in the literature that children with autism do not change over time, and that their level of autism is static regardless of the age of the child. Further there is thought to be no maturation changes accompanying those with autism.

In this study, 68 children aged 3-8 diagnosed with autism who presented with abnormally low FCT levels were administered ¼ teaspoonful of Viokase, and a chewable papaya enzyme (Original Papaya Enzyme Brand) at each meal for a period of 90 days.

Original Papaya Enzyme

| Supplement Facts Serving Size: 3 Tablets Servings Per Container: 33 | | |
|---|---|---|
| Carbohydrates | <1 g | <1% |
| Sugars | <1 g | |
| Papain | 45 mg | ** |
| Amylase | 6 mg | ** |
| Protease | 6 mg | ** |
| Papaya Fruit (Carica papaya) | 3 mg | ** |

*Based on a 2,000 calorie diet
**Daily Values not established

The physician and the parent were asked to complete a rating scale for each of the symptoms examined in the study. Each symptom was rated on the scale below with (0) indicating that the child is able to perform the task, thereby demonstrating no impairment, to (10) representing the child's complete inability to perform the task. With respect to undesirable behaviors such as hyperactivity or obsessive compulsive behavior, a change from a lower score to a higher score indicates an improvement, because the child is demonstrating the undesirable behavior less often. The rating scale was as follows:

10 Child experiences a 0% ability to perform this task
9 Child can perform this task 10% of the time
8 Child can perform this task 20% of the time
7 Child can perform this task 30% of the time
6 Child can perform this task 40% of the time
5 Child can perform this task 50% of the time
4 Child can perform this task 60% of the time
3 Child can perform this task 70% of the time
2 Child can perform this task 80% of the time
1 Child can perform this task 90% of the time
0 Child can perform this task 100% of the time The average of the two scores taken at each interval: baseline and 90 days. The scores obtained are shown in Table 16 below:

TABLE 16

Symptom Scores for Children with Autism Pre- and Post-Administration of Digestive Enzymes

|  | Sum of Total Patient Scores Pre-Digestive Enzyme | Mean Score Pre-Digestive Enzyme | Sum Total Patient Scores 90 Days Post Enzyme Admin | Mean Score 90 Days Post Enzyme Admin |
|---|---|---|---|---|
| Hyperactivity | 300 | 4.41 | 568 | 8.35 |
| Obsessive Compulsive Behavior | 255 | 3.75 | 554 | 8.15 |
| Eye Contact | 552 | 8.12 | 206 | 3.03 |
| Speech | 553 | 8.13 | 223 | 3.28 |
| Partial Toilet Training | 515 | 7.57 | 197 | 2.9 |

N = 68

CARS scores have been used to study core symptoms of autism. In study 9, measures of core and non-core symptoms of autism were obtained (hyperactivity, obsessive compulsive behavior, eye contact, speech, partial toilet training) While the diagnosis of autism was made strictly on the basis of a behavioral assessment of the core symptoms of autism, the study indicates that other non-core symptoms such as a lack of toilet training, will lead to significant morbidity in this population. The 5 parameters measured in this study indicated that the increase in toilet training, eye contact, and speech as well as the decrease in hyperactivity and obsessive compulsive behaviors are core and non-core symptoms that were improved by treatment with digestive enzymes.

Study 10 and Study 11

In Studies 10 and 11, 225 children ages 2-4 years of age, and 171 children 5-11 years of age each of whom presented with abnormally low levels of fecal chymotrypsin, were administered a combination of pancreatic/digestive enzymes 3 times a day for a period of 150 days. Nine total measures of autistic symptomotology, both core and non-core, were obtained at baseline and over a period of 150 days. Significant changes representing improvements in both core and non-core symptoms were seen across all age levels, with the greatest change taking place over the first 90 days.

Each of these studies were conducted similar to the protocol in STUDY 9. The children were divided into age groups of 2-4 and 5-11. In these studies, 225 children aged 2-4 and 171 aged 5-11 previously diagnosed with autism who presented with abnormally low fecal chymotrypsin levels were administered ¼ teaspoonful of Viokase, and a chewable papaya enzyme (Original Papaya Enzyme Brand) at each meal for a period of 150 days. The same rating scale used in STUDY 9 was utilized in these two studies. Additionally levels of toilet training, hand flapping, play habits, and formed bowel movements were assessed. The % of the cohorts that experienced changes were calculated as well. This study was extended to 150 days, with no significance seen between day 90 and day 150.

Table 17 below shows the measurements obtained for the percentage of children in each group who exhibited the indicated trait or behavior, including hyperactivity, obsessive compulsive behavior, hand flapping, eye contact, speech, partial toilet training, full toilet training, formed bowel movement and playing well with others.

TABLE 17

PERCENT (%) WITH TRAIT OR SYMPTOM FOLLOWING ENZYME REPLACEMENT

|  | Aged 2-4, N = 225 Therapy Day | | | Aged 5-11, N = 171 Therapy Day | | |
|---|---|---|---|---|---|---|
| Measure | Day 0 | Day 60 | Day 150 | Day 0 | Day 60 | Day 150 |
| Had some eye contact | 4 | 61 | 88 | 14 | 59 | 89 |
| Had some speech | 23 | 58 | 75 | 18 | 64 | 86 |
| Were partially toilet trained | 8 | 61 | 75 | 11 | 47 | 72 |
| Were fully toilet trained | 4 | 30 | 45 | 16 | 16 | 20 |
| Had formed bowel movement | 15 | 88 | 100 | 16 | 18 | 97 |
| Experienced hyperactivity | 85 | 38 | 19 | 98 | 51 | 33 |
| Plays well with others | 12 | 38 | 60 | 36 | 43 | 71 |
| Experienced hand flapping | 81 | 46 | 31 | 1 | 75 | 36 |
| Experienced other OCD | 90 | 73 | 32 | 91 | 58 | 22 |

In studies 9, 10, and 11, measurements of core and non-core symptoms of autism were obtained. While the diagnosis of autism has been made strictly as a result of a behavioral assessment of the core symptoms of autism, other non-core symptoms lead to significant morbidity in this population. The lack of toilet training and formed bowel movements, for example, create a hardship for parents, and often lead to a lack of social integration, further contributing to the core symptoms of autism. This additional isolation due to the non-core symptoms of autism further impedes the child's ability to learn and to integrate socially. This dynamic is continually present in this population. This effect can be a significant driver of the core symptoms of autism. This demonstrates that these non-core symptoms may also be valuable as indicators of autism.

Example 12

Enzyme Delivery System Used in the Treatment of Autism

Encapsulated digestive enzyme preparations according to this invention are packaged in pouches containing 900 mg/pouch, and are administered to a patient in need thereof by sprinkling the contents of one pouch onto food just before serving, administered three times per day. Determination of whether a patient is in need of administration of treatment with digestive enzymes including encapsulated digestive enzyme preparations such as those of this invention can be made using any test or indicator that is useful as a marker of a digestive enzyme deficiency. This determination is made, for example, using FCT levels, behavioral symptoms (core or non-core symptoms of autism), or detection of a mutation in a gene affecting the activity and/or expression of digestive enzymes, for example, a MET gene mutation.

Relevant symptoms of the patient's condition or disease are measured before and following a period of treatment. The percentage of patients exhibiting some eye contact, some speech, partial toilet training, full toilet training, formed bowel movements, and ability to play well with others increases at 60 days, or earlier than 60 days, with a further increase at 150 days. The changes observed upon treatment with the digestive enzymes of this invention take place over a shorter time course, and/or result in greater improvement in each individual at any given time point and/or improvements in core and non-core symptoms in a higher percentage of individuals treated. In addition, a corresponding increase in the number of patients exhibiting a decrease in hyperactivity, hand flapping, or another OCD is observed at 60 days, with a further increase in the number of patients exhibiting a decrease in those behaviors at 150 days.

Other core symptoms of autism such as those measured in a CARS test are also observed and shown to improve following treatment.

What is claimed is:

1. A coated free-flowing particulate digestive enzyme preparation, comprising particles that comprise:
   (a) a core comprising digestive enzymes, wherein the digestive enzymes comprise a protease, an amylase and a lipase; and
   (b) a coating comprising an emulsifiable lipid, wherein the coating coats the core and the emulsifiable lipid emulsifies upon exposure to a solvent;
   wherein the digestive enzymes are present in an amount of from 77.5-82.5% by weight of the particles, and
   wherein the coating masks the taste and smell of the digestive enzymes.

2. The coated free-flowing particulate digestive enzyme preparation of claim 1, wherein the coated free-flowing particulate digestive enzyme preparation provides a therapeutically effective amount of the digestive enzymes to treat a subject suffering from autism, Attention Deficit Disorder (ADD), or Attention Deficit Hyperactivity Disorder (ADHD).

3. The coated free-flowing particulate digestive enzyme preparation of claim 1, wherein the core is from about 105 µm to about 425 µm.

4. The coated free-flowing particulate digestive enzyme preparation of claim 1, wherein the core is sieved from about 40 mesh to about 140 mesh.

5. The coated free-flowing particulate digestive enzyme preparation of claim 1, wherein the preparation is non-aerosolizable.

6. The coated free-flowing particulate digestive enzyme preparation of claim 1, wherein the emulsifiable lipid is selected from the group consisting of hydrogenated soy oil, hydrogenated castor wax, and carnauba wax.

7. The coated free-flowing particulate digestive enzyme preparation of claim 1, wherein about 80% of the digestive enzymes are released by 30 minutes in a dissolution test performed at pH 6.0.

8. The coated free-flowing particulate digestive enzyme preparation of claim 1, wherein the coating consists essentially of the emulsifiable lipid that is one or more monoglycerides.

9. The coated free-flowing particulate digestive enzyme preparation of claim 1, wherein the emulsifiable lipid comprises monoglycerides.

10. The coated free-flowing particulate digestive enzyme preparation of claim 1, wherein at least 90% of the particles are sieved from about #40 to about #140 mesh in size.

11. The coated free-flowing particulate digestive enzyme preparation of claim 1, wherein less than 20%, or less than 15%, of the particles can be sieved through #100 mesh.

12. The coated free-flowing particulate digestive enzyme preparation of claim 1, wherein the emulsifiable lipid comprises at least one hydrophilic group and at least one hydrophobic group.

13. The coated free-flowing particulate digestive enzyme preparation of claim 12, wherein the emulsifiable lipid is capable of forming a hydrophilic and hydrophobic interface.

14. The coated free-flowing particulate digestive enzyme preparation of claim 13, wherein the interface is a micelle interface.

15. The coated free-flowing particulate digestive enzyme preparation of claim 13, wherein the interface is a bilayer interface.

16. The coated free-flowing particulate digestive enzyme preparation of claim 12, wherein the emulsifiable lipid is obtained from animal or vegetable origins.

17. The coated free-flowing particulate digestive enzyme preparation of claim 16, wherein the emulsifiable lipid is selected from the group consisting of palm kernel oil, soybean oil, cottonseed oil, canola oil, poultry fat, hydrogenated soy oil, hydrogenated castor wax, and carnauba wax.

18. The coated free-flowing particulate digestive enzyme preparation of claim 1, wherein the emulsifiable lipid is hydrogenated, saturated or partially saturated.

19. The coated free-flowing particulate digestive enzyme preparation of claim 1, wherein the emulsifiable lipid consists of hydrogenated soy oil.

20. The coated free-flowing particulate digestive enzyme preparation of claim 1, wherein the emulsifiable lipid is selected from the group consisting of monoglycerides, diglycerides, fatty acids, esters of fatty acids, phospholipids, salts thereof, and combinations thereof.

21. The coated free-flowing particulate digestive enzyme preparation of claim 20, comprising the esters of fatty acids, wherein the esters of fatty acids are selected from the group consisting of acetic acid esters of mono- and diglycerides, citric acid esters of mono- and diglycerides, lactic acid esters of mono- and diglycerides, polyglycerol esters of fatty acids, propylene glycol esters of fatty acids, and diacetyl tartaric acid esters of mono- and diglycerides.

22. The coated free-flowing particulate digestive enzyme preparation of claim 1, wherein the emulsifiable lipid is a food grade emulsifiable lipid.

23. The coated free-flowing particulate digestive enzyme preparation of claim 22, wherein the food grade emulsifiable lipid comprises sorbitan monostearates, sorbitan tristearates, or calcium stearoyl lactylates.

24. The coated free-flowing particulate digestive enzyme preparation of claim 1, wherein the core is processed by a technique selected from the group consisting of encapsulation, compression, extrusion and molding.

25. The coated free-flowing particulate digestive enzyme preparation of claim 1, wherein at least 75% of the particles are sieved from about #40 to about #80 mesh in size.

26. The coated free-flowing particulate digestive enzyme preparation of claim 1, wherein the emulsifiable lipid comprises hydrogenated soy oil.

27. The coated free-flowing particulate digestive enzyme preparation of claim 1, wherein the coating consists essentially of the emulsifiable lipid that is hydrogenated soy oil.

28. The coated free-flowing particulate digestive enzyme preparation of claim 1, wherein the digestive enzymes have a protease activity of not less than 156 USP units/mg.

29. The coated free-flowing particulate digestive enzyme preparation of claim 1, wherein the core comprises the digestive enzymes present in an amount of 80% by weight of the particles.

30. The coated free-flowing particulate digestive enzyme of claim 1, wherein at least 90% of the particles are from about 105 to about 425 μm.

31. The coated free-flowing particulate digestive enzyme preparation of claim 1, wherein less than 20% of the particles can be sieved through about 150 μm mesh.

32. The coated free-flowing particulate digestive enzyme preparation of claim 1, wherein less than 15% of the particles can be sieved through about 150 μm mesh.

33. The coated free-flowing particulate digestive enzyme preparation of claim 1, wherein at least 75% of the particles are from about 180 to about 425 μm.

34. The coated free-flowing particulate digestive enzyme preparation of claim 1 or 27, wherein the digestive enzymes are a pancreatin composition.

35. A pharmaceutical composition comprising a therapeutically effective amount of a coated free-flowing particulate digestive enzyme preparation, wherein the preparation comprises particles that comprise:
   a core comprising digestive enzymes, wherein the digestive enzymes comprise a protease, an amylase and a lipase; and,
   a coating comprising an emulsifiable lipid, wherein the coating coats the core and the emulsifiable lipid emulsifies upon exposure to a solvent;
   wherein the digestive enzymes are present in an amount of from 77.5-82.5% by weight of the particles, wherein the coating masks the taste and smell of the digestive enzymes and wherein the therapeutically effective amount of the coated free-flowing particulate digestive enzyme preparation is effective to treat a subject suffering from autism, Attention Deficit Disorder (ADD), or Attention Deficit Hyperactivity Disorder (ADHD).

36. The pharmaceutical composition of claim 35, provided in a sachet or a pouch.

37. The pharmaceutical composition of claim 35, wherein at least 80% of the digestive enzymes are released by 30 minutes in a dissolution test performed at pH 6.0.

38. The pharmaceutical composition of claim 35, wherein at least 90% of the particles are sieved from about #40 to about #140 mesh in size.

39. The pharmaceutical composition of claim 35, wherein less than 20% of the particles can be sieved through #100 mesh.

40. The pharmaceutical composition of claim 35, wherein at least 75% of the particles are sieved from about #40 to about #80 mesh in size.

41. The pharmaceutical composition of claim 35, wherein the emulsifiable lipid comprises hydrogenated soy oil.

42. The pharmaceutical composition of claim 35, wherein the coating consists essentially of the emulsifiable lipid that is hydrogenated soy oil.

43. The pharmaceutical composition of claim 35, wherein the digestive enzymes have a protease activity of not less than 156 USP units/mg.

44. The pharmaceutical composition of claim 35, wherein the core comprises the digestive enzymes present in an amount of 80% by weight of the particles.

45. The pharmaceutical composition of claim 35, wherein at least 90% of the particles are from about 105 to about 425 μm.

46. The pharmaceutical composition of claim 35, wherein less than 20% of the particles can be sieved through about 150 μm mesh.

47. The pharmaceutical composition of claim 35, wherein less than 15% of the particles can be sieved through about 150 μm mesh.

48. The pharmaceutical composition of claim 35, wherein at least 75% of the particles are from about 180 to about 425 μm.

49. The pharmaceutical composition of claim 35 or 42, wherein the digestive enzymes are a pancreatin composition.

50. A pharmaceutical composition comprising a dose of a coated free-flowing particulate digestive enzyme preparation, wherein the preparation comprises particles that comprise:
   a core comprising digestive enzymes, wherein the digestive enzymes comprise a protease, an amylase and a lipase; and
   a coating to provide for controlled release of the digestive enzymes, wherein the coating comprises an emulsifiable lipid, wherein the emulsifiable lipid is a soy lipid;
   wherein the digestive enzymes are present in an amount of from 77.5-82.5% by weight of the particles, wherein the coating masks the taste and smell of the digestive enzymes, and wherein the digestive enzymes have a protease activity of not less than 156 USP units/mg.

51. The pharmaceutical composition of claim 50, wherein the digestive enzymes are present in an amount effective for treatment of a subject suffering from autism, ADD, or ADHD.

52. The pharmaceutical composition of claim 50, wherein the emulsifiable lipid is hydrogenated soy oil, hydrogenated castor wax, or carnauba wax.

53. The pharmaceutical composition of claim 50, wherein the dose is provided in a sachet or pouch.

54. The pharmaceutical composition of claim 50, wherein at least 90% of the particles are sieved from about #40 to about #140 mesh in size.

55. The pharmaceutical composition of claim 50, wherein less than 20% of the particles can be sieved through #100 mesh.

56. The pharmaceutical composition of claim 50, wherein at least 75% of the particles are sieved from #40 to about #80 mesh in size.

57. The pharmaceutical composition of claim 50, wherein the coating consists essentially of the emulsifiable lipid that is hydrogenated soy oil.

58. The pharmaceutical composition of claim 50, wherein the core comprises the digestive enzymes present in an amount of 80% by weight of the particles.

59. The pharmaceutical composition of claim 50, wherein at least 90% of the particles are from about 105 to about 425 μm.

60. The pharmaceutical composition of claim 50, wherein less than 20% of the particles can be sieved through about 150 μm mesh.

61. The pharmaceutical composition of claim 50, wherein less than 15% of the particles can be sieved through about 150 μm mesh.

62. The pharmaceutical composition of claim 50, wherein at least 75% of the particles are from about 180 to about 425 μm.

63. The pharmaceutical composition of claim 50 or 57, wherein the digestive enzymes are a pancreatin composition.

64. The pharmaceutical composition of claim 50, wherein the dose contains about 900 mg of the coated free-flowing particulate digestive enzyme preparation.

65. The pharmaceutical composition of claim 50, wherein the coating is generally uniform.

* * * * *